US009957333B2

(12) United States Patent
Salomon et al.

(10) Patent No.: US 9,957,333 B2
(45) Date of Patent: May 1, 2018

(54) ANTI-CEP ANTIBODY OR FRAGMENT THEREOF

(71) Applicant: Case Western Reserve University, Cleveland, OH (US)

(72) Inventors: Robert G. Salomon, Cleveland, OH (US); John W. Crabb, Cleveland, OH (US); Yalun Cui, Cleveland, OH (US); Nicholas D. Tomko, Cleveland, OH (US)

(73) Assignees: Case Western Reserve University, Cleveland, OH (US); The Cleveland Clinic Foundation, Cleveland, OH (US)

( * ) Notice: Subject to any disclaimer, the term of this patent is extended or adjusted under 35 U.S.C. 154(b) by 0 days. days.

(21) Appl. No.: 14/689,948

(22) Filed: Apr. 17, 2015

(65) Prior Publication Data

US 2016/0215067 A1     Jul. 28, 2016

Related U.S. Application Data

(60) Provisional application No. 61/980,958, filed on Apr. 17, 2014.

(51) Int. Cl.
| | | |
|---|---|---|
| *C07K 16/40* | (2006.01) | |
| *A61K 39/395* | (2006.01) | |
| *C07K 16/44* | (2006.01) | |
| *A61K 39/00* | (2006.01) | |

(52) U.S. Cl.
CPC ........ *C07K 16/44* (2013.01); *A61K 2039/505* (2013.01); *C07K 2317/24* (2013.01); *C07K 2317/76* (2013.01); *C07K 2317/92* (2013.01)

(58) Field of Classification Search
CPC ........................................ C07K 16/00–16/468
See application file for complete search history.

(56) References Cited

U.S. PATENT DOCUMENTS

| | | | | |
|---|---|---|---|---|
| 7,172,874 B2* | 2/2007 | Hollyfield | .......... | G01N 33/5308 435/7.1 |
| 7,429,487 B2* | 9/2008 | Pytela | .................... | C07K 16/00 435/326 |
| 8,137,991 B2* | 3/2012 | Crabb | .................... | C07K 16/44 424/130.1 |
| 8,399,626 B2* | 3/2013 | Brinkmann | ............ | A61K 39/00 530/387.3 |

OTHER PUBLICATIONS

Salomon et al., Chem. Res. Toxicol. 2011; 24:1803-16.*
Gu et al., J. Biol. Chem. 2003; 278:42027-35.*
Ebrahem et al. Proc. Nat'l Acad. Sci. 2006; 103:13480-84.*
Almagro & Fransson, Frontiers in Bioscience 2008; 13:1619-33.*
PJ Carter, Nat Rev Immunol, 2006; 6:343-357.*
De Genst et al., Dev Comp Immunol 2006; 30:187-98.*

* cited by examiner

*Primary Examiner* — Jessica H Roark
(74) *Attorney, Agent, or Firm* — Tarolli, Sundheim, Covell & Tummino LLP

(57) ABSTRACT

An isolated anti-carboxyethylpyrrole (anti-CEP) antibody or antigen binding portion thereof includes a heavy chain variable domain that includes three CDRs having at least 90% sequence identity to the three heavy chain CDRs of SEQ ID NO: 7, and a light chain variable domain that includes three CDRs having at least 90% sequence identity to the three light chain CDRs of SEQ ID NO: 8.

15 Claims, 18 Drawing Sheets

Variable Heavy (118 residues)
                CDRH1                                CDRH2
QIQLIQSGPELKKPGETVKISCKPSGYAFTKYGMDWVKQAPGEGLKWMGRINTYTGEPTYADDF
                                CDRH3
KGRFAFSLEASASTAYLQINNLKNEDTATYFCARRRDGYPFAYWGQGTLVTVSS

Variable Light (108 residues)
                CDRL1                                CDRL2
DIVMTQSHKFMSTSVRDRVSITCKASQDVSTAVAWYQQKPGQSPKILIYSASYRFPGVPDRFTG
                              CDRL3
SGSGTDFTFTISSVQAEDLAVYYCHQHYFIPYTFGGGTKLEIKR

Fig. 1

Variable Heavy

```
            1                                                      54
huVH   (1)  QVQLVQSGAEVKKPGASVKVSCKASGYAFTKYGMDWVRQAPGQGLEWMGRINTY
mumVH  (1)  QIQLIQSGPELKKPGETVKISCKPSGYAFTKYGMDWVKQAPGEGLKWMGRINTY
            55                                                     108
HuVH   (55) TGEPTYADDFKGRVTITADTSTSTAYMELSSLRSEDTAVYYCARRRDGYPFAYW
MumVH  (55) TGEPTYADDFKGRFAFSLEASASTAYLQINNLKNEDTATYFCARRRDGYPFAY
            109
HuVH  (109) GQGTLVTVSS
MumHV (109) GQGTLVYVSS
```

Variable Light

```
            1                                                      54
huVL   (1)  DIVMTQSPDSLAVSLGERATINCKASQDVSTAVAWYQQKPGQPPKLLIYSASYR
mumVL  (1)  DIVMTQSHKFMSTSVRDRVSITCKASQDVSTAVAWYQQKPGQSPKILIYSASYR
            55                                                     108
huVL   (55) FPGVPDRFSGSGSGTDFTLTISSLQAEDVAVYYCHQHYFIPYTFGGGTKLEIKR
mumVL  (55) FPGVPDRFTGSGSGTDFTFTISSVQAEDLAVYYCHQHYFIPYTFGGGTKLEIKR
```

Fig. 2

Humanized variable light

```
        H2F1                                  H2R2
CAGGTGCAATTGGTGCAGTCTGGAGCTGAGGTGAAGAAGCCTGGAGCCTCAGTCAAGGTTT
                                 H2F3
CCTGCAAGGCATCTGGGTATGCCTTCACAAAGTATGGAATGGACTGGGTGCGACAGGCTCC
        H2R4                                  H2F5
AGGACAAGGTTTAGAGTGGATGGGCCGGATAAACACCTACACGGGAGAGCCAACATATGC
                                    H2R6
TGATGACTTCAAGGGACGGGTCACCATCACCGCTGACACGTCTACGAGCACTGCCTATATG
         H2F7                                 H2R8
GAGCTGTCGTCTCTCAGATCTGAGGACACGGCTGTGTATTACTGTGCAAGAAGACGAGATG
                        H2F9
GTTACCCGTTTGCTTACTGGGGCCAAGGGACTCTGGTCACCGTATCCTCA
```

Humanized variable light

```
           L2F1                                L2R2
GACATTGTGATGACCCAGTCTCCAGACTCCCTGGCTGTGTCTCTGGGCGAGAGGGCCACCA
                              L2F3
TCAACTGCAAGGCCAGTCAGGATGTGAGTACTGCTGTAGCCTGGTATCAACAGAAACCAGG
          L2R4                                  L2F5
ACAACCTCCTAAATTGCTGATTTACTCGGCATCCTACCGGTTCCCTGGAGTCCCTGATCGCT
                                  L2R6
TCAGCGGCAGTGGATCTGGGACGGATTCACTCTCACCATCAGCAGTCTGCAGGCTGAAGA
         L2F7                                  L2R8
CGTGGCAGTTTATTACTGTCACCAACATTATTTTATTCCGTACACGTTTGGAGGGGGAACCA
AGCTGGAAATAAAACGG
```

Fig. 3

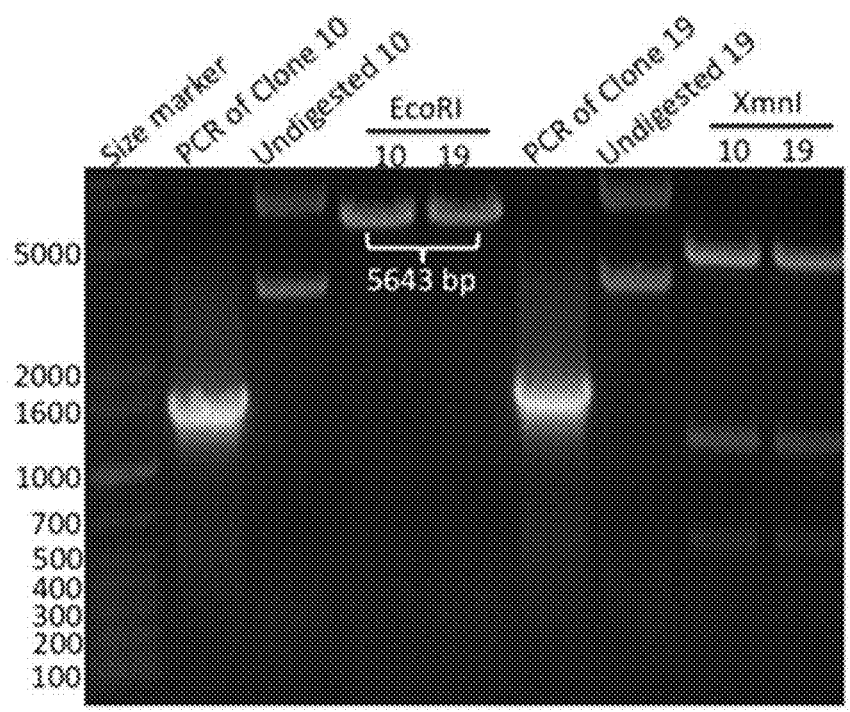
Fig. 6
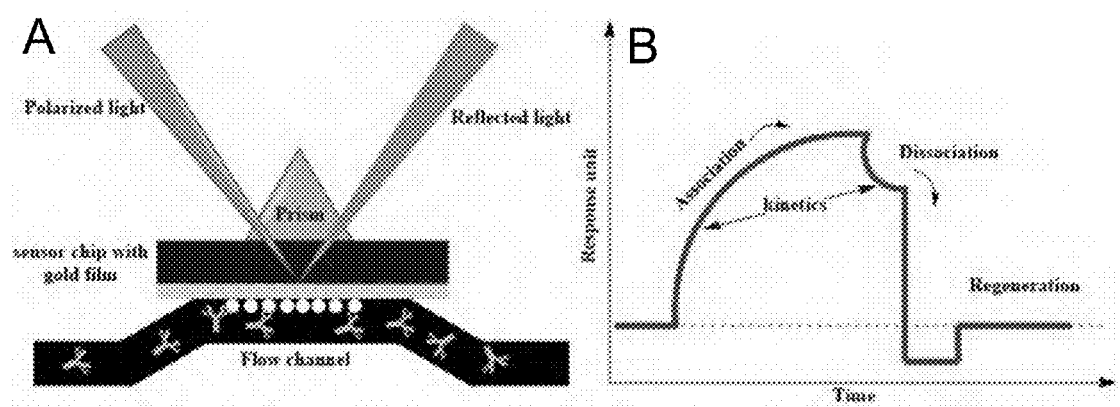
Figs. 7A-B

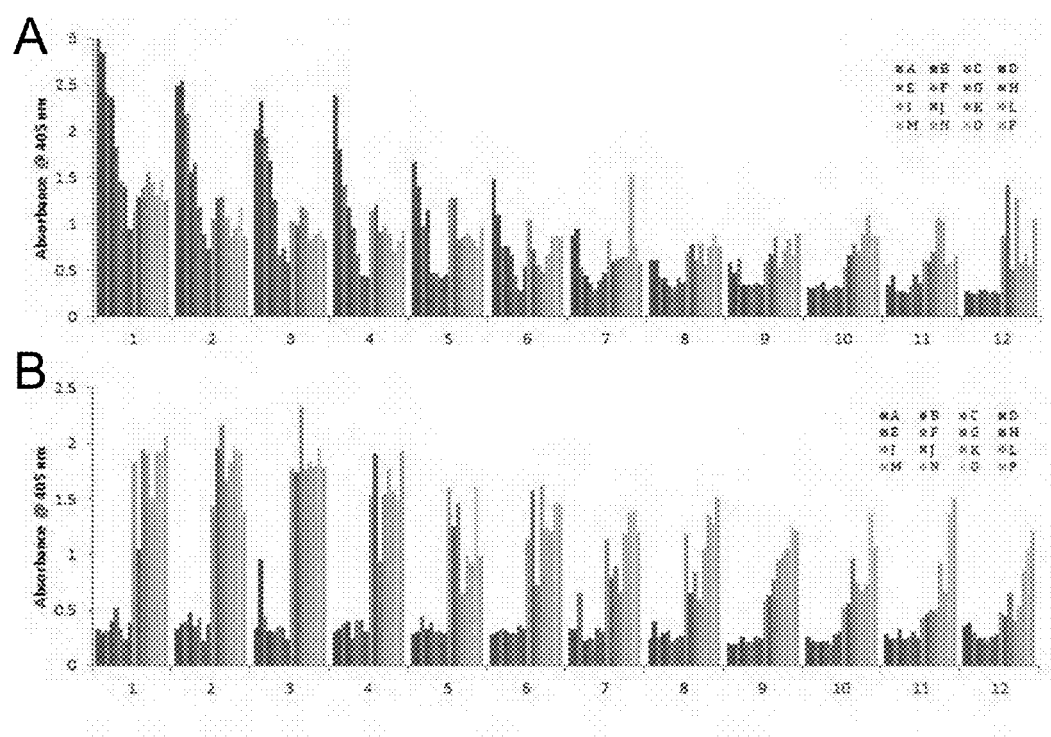
Figs. 8A-B

A
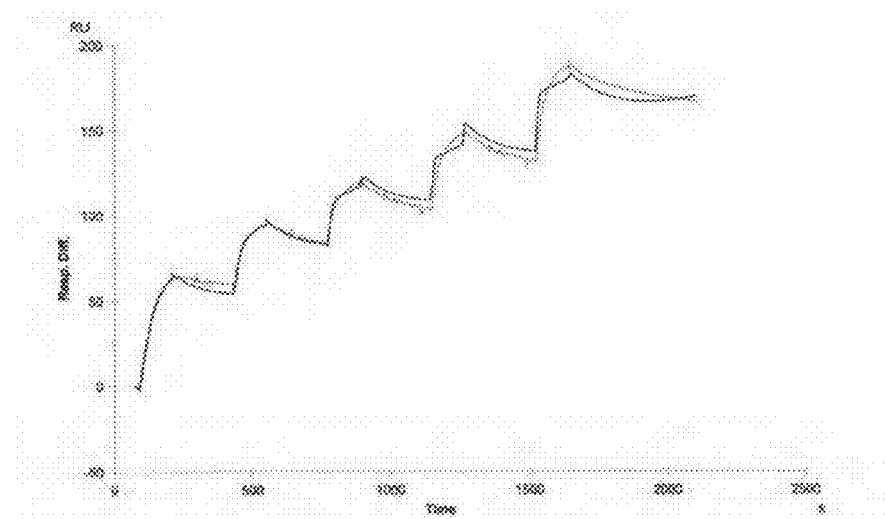
B
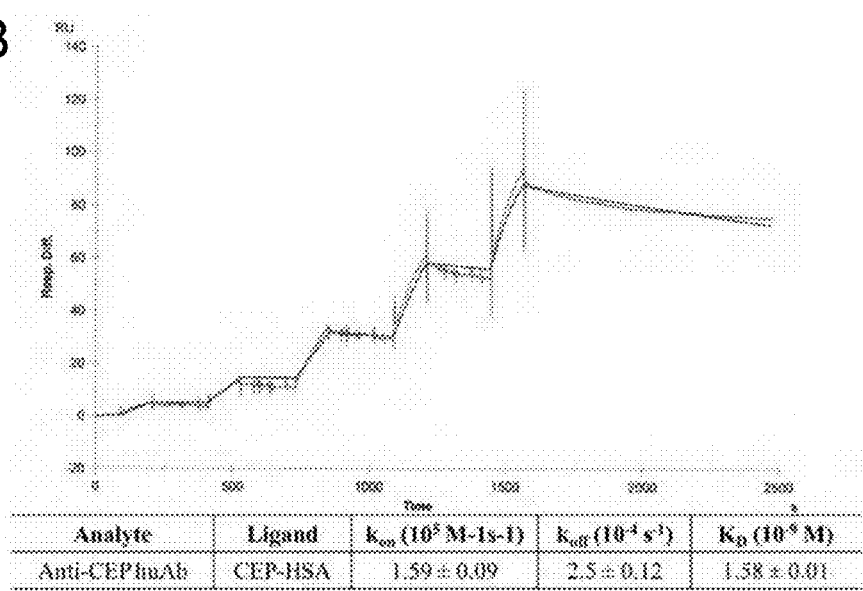
Figs. 9A-B

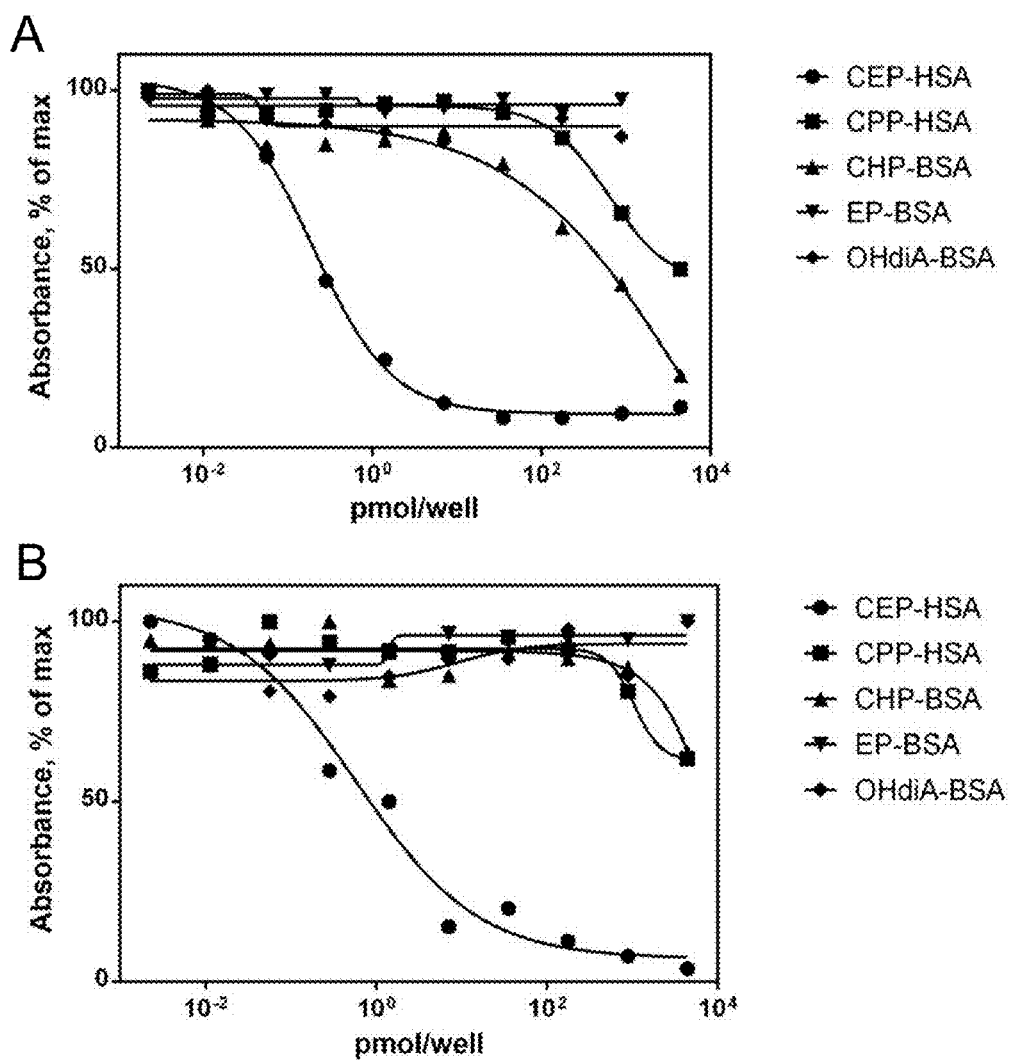
Figs. 10A-B

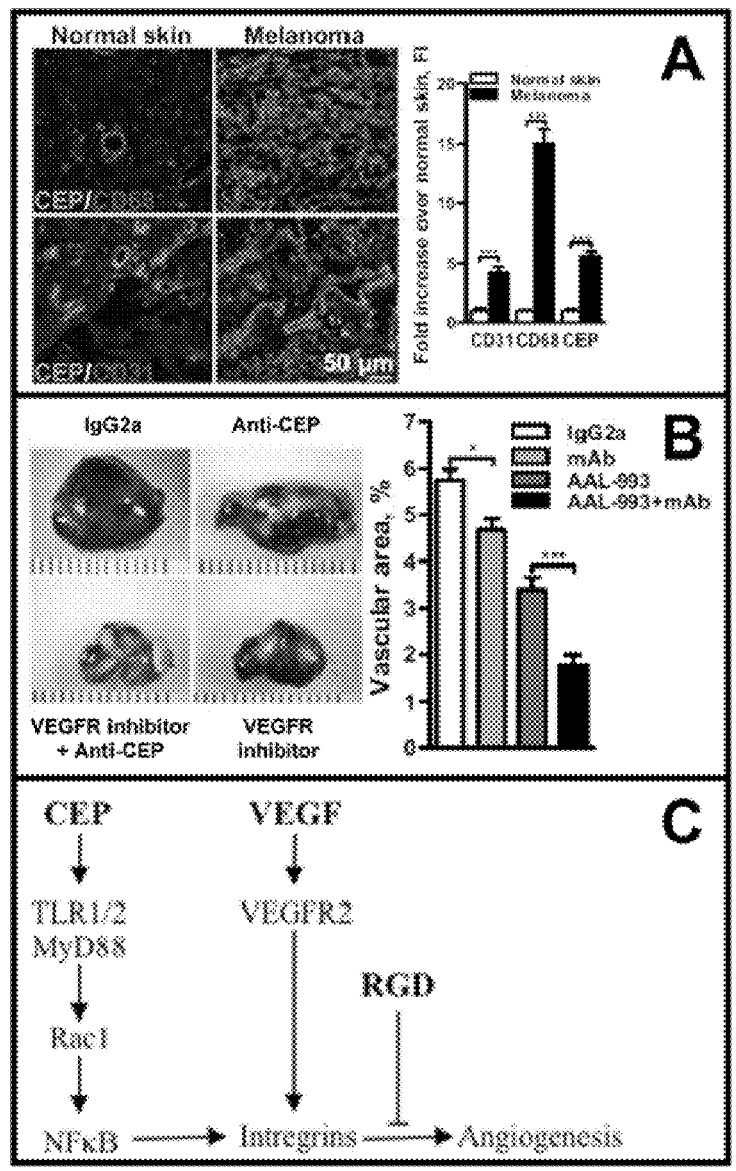
Figs. 13A-C

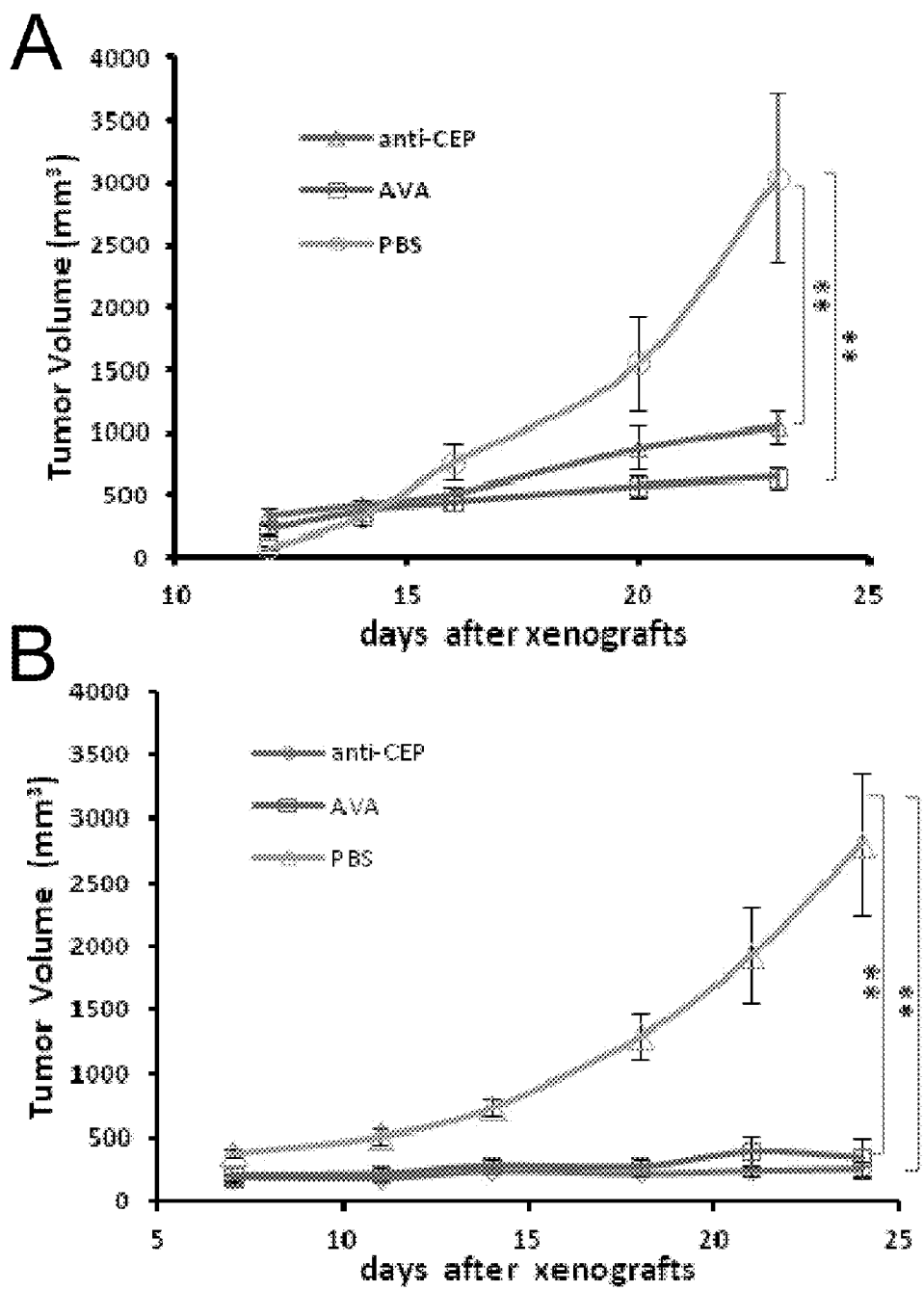
Figs. 14A-B

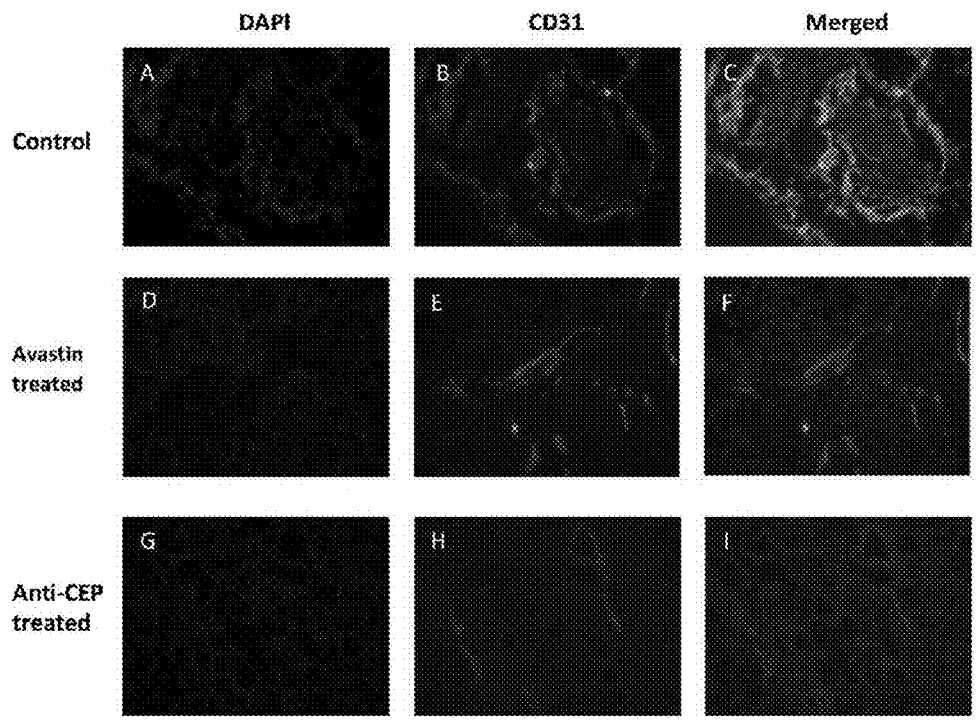
Figs. 15A-I
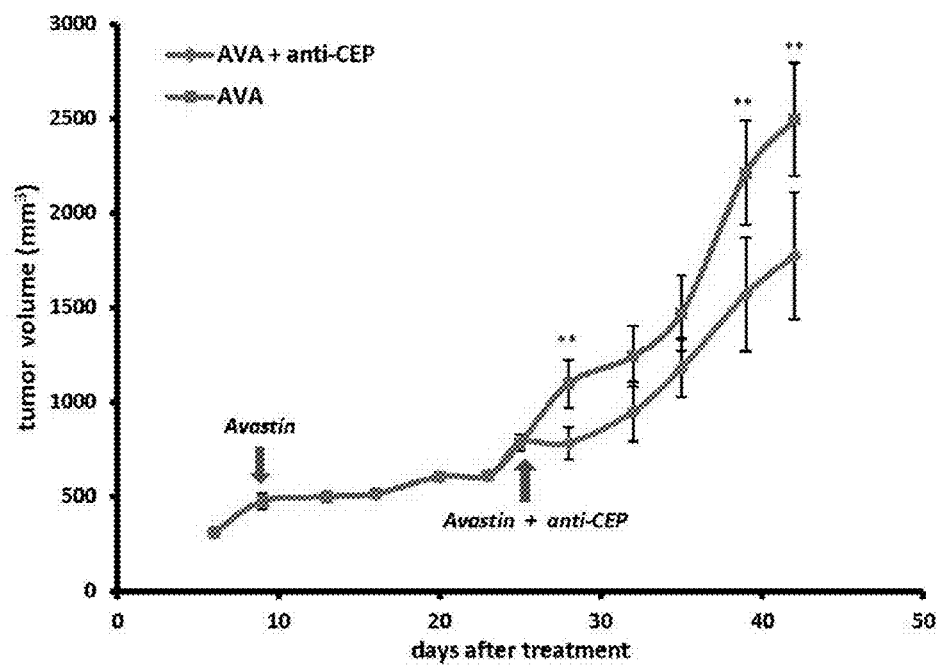
Fig. 16

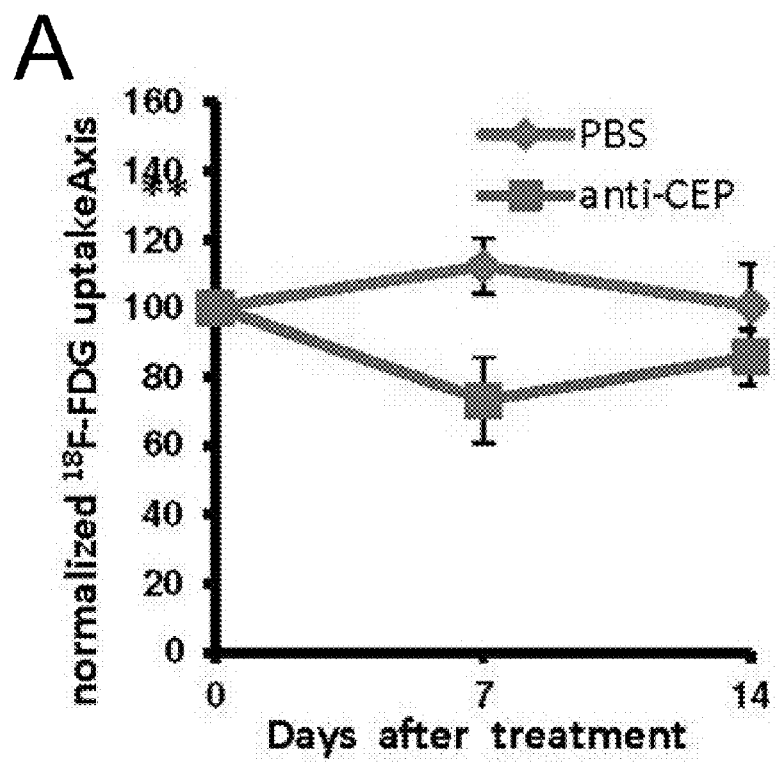
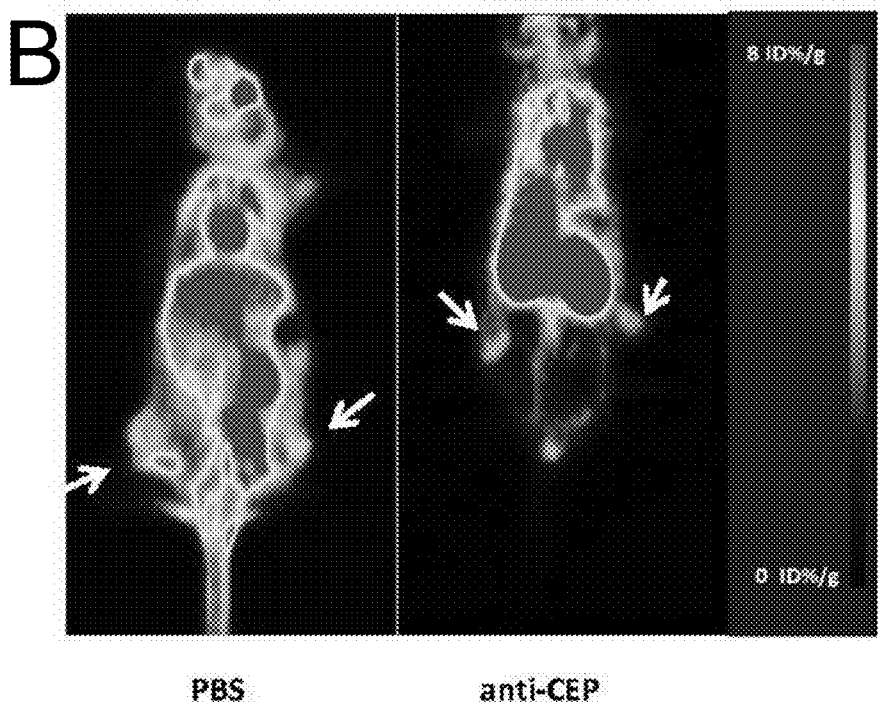
Figs. 17A-B

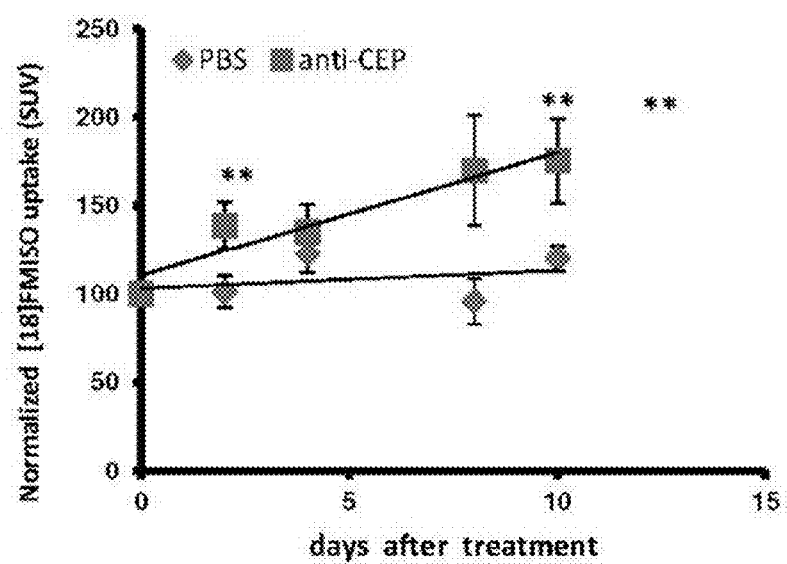
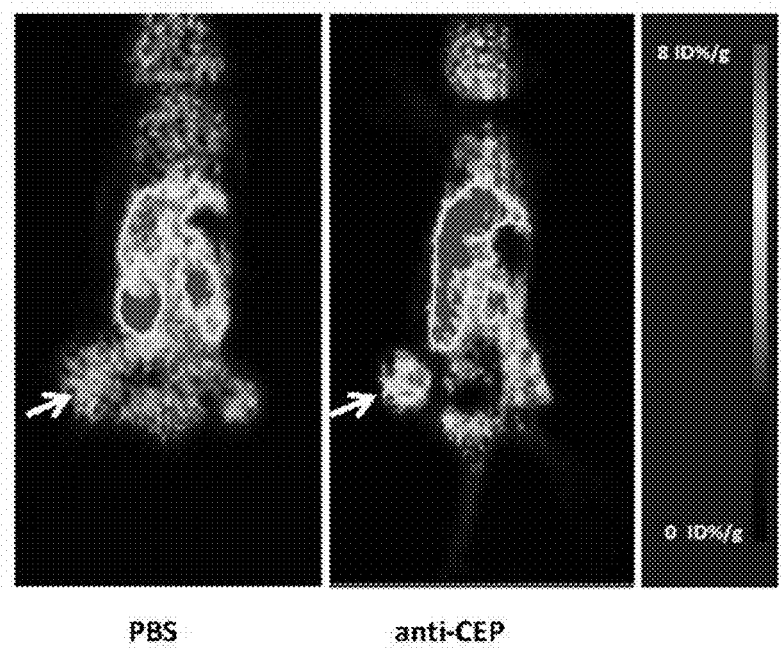
Figs. 18A-B

SEQUENCE LISTING

```
<160> NUMBER OF SEQ ID NOS: 60

<210> SEQ ID NO 1
<211> LENGTH: 10
<212> TYPE: PRT
<213> ORGANISM: Mus musculus

<400> SEQUENCE: 1

Gly Tyr Ala Phe Thr Lys Tyr Gly Met Asp
1               5                   10

<210> SEQ ID NO 2
<211> LENGTH: 17
<212> TYPE: PRT
<213> ORGANISM: Mus musculus

<400> SEQUENCE: 2

Arg Ile Asn Thr Tyr Thr Gly Glu Pro Thr Tyr Ala Asp Asp Phe Lys
1               5                   10                  15
Gly

<210> SEQ ID NO 3
<211> LENGTH: 9
<212> TYPE: PRT
<213> ORGANISM: Mus musculus

<400> SEQUENCE: 3

Arg Arg Asp Gly Tyr Pro Phe Ala Tyr
1               5

<210> SEQ ID NO 4
<211> LENGTH: 11
<212> TYPE: PRT
<213> ORGANISM: Mus musculus

<400> SEQUENCE: 4

Lys Ala Ser Gln Asp Val Ser Thr Ala Val Ala
1               5                   10

<210> SEQ ID NO 5
<211> LENGTH: 7
<212> TYPE: PRT
<213> ORGANISM: Mus musculus

<400> SEQUENCE: 5

Ser Ala Ser Tyr Arg Phe Pro
1               5

<210> SEQ ID NO 6
<211> LENGTH: 9
<212> TYPE: PRT
<213> ORGANISM: Mus musculus

<400> SEQUENCE: 6
```

-continued

```
His Gln His Tyr Phe Ile Pro Tyr Thr
1               5

<210> SEQ ID NO 7
<211> LENGTH: 118
<212> TYPE: PRT
<213> ORGANISM: Mus musculus

<400> SEQUENCE: 7

Gln Ile Gln Leu Ile Gln Ser Gly Pro Glu Leu Lys Lys Pro Gly Glu
1               5                   10                  15

Thr Val Lys Ile Ser Cys Lys Pro Ser Gly Tyr Ala Phe Thr Lys Tyr
            20                  25                  30

Gly Met Asp Trp Val Lys Gln Ala Pro Gly Glu Gly Leu Lys Trp Met
        35                  40                  45

Gly Arg Ile Asn Thr Tyr Thr Gly Glu Pro Thr Tyr Ala Asp Asp Phe
    50                  55                  60

Lys Gly Arg Phe Ala Phe Ser Leu Glu Ala Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Arg Arg Asp Gly Tyr Pro Phe Ala Tyr Trp Gly Gln Gly Thr
            100                 105                 110

Leu Val Thr Val Ser Ser
        115

<210> SEQ ID NO 8
<211> LENGTH: 108
<212> TYPE: PRT
<213> ORGANISM: Mus musculus

<400> SEQUENCE: 8

Asp Ile Val Met Thr Gln Ser His Lys Phe Met Ser Thr Ser Val Arg
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Ile Leu Ile
        35                  40                  45

Tyr Ser Ala Ser Tyr Arg Phe Pro Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105

<210> SEQ ID NO 9
<211> LENGTH: 118
<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
```

```
                    20                  25                  30
Gly Met Asp Trp Val Arg Gln Ala Pro Gly Gln Gly Leu Glu Trp Met
                35                  40                  45

Gly Arg Ile Asn Thr Tyr Thr Gly Glu Pro Thr Tyr Ala Asp Asp Phe
         50                  55                  60

Lys Gly Arg Val Thr Ile Thr Ala Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Arg Asp Gly Tyr Pro Phe Ala Tyr Trp Gly Gln Gly Thr
                100                 105                 110

Leu Val Thr Val Ser Ser
        115

<210> SEQ ID NO 10
<211> LENGTH: 108
<212> TYPE: PRT
<213> ORGANISM: Artificial Sequence
<220> FEATURE:
<223> OTHER INFORMATION: Synthetic Construct

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
                20                  25                  30

Val Ala Trp Tyr Gln Gln Lys Pro Gly Gln Pro Pro Lys Leu Leu Ile
            35                  40                  45

Tyr Ser Ala Ser Tyr Arg Phe Pro Gly Val Pro Asp Arg Phe Ser Gly
        50                  55                  60

Ser Gly Ser Gly Thr Asp Phe Thr Leu Thr Ile Ser Ser Leu Gln Ala
 65                 70                  75                  80

Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105

<210> SEQ ID NO 11
<211> LENGTH: 354
<212> TYPE: DNA
<213> ORGANISM: Artificial Sequence
<220> FEATURE:
<223> OTHER INFORMATION: Synthetic Construct

<400> SEQUENCE: 11
caggtgcaat tggtgcagtc tggagctgag gtgaagaagc ctggagcctc agtcaaggtt      60
tcctgcaagg catctgggta tgccttcaca agtatggaa tggactgggt gcgacaggct     120
ccaggacaag gtttagagtg gatgggccgg ataaacacct acacgggaga gccaacatat     180
gctgatgact tcaagggacg ggtcaccatc accgctgaca cgtctacgag cactgcctat     240
atggagctgt cgtctctcag atctgaggac acggctgtgt attactgtgc aagaagacga     300
gatggttacc cgtttgctta ctggggccaa gggactctgg tcaccgtatc ctca           354

<210> SEQ ID NO 12
<211> LENGTH: 324
<212> TYPE: DNA
<213> ORGANISM: Artificial Sequence
<220> FEATURE:
```

<223> OTHER INFORMATION: Synthetic Construct

<400> SEQUENCE: 12

```
gacattgtga tgacccagtc tccagactcc ctggctgtgt ctctgggcga gagggccacc    60
atcaactgca aggccagtca ggatgtgagt actgctgtag cctggtatca acagaaacca   120
ggacaacctc ctaaattgct gatttactcg gcatcctacc ggttccctgg agtccctgat   180
cgcttcagcg gcagtggatc tgggacggat ttcactctca ccatcagcag tctgcaggct   240
gaagacgtgg cagtttatta ctgtcaccaa cattatttta ttccgtacac gtttggaggg   300
ggaaccaagc tggaaataaa acgg                                          324
```

<210> SEQ ID NO 13
<211> LENGTH: 107
<212> TYPE: PRT
<213> ORGANISM: Artificial Sequence
<220> FEATURE:
<223> OTHER INFORMATION: Synthetic Construct

<400> SEQUENCE: 13

```
Asp Ile Val Met Thr Gln Ser Pro Glu Ser Leu Ala Val Ser Leu Gly
 1               5                  10                  15

Glu Arg Ala Thr Ile Asn Cys Lys Ala Ser Gln Asp Val Ser Thr Ala
            20                  25                  30

Val Ala Tyr Gln Gln Lys Pro Gly Gln Pro Lys Leu Leu Ile Tyr
        35                  40                  45

Ser Ala Ser Tyr Arg Phe Pro Gly Val Pro Asp Arg Phe Ser Gly Ser
    50                  55                  60

Gly Ser Gly Met Tyr Phe Thr Leu Thr Ile Ser Ser Leu Gln Ala Glu
65                  70                  75                  80

Asp Val Ala Val Tyr Tyr Cys His Gln His Phe Ile Pro Tyr Thr
                85                  90                  95

Phe Gly Gly Gly Thr Met Leu Glu Ile Lys Arg
            100                 105
```

<210> SEQ ID NO 14
<211> LENGTH: 106
<212> TYPE: PRT
<213> ORGANISM: Artificial Sequence
<220> FEATURE:
<223> OTHER INFORMATION: Synthetic Construct

<400> SEQUENCE: 14

```
Asp Ile Val Met Thr Gln Ser Pro Asp Ser Leu Ala Val Ser Leu Gly
 1               5                  10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Lys Leu Lys Asn
            100                 105
```

```
<210> SEQ ID NO 15
<211> LENGTH: 108
<212> TYPE: PRT
<213> ORGANISM: Artificial Sequence
<220> FEATURE:
<223> OTHER INFORMATION: Synthetic Construct

<400> SEQUENCE: 15

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105

<210> SEQ ID NO 16
<211> LENGTH: 108
<212> TYPE: PRT
<213> ORGANISM: Artificial Sequence
<220> FEATURE:
<223> OTHER INFORMATION: Synthetic Construct

<400> SEQUENCE: 16

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Ser Phe Gly Gly Gly Thr Lys Leu Glu Ile Lys Arg
            100                 105

<210> SEQ ID NO 17
<211> LENGTH: 107
<212> TYPE: PRT
<213> ORGANISM: Artificial Sequence
<220> FEATURE:
<223> OTHER INFORMATION: Synthetic Construct

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Tyr Gln Gln Lys Pro Gly Gln Pro Pro Lys Leu Leu Ile Tyr
        35                  40                  45
```

Ser Ala Ser Tyr Arg Phe Pro Gly Val Pro Asp Arg Phe Ser Gly Ser
            50                  55                  60

Gly Ser Gly Thr Asp Phe Thr Leu Thr Ile Ser Ser Leu Gln Ala Glu
 65                  70                  75                  80

Asp Val Ala Val Tyr Tyr Gly His Gln His Tyr Phe Ile Pro Tyr Thr
                 85                  90                  95

Phe Gly Gly Gly Thr Lys Leu Glu Ile Lys Arg
            100                 105

<210> SEQ ID NO 18
<211> LENGTH: 108
<212> TYPE: PRT
<213> ORGANISM: Artificial Sequence
<220> FEATURE:
<223> OTHER INFORMATION: Synthetic Construct

<400> SEQUENCE: 18

Asp Ile Val Met Thr Gln Ser Pro Asp Ser Leu Ala Val Ser Leu Gly
 1               5                  10                  15

Glu Arg Ala Thr Ile Asn Cys Lys Ala Ser Gln Asp Val Ser Thr Ala
                 20                  25                  30

Val Ala Trp Tyr Gln Gln Lys Pro Gly Gln Pro Pro Lys Leu Leu Ile
             35                  40                  45

Tyr Ser Ala Ser Tyr Arg Phe Pro Gly Val Pro Asp Arg Phe Ser Gly
 50                  55                  60

Ser Gly Ser Gly Thr Asp Phe Thr Leu Thr Ile Ser Ser Leu Gln Ala
 65                  70                  75                  80

Gly Asp Val Ala Val Tyr Tyr Cys His Gln His Tyr Phe Ile Pro Tyr
                 85                  90                  95

Thr Phe Gly Gly Gly Thr Lys Leu Glu Ile Lys Arg
            100                 105

<210> SEQ ID NO 19
<211> LENGTH: 107
<212> TYPE: PRT
<213> ORGANISM: Artificial Sequence
<220> FEATURE:
<223> OTHER INFORMATION: Synthetic Construct

<400> SEQUENCE: 19

Asp Ile Val Met Thr Gln Ser Pro Asp Ser Leu Ala Val Ser Leu Gly
 1               5                  10                  15

Glu Arg Ala Thr Ile Asn Cys Lys Ala Ser Gln Asp Val Ser Thr Ala
                 20                  25                  30

Val Ala Trp Tyr Gln Gln Lys Pro Gly His Pro Pro Lys Leu Leu Ile
             35                  40                  45

Tyr Ser Ala Ser Tyr Arg Phe Pro Gly Val Pro Asp Arg Phe Ser Gly
 50                  55                  60

Ser Gly Ser Gly Thr Asp Phe Thr Leu Thr Ile Ser Ser Leu Gln Ala
 65                  70                  75                  80

Glu Asp Val Ala Val Tyr Tyr Gly His His Cys Phe Ile Pro Tyr Thr
                 85                  90                  95

Phe Gly Gly Gly Thr Lys Leu Glu Ile Lys Arg
            100                 105

<210> SEQ ID NO 20
<211> LENGTH: 108
<212> TYPE: PRT

```
<213> ORGANISM: Artificial Sequence
<220> FEATURE:
<223> OTHER INFORMATION: Synthetic Contstruct

<400> SEQUENCE: 20

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Asp Arg Phe Gly Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105

<210> SEQ ID NO 21
<211> LENGTH: 108
<212> TYPE: PRT
<213> ORGANISM: Artificial Sequence
<220> FEATURE:
<223> OTHER INFORMATION: Synthetic Construct

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Asn Leu Leu Ile
        35                  40                  45

Tyr Ser Ala Ser Tyr Arg Phe Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105

<210> SEQ ID NO 22
<211> LENGTH: 106
<212> TYPE: PRT
<213> ORGANISM: Artificial Sequence
<220> FEATURE:
<223> OTHER INFORMATION: Synthetic Construct

<400> SEQUENCE: 22

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Asp Arg Phe Ser Gly
    50                  55                  60
```

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Ser Trp Lys Asn
            100                 105

<210> SEQ ID NO 23
<211> LENGTH: 108
<212> TYPE: PRT
<213> ORGANISM: Artificial Sequence
<220> FEATURE:
<223> OTHER INFORMATION: Synthetic Construct

<400> SEQUENCE: 23

Asp Ile Val Met Thr Ser Leu Gln Thr Pro Trp Leu Cys Leu Trp Ala
1               5                   10                  15

Arg Gly Pro Thr Ile Asn Cys Lys Ala Ser Gln Gly Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105

<210> SEQ ID NO 24
<211> LENGTH: 108
<212> TYPE: PRT
<213> ORGANISM: Artificial Sequence
<220> FEATURE:
<223> OTHER INFORMATION: Synthetic Construct

<400> SEQUENCE: 24

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105

<210> SEQ ID NO 25
<211> LENGTH: 108
<212> TYPE: PRT
<213> ORGANISM: Artificial Sequence
<220> FEATURE:
<223> OTHER INFORMATION: Synthetic Construct

<400> SEQUENCE: 25

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105

<210> SEQ ID NO 26
<211> LENGTH: 108
<212> TYPE: PRT
<213> ORGANISM: Artificial Sequence
<220> FEATURE:
<223> OTHER INFORMATION: Synthetic Construct

<400> SEQUENCE: 26

Asp Ile Val Met Thr Gln Ser Pro Asp Ser Leu Ala Val Tyr Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Asp Arg Leu Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105

<210> SEQ ID NO 27
<211> LENGTH: 108
<212> TYPE: PRT
<213> ORGANISM: Artificial Sequence
<220> FEATURE:
<223> OTHER INFORMATION: Synthetic Construct

<400> SEQUENCE: 27

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

```
Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105
```

<210> SEQ ID NO 28
<211> LENGTH: 106
<212> TYPE: PRT
<213> ORGANISM: Artificial Sequence
<220> FEATURE:
<223> OTHER INFORMATION: Synthetic Construct

<400> SEQUENCE: 28

```
Asp Ile Val Met Thr Gln Ser Pro Asp Ser Leu Ala Val Ser Leu Gly
1               5                   10                  15

Glu Arg Ala Thr Ile Asn Cys Lys Ala Ser His Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Asp Arg Phe Ser Gly
    50                  55                  60

Ser Gly Ser Gly Thr Asp Phe Thr Leu Thr Ile Cys Ser Leu Gln Ala
65                  70                  75                  80

Glu Asp Val Ala Val Tyr Tyr Cys His Gln His Tyr Phe Ile Pro Tyr
                85                  90                  95

Thr Phe Glu Gly Glu Pro Ser Trp Lys Asn
            100                 105
```

<210> SEQ ID NO 29
<211> LENGTH: 107
<212> TYPE: PRT
<213> ORGANISM: Artificial Sequence
<220> FEATURE:
<223> OTHER INFORMATION: Synthetic Construct

<400> SEQUENCE: 29

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Val Pro Asp Arg Phe Ser Gly Ser
    50                  55                  60

Gly Ser Gly Thr Asp Phe Thr Leu Thr Ile Ser Ser Leu Gln Ala Glu
65                  70                  75                  80

Asp Val Ala Val Tyr Tyr Cys His Gln His Tyr Phe Ile Pro Tyr Thr
                85                  90                  95

Phe Gly Gly Gly Thr Lys Leu Glu Ile Lys Arg
            100                 105
```

<210> SEQ ID NO 30
<211> LENGTH: 108
<212> TYPE: PRT
<213> ORGANISM: Artificial Sequence
<220> FEATURE:
<223> OTHER INFORMATION: Synthetic Construct

<400> SEQUENCE: 30

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105
```

<210> SEQ ID NO 31
<211> LENGTH: 108
<212> TYPE: PRT
<213> ORGANISM: Artificial Sequence
<220> FEATURE:
<223> OTHER INFORMATION: Synthetic Construct

<400> SEQUENCE: 31

```
Asp Ile Val Met Thr Gln Ser Pro Asp Ser Leu Ala Met Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105
```

<210> SEQ ID NO 32
<211> LENGTH: 108
<212> TYPE: PRT
<213> ORGANISM: Artificial Sequence
<220> FEATURE:
<223> OTHER INFORMATION: Synthetic Construct

<400> SEQUENCE: 32

```
Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln His Pro Lys Leu Leu Ile
        35                  40                  45

Tyr Ser Ala Ser Tyr Arg Phe Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95
```

```
Thr Phe Gly Gly Gly Thr Lys Leu Glu Ile Lys Arg
            100                 105
```

```
<210> SEQ ID NO 33
<211> LENGTH: 108
<212> TYPE: PRT
<213> ORGANISM: Artificial Sequence
<220> FEATURE:
<223> OTHER INFORMATION: Synthetic Construct

<400> SEQUENCE: 33

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Glu Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105
```

```
<210> SEQ ID NO 34
<211> LENGTH: 108
<212> TYPE: PRT
<213> ORGANISM: Artificial Sequence
<220> FEATURE:
<223> OTHER INFORMATION: Synthetic Construct

<400> SEQUENCE: 34

Asp Ile Val Met Thr Gln Ser Pro Tyr Ser Leu Ala Val Ser Leu Gly
1               5                   10                  15

Glu Arg Ala Thr Ile Asn Cys Lys Ala Ser Gln Asp Val Ser Thr Ala
            20                  25                  30

Val Ala Trp Tyr Gln Gln Lys Pro Gly Gln Pro Pro Lys Leu Leu Ile
        35                  40                  45

Tyr Ser Ala Ser Tyr Arg Phe Pro Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105
```

```
<210> SEQ ID NO 35
<211> LENGTH: 107
<212> TYPE: PRT
<213> ORGANISM: Artificial Sequence
<220> FEATURE:
<223> OTHER INFORMATION: Synthetic Construct

<400> SEQUENCE: 35

Asp Ile Val Met Thr Gln Ser Pro Asp Ser Leu Ala Ala Ser Leu Gly
1               5                   10                  15
```

Glu Arg Ala Thr Ile Asn Cys Lys Ala Ser Gln Asp Val Ser Thr Ala
                    20                  25                  30

Val Ala Trp Tyr Gln Arg Lys Pro Gly Gln Pro Pro Lys Leu Leu Ile
            35                  40                  45

Tyr Ser Ala Ser Tyr Arg Phe Pro Gly Val Pro Asp Ser Phe Ser Gly
 50                  55                  60

Ser Gly Ser Gly Thr Asp Phe Thr Leu Thr Ile Ser Arg Leu Gln Ala
65                  70                  75                  80

Glu Asp Val Ala Val Tyr Cys His Gln His Tyr Phe Ile Pro Tyr Thr
                85                  90                  95

Phe Gly Gly Gly Thr Lys Leu Glu Ile Lys Arg
            100                 105

<210> SEQ ID NO 36
<211> LENGTH: 108
<212> TYPE: PRT
<213> ORGANISM: Artificial Sequence
<220> FEATURE:
<223> OTHER INFORMATION: Synthetic Construct

<400> SEQUENCE: 36

Phe Pro Gly Val Pro Asp Arg Phe Ser Gly Ser Gly Ser Gly Thr Asp
1               5                   10                  15

Phe Thr Leu Thr Ile Ser Ser Leu Gln Ala Glu Asp Val Ala Val Tyr
                20                  25                  30

Tyr Cys His Gln His Tyr Phe Ile Pro Tyr Thr Phe Gly Gly Gly Thr
            35                  40                  45

Lys Leu Glu Ile Lys Arg Phe Pro Gly Val Pro Asp Arg Phe Ser Gly
 50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys His Gln His Tyr Phe Ile Pro Tyr
                85                  90                  95

Thr Phe Gly Gly Gly Thr Lys Leu Glu Ile Lys Arg
            100                 105

<210> SEQ ID NO 37
<211> LENGTH: 118
<212> TYPE: PRT
<213> ORGANISM: Artificial Sequence
<220> FEATURE:
<223> OTHER INFORMATION: Synthetic Construct

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
                20                  25                  30

Gly Met Asp Trp Val Arg Gln Ala Pro Gly Gln Gly Leu Glu Trp Met
            35                  40                  45

Gly Arg Ile Asn Thr Tyr Thr Gly Glu Pro Thr Tyr Ala Asp Asp Phe
 50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Asp Gly Tyr Pro Phe Ala Tyr Trp Asp Gln Gly Thr
            100                 105                 110

Leu Val Thr Val Ser Ser
        115

<210> SEQ ID NO 38
<211> LENGTH: 118
<212> TYPE: PRT
<213> ORGANISM: Artificial Sequence
<220> FEATURE:
<223> OTHER INFORMATION: Synthetic Construct

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
            20                  25                  30

Gly Met Asp Trp Val Arg Gln Ala Pro Gly Gln Gly Leu Glu Trp Met
        35                  40                  45

Gly Arg Ile Asn Thr Tyr Thr Gly Glu Pro Ala Tyr Ala Asp Asp Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Val Asp Thr Ala Val Tyr Tyr Cys
                85                  90                  95

Ala Arg Arg Asp Gly Tyr Pro Phe Ala Tyr Trp Gly Gln Val Thr
            100                 105                 110

Leu Val Thr Val Ser Ser
        115

<210> SEQ ID NO 39
<211> LENGTH: 118
<212> TYPE: PRT
<213> ORGANISM: Artificial Sequence
<220> FEATURE:
<223> OTHER INFORMATION: Synthetic Construct

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
            20                  25                  30

Gly Met Asp Cys Val Arg Gln Ala Pro Gly Gln Gly Leu Glu Trp Met
        35                  40                  45

Gly Arg Ile Asn Thr Tyr Thr Gly Glu Pro Thr Tyr Ala Asp Asp Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Asp Gly Tyr Pro Phe Ala Tyr Trp Gly Gln Gly Thr
            100                 105                 110

Leu Val Thr Val Ser Ser
        115

<210> SEQ ID NO 40
<211> LENGTH: 118
<212> TYPE: PRT
<213> ORGANISM: Artificial Sequence
<220> FEATURE:
<223> OTHER INFORMATION: Synthetic Construct

<400> SEQUENCE: 40

```
Gln Val Gln Leu Val Gln Ser Gly Ala Glu Val Lys Lys Pro Gly Ala
1               5                   10                  15

Ser Val Lys Val Ser Cys Lys Ala Phe Gly Tyr Ala Phe Thr Lys Tyr
            20                  25                  30

Gly Met Asp Trp Val Arg Gln Ala Pro Gly Glu Gly Leu Glu Trp Met
        35                  40                  45

Gly Arg Ile Asn Thr Tyr Thr Gly Glu Pro Thr Tyr Ala Asp Asp Tyr
    50                  55                  60

Lys Gly Arg Val Thr Ile Thr Ala Asp Thr Ser Thr Ser Thr Ala Cys
65                  70                  75                  80

Met Glu Leu Ser Ser Leu Arg Ser Glu Asp Thr Ala Val Tyr Tyr Cys
                85                  90                  95

Ala Arg Arg Arg Asp Gly Tyr Pro Phe Ala Tyr Trp Gly Gln Gly Thr
            100                 105                 110

Leu Val Thr Val Ser Ser
        115
```

<210> SEQ ID NO 41
<211> LENGTH: 118
<212> TYPE: PRT
<213> ORGANISM: Artificial Sequence
<220> FEATURE:
<223> OTHER INFORMATION: Synthetic Construct

<400> SEQUENCE: 41

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
            20                  25                  30

Gly Met Asp Trp Val Arg Gln Ala Pro Gly Gln Gly Leu Glu Trp Met
        35                  40                  45

Gly Arg Ile Asn Thr Tyr Thr Gly Glu Pro Thr Tyr Ala Asp Asp Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Asp Gly Tyr Gln Phe Ala Tyr Trp Gly Gln Gly Thr
            100                 105                 110

Leu Val Thr Val Ser Ser
        115
```

<210> SEQ ID NO 42
<211> LENGTH: 118
<212> TYPE: PRT
<213> ORGANISM: Artificial Sequence
<220> FEATURE:
<223> OTHER INFORMATION: Synthetic Construct

<400> SEQUENCE: 42

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Ala Lys Tyr
            20                  25                  30

Gly Met Asp Trp Val Arg Gln Ala Pro Gly Gln Gly Leu Glu Trp Met
        35                  40                  45
```

```
Gly Arg Ile Asn Thr Tyr Thr Gly Glu Pro Tyr Thr Asp Asp Phe
            50                  55                  60

Lys Gly Arg Val Thr Ile Thr Ala Asp Thr Ser Ser Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Arg Arg Asp Gly Tyr Pro Phe Ala Phe Trp Gly Gln Gly Ser
                100                 105                 110

Leu Val Thr Val Ser Ser
            115

<210> SEQ ID NO 43
<211> LENGTH: 118
<212> TYPE: PRT
<213> ORGANISM: Artificial Sequence
<220> FEATURE:
<223> OTHER INFORMATION: Synthetic Construct

<400> SEQUENCE: 43

Gln Glu Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Lys Tyr
                20                  25                  30

Gly Met Asp Trp Val Arg Gln Ala Pro Gly Gln Gly Leu Glu Trp Met
            35                  40                  45

Gly Arg Ile Asn Thr Tyr Thr Gly Glu Pro Thr His Ala Asp Asp Phe
            50                  55                  60

Lys Gly Arg Val Thr Ile Thr Ala Asp Thr Ser Ser Ser Thr Ala Tyr
 65                  70                  75                  80

Met Glu Leu Ser Ser Leu Arg Ser Glu Asp Thr Ala Val Tyr Cys Cys
                85                  90                  95

Ala Arg Arg Arg Asp Gly Tyr Pro Phe Ala Tyr Arg Gly Gln Gly Thr
                100                 105                 110

Leu Val Thr Val Ser Ser
            115

<210> SEQ ID NO 44
<211> LENGTH: 117
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (85)..(85)
<223> OTHER INFORMATION: Xaa can be any naturally occurring amino acid

<400> SEQUENCE: 44

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Ala Phe Thr Lys Tyr
                20                  25                  30

Arg Met Asp Trp Val Arg Gln Ala Pro Gly Gln Gly Leu Glu Trp Met
            35                  40                  45

Gly Arg Ile Asn Thr Tyr Thr Gly Glu Gln His Met Leu Met Thr Ser
            50                  55                  60

Arg Asp Gly Ser Pro Ser Pro Leu Thr Arg Leu Arg Ala Leu Pro Ile
 65                  70                  75                  80
```

```
Trp Ser Cys Arg Xaa Ser Asp Leu Arg Thr Arg Leu Cys Lys Thr Val
                85                  90                  95

Gln Glu Asp Glu Met Val Thr Arg Leu Leu Thr Gly Ala Lys Gly Leu
            100                 105                 110

Trp Ser Pro Tyr Pro
        115

<210> SEQ ID NO 45
<211> LENGTH: 118
<212> TYPE: PRT
<213> ORGANISM: Artificial Sequence
<220> FEATURE:
<223> OTHER INFORMATION: Synthetic Construct

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
            20                  25                  30

Gly Met Asp Arg Val Arg Gln Ala Pro Gly Gln Gly Leu Gln Trp Met
        35                  40                  45

Gly Arg Ile Asn Thr Tyr Thr Gly Glu Pro Thr Tyr Ala Asp Asp Phe
    50                  55                  60

Lys Gly Arg Val Thr Ile Thr Ala Asp Thr Ser Thr Ser Thr Ala Tyr
65                  70                  75                  80

Met Glu Leu Thr Ser Leu Arg Ser Lys Asp Thr Ala Val Tyr Tyr Cys
                85                  90                  95

Ala Arg Arg Asp Gly Tyr Pro Phe Ala Tyr Trp Gly Gln Gly Ala
            100                 105                 110

Leu Val Thr Val Ser Ser
        115

<210> SEQ ID NO 46
<211> LENGTH: 118
<212> TYPE: PRT
<213> ORGANISM: Artificial Sequence
<220> FEATURE:
<223> OTHER INFORMATION: Synthetic Construct

<400> SEQUENCE: 46

Gln Val Gln Leu Met Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
            20                  25                  30

Gly Met Asp Trp Val Arg Gln Ala Pro Gly Gln Gly Leu Glu Trp Met
        35                  40                  45

Gly Arg Ile Asn Thr Tyr Thr Gly Glu Pro Thr Tyr Ala Asp Asp Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Tyr
                85                  90                  95

Ala Arg Arg Asp Gly Tyr Pro Leu Ala Tyr Trp Gly Gln Gly Thr
            100                 105                 110

Leu Val Thr Val Ser Ser
        115

<210> SEQ ID NO 47
```

<211> LENGTH: 118
<212> TYPE: PRT
<213> ORGANISM: Artificial Sequence
<220> FEATURE:
<223> OTHER INFORMATION: Synthetic Construct

<400> SEQUENCE: 47

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Ala Leu Thr Lys Tyr
            20                  25                  30
Gly Met Asp Trp Val Arg Gln Ala Pro Gly Gln Gly Leu Glu Trp Met
        35                  40                  45
Gly Arg Ile Asn Thr Tyr Thr Gly Glu Pro Thr Tyr Ala Asp Asp Phe
    50                  55                  60
Lys Gly Arg Val Thr Ile Thr Ala Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Arg Arg Gly Gly Tyr Pro Phe Ala Tyr Trp Gly Gln Gly Thr
            100                 105                 110
Leu Val Thr Val Ser Ser
            115

<210> SEQ ID NO 48
<211> LENGTH: 118
<212> TYPE: PRT
<213> ORGANISM: Artificial Sequence
<220> FEATURE:
<223> OTHER INFORMATION: Synthetic Construct

<400> SEQUENCE: 48

Gln Val Gln Leu Val Gln Ser Gly Ala Glu Val Lys Lys Pro Gly Ala
1               5                   10                  15
Ser Val Lys Val Ser Cys Lys Ala Pro Gly Tyr Ala Phe Thr Lys Tyr
            20                  25                  30
Gly Met Asp Trp Val Arg Gln Ala Pro Gly Gln Gly Leu Glu Trp Met
        35                  40                  45
Gly Arg Ile Asn Thr Tyr Thr Gly Glu Pro Thr Ser Ala Asp Asp Phe
    50                  55                  60
Lys Gly Arg Val Thr Ile Thr Ala Asp Thr Ser Thr Ser Thr Ser Tyr
65                  70                  75                  80
Met Glu Leu Ser Ser Leu Arg Ser Glu Asp Thr Ala Val Tyr Tyr Cys
                85                  90                  95
Ala Arg Arg Arg Asp Gly Tyr Pro Leu Ala Tyr Trp Gly Gln Gly Thr
            100                 105                 110
Leu Val Thr Val Ser Ser
            115

<210> SEQ ID NO 49
<211> LENGTH: 118
<212> TYPE: PRT
<213> ORGANISM: Artificial Sequence
<220> FEATURE:
<223> OTHER INFORMATION: Synthetic Construct

<400> SEQUENCE: 49

Gln Val Lys Leu Val Gln Ser Gly Ala Glu Val Lys Lys Ser Gly Ala
1               5                   10                  15

-continued

Ser Val Lys Val Ser Cys Lys Ala Ser Gly Tyr Ala Phe Thr Lys Tyr
            20                  25                  30

Gly Met Asp Trp Val Arg Gln Ala Pro Gly Gln Gly Leu Glu Trp Met
        35                  40                  45

Gly Arg Ile Asn Thr Tyr Thr Gly Glu Pro Thr Tyr Ala Asp Asp Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Asp Gly Tyr Pro Phe Ala Tyr Trp Gly Gln Gly Thr
            100                 105                 110

Leu Val Ser Val Ser Ser
        115

<210> SEQ ID NO 50
<211> LENGTH: 118
<212> TYPE: PRT
<213> ORGANISM: Artificial Sequence
<220> FEATURE:
<223> OTHER INFORMATION: Synthetic Construct

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
            20                  25                  30

Gly Met Asp Trp Val Arg Gln Ala Pro Gly Gln Gly Leu Glu Trp Met
        35                  40                  45

Gly Arg Ile Asn Thr Tyr Thr Gly Glu Pro Thr Tyr Ala Asp Asp Phe
    50                  55                  60

Lys Gly Arg Val Thr Ile Thr Ala Asp Thr Ser Ser Ser Thr Ala Tyr
65                  70                  75                  80

Met Glu Leu Ser Ser Leu Arg Ser Glu Gly Thr Ala Val Tyr Tyr Cys
                85                  90                  95

Ala Arg Arg Arg Asp Gly Tyr Pro Phe Ala Tyr Trp Gly Gln Gly Thr
            100                 105                 110

Leu Val Thr Val Ser Ser
        115

<210> SEQ ID NO 51
<211> LENGTH: 118
<212> TYPE: PRT
<213> ORGANISM: Artificial Sequence
<220> FEATURE:
<223> OTHER INFORMATION: Synthetic Construct

<400> SEQUENCE: 51

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
            20                  25                  30

Gly Met Asp Trp Val Arg Gln Ala Pro Gly Gln Gly Leu Glu Trp Met
        35                  40                  45

Gly Arg Ile Asn Thr Tyr Thr Gly Glu Pro Thr Tyr Ala Asp Asp Phe
    50                  55                  60

Lys Gly Arg Val Ala Ile Thr Ala Asp Thr Ser Thr Ser Ala Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Asp Gly Tyr Pro Phe Ala Tyr Trp Gly Gln Gly Thr
            100                 105                 110

Leu Val Thr Val Ser Ser
        115

<210> SEQ ID NO 52
<211> LENGTH: 118
<212> TYPE: PRT
<213> ORGANISM: Artificial Sequence
<220> FEATURE:
<223> OTHER INFORMATION: Synthetic Construct

<400> SEQUENCE: 52

Gln Val Gln Ser Val Gln Ser Gly Pro Glu Val Lys Lys Pro Gly Ala
1               5                   10                  15

Ser Val Lys Val Ser Cys Lys Ala Ser Gly Tyr Ala Phe Thr Lys Tyr
            20                  25                  30

Gly Met Asp Trp Val Arg Gln Ala Pro Gly Gln Gly Leu Glu Trp Met
        35                  40                  45

Gly Arg Ile Asn Thr Tyr Met Gly Glu Pro Thr Tyr Ala Asp Asp Phe
    50                  55                  60

Lys Gly Arg Val Thr Ile Thr Ala Gly Thr Ser Thr Ser Thr Ala Tyr
65                  70                  75                  80

Met Glu Leu Ser Ser Leu Arg Ser Glu Asp Thr Ala Val His Tyr Cys
                85                  90                  95

Ala Arg Arg Arg Asp Gly Tyr Pro Phe Ala Asn Trp Gly Gln Gly Thr
            100                 105                 110

Leu Val Thr Val Ser Ser
        115

<210> SEQ ID NO 53
<211> LENGTH: 118
<212> TYPE: PRT
<213> ORGANISM: Artificial Sequence
<220> FEATURE:
<223> OTHER INFORMATION: Synthetic Construct

<400> SEQUENCE: 53

Gln Val Gln Leu Val Gln Ser Gly Ala Glu Val Lys Lys Pro Gly Val
1               5                   10                  15

Ser Val Lys Val Ser Cys Lys Ala Ser Gly Tyr Ala Phe Thr Lys Tyr
            20                  25                  30

Gly Lys Asp Trp Val Arg Gln Ala Pro Gly Gln Gly Leu Glu Trp Met
        35                  40                  45

Gly Arg Ile Asn Thr Tyr Thr Gly Glu Pro Thr Tyr Val Asp Asp Phe
    50                  55                  60

Lys Gly Arg Val Ala Ile Thr Ala Asp Thr Ser Thr Ser Thr Ala Tyr
65                  70                  75                  80

Met Glu Leu Ser Tyr Leu Arg Ser Glu Asp Thr Ala Val Tyr Tyr Cys
                85                  90                  95

Ala Arg Arg Arg Asp Gly Tyr Pro Leu Ala His Trp Gly Lys Gly Thr
            100                 105                 110

Leu Val Thr Val Ser Ser
        115

```
<210> SEQ ID NO 54
<211> LENGTH: 118
<212> TYPE: PRT
<213> ORGANISM: Artificial Sequence
<220> FEATURE:
<223> OTHER INFORMATION: Synthetic Construct

<400> SEQUENCE: 54

Gln Val Gln Leu Ala Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
                20                  25                  30

Gly Met Asp Trp Val Arg Gln Ala Pro Gly Gln Gly Leu Glu Trp Met
            35                  40                  45

Gly Arg Ile Asn Thr Tyr Thr Gly Gly Pro Thr Tyr Ala Asp Asp Phe
        50                  55                  60

Lys Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Asp Gly Tyr Pro Val Ala Tyr Trp Gly Gln Gly Thr
            100                 105                 110

Leu Val Thr Val Ser Ser
        115

<210> SEQ ID NO 55
<211> LENGTH: 118
<212> TYPE: PRT
<213> ORGANISM: Artificial Sequence
<220> FEATURE:
<223> OTHER INFORMATION: Synthetic Construct

<400> SEQUENCE: 55

Gln Val Gln Leu Val Arg Ser Gly Ala Glu Val Lys Lys Pro Gly Ala
1               5                   10                  15

Ser Val Lys Val Ser Cys Lys Ala Ser Gly Phe Ala Phe Thr Lys Tyr
                20                  25                  30

Gly Met Asp Trp Val Arg Gln Ala Pro Gly Gln Gly Ser Glu Trp Leu
            35                  40                  45

Gly Arg Ile Asn Thr Tyr Thr Gly Glu Pro Thr Tyr Ala Asp Asp Ser
        50                  55                  60

Lys Gly Arg Val Thr Ile Thr Ala Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Asp Gly Tyr Pro Phe Ala Tyr Trp Gly Gln Gly Thr
            100                 105                 110

Leu Val Thr Val Ser Ser
        115

<210> SEQ ID NO 56
<211> LENGTH: 118
<212> TYPE: PRT
<213> ORGANISM: Artificial Sequence
<220> FEATURE:
<223> OTHER INFORMATION: Synthetic Construct

<400> SEQUENCE: 56

Gln Val Gln Leu Val Gln Ser Gly Ala Glu Val Lys Lys Pro Gly Ala
1               5                   10                  15
```

Ser Val Lys Val Ser Cys Lys Ala Ser Gly Tyr Ala Phe Thr Lys Tyr
            20                  25                  30

Gly Met Asp Trp Val Leu Gln Ala Pro Gly Gln Gly Leu Glu Trp Met
        35                  40                  45

Gly Arg Ile Asn Thr Tyr Thr Gly Glu Pro Thr Tyr Ala Asp Asp Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Lys Asp Thr Ala Val Tyr Tyr Cys
                85                  90                  95

Ala Arg Arg Asp Gly Tyr Pro Phe Ala Tyr Trp Gly Gln Gly Thr
            100                 105                 110

Leu Val Thr Val Ser Ser
        115

<210> SEQ ID NO 57
<211> LENGTH: 118
<212> TYPE: PRT
<213> ORGANISM: Artificial Sequence
<220> FEATURE:
<223> OTHER INFORMATION: Synthetic Construct

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
            20                  25                  30

Gly Met Asp Trp Val Arg Gln Ala Pro Gly Gln Gly Leu Glu Trp Arg
        35                  40                  45

Gly Arg Ile Asn Thr Tyr Thr Gly Glu Pro Thr Tyr Ala Asp Asn Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Ser
                85                  90                  95

Ala Arg Arg Asp Gly Tyr Pro Phe Ala Tyr Trp Gly Gln Gly Thr
            100                 105                 110

Leu Val Thr Val Ser Ser
        115

<210> SEQ ID NO 58
<211> LENGTH: 118
<212> TYPE: PRT
<213> ORGANISM: Artificial Sequence
<220> FEATURE:
<223> OTHER INFORMATION: Synthetic Construct

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
            20                  25                  30

Gly Met Asp Trp Val Arg Gln Ala Pro Gly Gln Gly Leu Glu Trp Met
        35                  40                  45

Gly Arg Ile Asn Thr Tyr Thr Gly Glu Pro Thr Tyr Ala Asp Asp Phe
    50                  55                  60

Lys Gly Arg Val Thr Ile Ser Ala Asp Thr Ser Thr Ser Thr Ala Tyr

```
            65                  70                  75                  80
Met Glu Leu Ser Ser Leu Arg Ser Glu Val Thr Ala Val Tyr Tyr Cys
                85                  90                  95

Ala Arg Arg Arg Asp Gly Tyr Pro Phe Ala Tyr Trp Gly Gln Gly Thr
            100                 105                 110

Leu Val Thr Val Ser Ser
        115

<210> SEQ ID NO 59
<211> LENGTH: 118
<212> TYPE: PRT
<213> ORGANISM: Artificial Sequence
<220> FEATURE:
<223> OTHER INFORMATION: Synthetic Construct

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
            20                  25                  30

Gly Met Asp Trp Val Arg Gln Ala Pro Gly Gln Gly Leu Glu Trp Lys
        35                  40                  45

Gly Arg Ile Asn Thr Tyr Thr Gly Glu Pro Thr Tyr Ala Asp Asp Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Val Gly Tyr Pro Phe Ala Tyr Trp Gly Gln Gly Thr
            100                 105                 110

Leu Val Thr Val Ser Ser
        115

<210> SEQ ID NO 60
<211> LENGTH: 118
<212> TYPE: PRT
<213> ORGANISM: Artificial Sequence
<220> FEATURE:
<223> OTHER INFORMATION: Synthetic Construct

<400> SEQUENCE: 60

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Lys Tyr
            20                  25                  30

Gly Met Asp Trp Val Arg Gln Ala Pro Gly Gln Gly Leu Glu Trp Met
        35                  40                  45

Gly Arg Ile Asn Thr Tyr Thr Gly Glu Pro Thr Phe Ala Asp Asp Phe
    50                  55                  60

Lys Gly Arg Val Thr Ile Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Asp Gly Tyr Pro Phe Ala Tyr Trp Gly Arg Gly Thr
            100                 105                 110

Leu Val Thr Val Ser Ser
        115
```

ANTI-CEP ANTIBODY OR FRAGMENT THEREOF

RELATED APPLICATION

This application claims priority from U.S. Provisional Application No. 61/980,958, filed Apr. 17, 2014, the subject matter of which is incorporated herein by reference in its entirety.

GOVERNMENT FUNDING

This invention was made with government support under Grant No. GM-21249, RES503219, awarded by The National Institutes of General Medicine Studies of the National Institutes of Health. The United States government has certain rights to the invention.

BACKGROUND

Angiogenesis plays a critical role in tumor progression, invasion and metastasis. It has become an attractive molecular target for chemotherapy. Anti-angiogenic tumor therapies focus on several regulatory and signaling molecules that control the process of formation and sprouting of new blood vessels. In particular, inhibition of vascular endothelial growth factor (VEGF) has shown antitumor activity in clinical settings, which results in starvation or apoptosis of tumor cells. An example is Bevacizumab (Avastin) which is a monoclonal antibody that specifically recognizes and binds to VEGF-A. Avastin is currently approved by the U.S. Food and Drug Administration (FDA) as a first or second line therapeutic agent for treatment of glioblastoma and colorectal cancers (CRC), both of which are highly vascularized tumors that depend primarily on angiogenesis. Although Avastin monotherapy has been proven effective for several indications such as recurrent glioblastoma, many newly diagnosed cancer patients with glioblastoma do not respond and Avastin failed to provide a survival advantage. The mechanism of intrinsic and required resistance to Avastin is not fully elucidated, clinical investigations have suggested that other VEGF family members, including placental growth factor (PlGF), VEGF-C, VEGF-D, and cytokine angiogenic factors (CAFs), may modulate sensitivity to anti-VEGF-A (Avastin) therapy and allow regrowth of tumor-associated vasculature. This is because Avastin blocks the main flow of blood, so tumors shrink at the beginning, but the tumors may then switch dependence to other related growth factors in search of blood. Additional examples of the complex refractory nature of VEGF to Avastin were discussed in a recent review. Thus, additional angiogenesis pathways must exist that compensate for and contribute to resistance that develops to anti-VEGF-A therapy.

One of such angiogenesis pathway involves 2-(α-carboxyethyl)pyrrole (CEP) protein derivatives that are generated by radical-induced oxidation of docosahexaenoate (DHA)-containing lipids. CEP levels are elevated in ocular tissues from patients with age-related macular degeneration, as well as in human melanoma. Our studies have shown that CEPs promote angiogenesis through a previously unknown pathway. CEPs activate proangiogenic responses in a Toll-like receptor 2 (TLR-2)-dependant manner that is independent of VEGF receptors.

SUMMARY

Embodiments described herein relate to an isolated anti-carboxyethylpyrrole (anti-CEP) antibody or antigen binding portion thereof, and the use of the anti-CEP antibody or antigen binding portion thereof in inhibiting CEP-induced angiogenesis in a subject in need thereof. The anti-CEP antibody or antigen binding portion includes a heavy chain variable region that includes three CDRs having at least 90% sequence identity to the three heavy chain CDRs of SEQ ID NO: 7, and a light chain variable region that includes three CDRs having at least 90% sequence identity to the three light chain CDRs of SEQ ID NO: 8. The anti-CEP antibody or antigen binding portion thereof of can have a binding affinity $K_D$ to CEP less than about 5 nM.

In some embodiments, the three heavy chain CDRs have the amino acid sequences of SEQ ID NO: 1, SEQ ID NO: 2, and SEQ ID NO: 3. In other embodiments, the three light chain CDRs have the amino acid sequences of SEQ ID NO: 4, SEQ ID NO: 5, and SEQ ID NO: 6.

In other embodiments, the anti-CEP antibody or antigen binding portion thereof can include a heavy chain variable region having at least 90% sequence identity to an amino acid sequence of SEQ ID NO: 9. In still other embodiments, the anti-CEP antibody or antigen binding portion thereof can include a light chain variable region having at least 90% sequence identity to an amino acid sequence of SEQ ID NO: 10.

The anti-CEP antibody or antigen binding portion thereof can be an IgG, F(ab)2, F(ab')2, F(ab), F(ab') fragment, or truncated antibody. The anti-CEP antibody or antigen binding portion can also be a humanized or chimeric antibody or antigen binding portion thereof.

Other embodiments, described herein relate to a method of inhibiting CEP-induced angiogenesis in a subject in need thereof by administering to the subject an isolated anti-CEP antibody or antigen binding portion thereof that specifically binds to CEP and inhibits CEP-induced angiogenesis in the. The isolated anti-CEP antibody or antigen binding portion thereof (i) comprises a heavy chain variable region that includes three CDRs having at least 90% sequence identity to the three heavy chain CDRs of SEQ ID NO: 7, and a light chain variable region that includes three CDRs having at least 90% sequence identity to the three light chain CDRs of SEQ ID NO: 8, or (ii) competitively inhibits binding of an isolated anti-CEP antibody or antigen binding portion thereof, which comprises a heavy chain variable region that includes three CDRs having at least 90% sequence identity to the three heavy chain CDRs of SEQ ID NO: 7, and a light chain variable region that includes three CDRs having at least 90% sequence identity to the three light chain CDRs of SEQ ID NO: 8.

In some embodiments, the anti-CEP antibody or antigen binding portion thereof can be administered to tissue to inhibit aberrant angiogenesis. In other embodiments, the anti-CEP antibody or antigen binding portion thereof can be administered to a tumor or cancer and inhibiting angiogenesis of the tumor or cancer.

BRIEF DESCRIPTION OF THE DRAWINGS

FIG. 1 illustrates identification of CDRs, H-CDR1, H-CDR2, and H-CDR3, in the variable regions of SEQ ID NO: 7 mumAb anti-CEP and CDRs, L-CDR1, L-CDR2, and L-CDR3, in the variable regions of SEQ ID NO: 8 mumAb anti-CEP.

FIG. 2 illustrates amino acid sequence alignment of mouse chimeric and humanized variable region SEQ ID NO: 7-10.

FIG. 3 illustrates nucleotide sequences of SEQ ID NOs: 11 and 12 humanized variable regions. Eight oligonucleotides were assembled to provide huVL; nine oligonucleotides were assembled to provide huVH. The sequence of the forward oligonucleotides are marked with a solid underline while the reverse ones are marked with a dashed underline. The overlapping segments are shown in boldface type and marked with a double underline.

FIG. 6 illustrates the results of an assay showing PCR products analyzed in a 1% agarose gel. Lane 1. DNA size ladder; Lane 2. PCR product of Clone 10 using primers VHfEcoRI and L2R2; Lane 3. Undigested plasmid extracted from Clone 10; Lanes 4-5. EcoRI digested plasmids extracted from Clones 10 and 19; Lane 6. PCR product of Clone 19 using primers VHfEcoRI and L2R2; Lane 7. Undigested plasmid extracted from Clone 19; Lane 8-9. XmnI digested plasmids extracted from Clones 10 and 19.

FIGS. 7(A-B) illustrate a schematic and plot showing affinity measurement using BIAcore. Left: The change in reflected light angle from the side of the chip opposite of the flow channel is detected according to the mass bound to the surface of the chip. Right: A typical sensorgram generated from the kinetics of an interaction.

FIGS. 8(A-B) illustrate a graph showing the results of screening of stable cell lines for expression of anti-CEP huAb/huFab by ELISA. Top: 192 individual clones expressing anti-CEP huAb. Bottom: 192 individual clones expressing anti-CEP huFab.

FIGS. 9(A-B) illustrate plots showing affinity measurements of anti-CEP munAb and huAb by BIAcore using single-cycle kinetic approach.

FIGS. 10(A-B) illustrate plots showing competitive ELISAs of CPP-HSA, CHP-BSA, EP-BSA, and OHdiA-BSA with respect to CEP-HSA. Top: anti-CEP mumAb (0.1 µg/mL). Bottom: anti-CEP huAb (1 µg/mL).

FIGS. 13(A-C) illustrate images and graphs showing CEP is endogenously expressed in human melanoma, which also shows excessive vascularization and inflammation (assessed by CD31 and CD68 staining, respectively), at levels elevated six-fold over normal human skin (FIG. 13A Left) as quantified normalized to normal skin (n=8) (FIG. 13A right). Administration of murine anti-CEP mAb, but not control IGg2a antibodies, to a murine melanoma allograft diminished progression and vascularization, and this effect was additive to that of the VEGF receptor (VEGFR) inhibitor AAL-993 (FIG. 13B left; tumour size on day 10 and right: quantification of vascular area n=4). The proangiogenic effect of CEP on human umbilical vein endothelial cells (HUVEC) is comparable to that of VEGF. However, CEP does not act through the VEGFR, but rather acts as a ligand for TLR2, apparently as a hetero-dimer with TLR1. CEP triggers MyD88-dependent GTP loading of Rac1 leading to stimulation of NFkB, but does not result in phosphorylation (activation) of VEGFR2 (FIG. 13C).

FIGS. 14(A-B) illustrate plots showing antitumor activity of anti-CEP antibody in LS174T colorectal cancer models (A) and glioblastoma tumor models (B) compared with Avastin and control vehicle. A: Mice were treated with anti-CEP antibody (100 µg in a total of 350 µl of PBS), Avastin (100 µg in a total of 350 µl of PBS) and PBS (350 µl) daily at 12 days after xenografts. The tumor sizes were measured by CT imaging using Carimas software. B: Mice were treated with anti-CEP antibody (100 µg in a total of 350 µl of PBS), Avastin (100 µg in a total of 350 µl of PBS) and PBS twice a week at 12 days after xenografts. The tumor sizes were measured by calipers. Arrows denote the day when treatment of anti-CEP, Avastin and PBS were initiated. Data were expressed as mean±SEM, n=5. Double asterisk (**) P<0.05.

FIGS. 15(A-I) illustrate images showing angiogenesis represented by immunofluorescence CD31 staining in LS174T tumors. Representative sections were taken from avastin, anti-CEp and vehicle treated LS174T tumors at the end of the experiment. Significant decreased CD31 staining and changes of vascular morphology between the treated group and the control group were observed.

FIG. 16 illustrates a plot showing tumor growth of U87-MG bearing nude mice in vivo treated with Avastin only started from day 6 and combination treatment (Avastin started at day 9 and anti-CEP started at day 27) to the end of the experiment. The tumor sizes were measured by calipers. Arrows denote the day when treatment of Avastin and anti-CEP were initiated. Data were expressed as mean±SEM, n=10. Double asterisk (**) P<0.05.

FIGS. 17(A-B) illustrate a plot and image showing in vivo uptake of $^{18}$F-FDG in LS174T colorectal tumors in PBS and anti-CEP treated animals. A: quantitative analysis of tumor uptake normalized to baseline scan at day 0. Data were expressed as mean±SEM, n=5. Double asterisk (**) P<0.05. B: representative PET images of $^{18}$F-FDG uptake in PBS and anti-CEP treated animals at day 7. Arrows denote location of the tumors.

FIGS. 18(A-B) illustrate a plot and image showing in vivo uptake of $^{18}$F-FMISO in LS174T colorectal tumors in PBS and anti-CEP treated animals. A: quantitative analysis of tumor uptake of $^{18}$F-FMISO normalized to baseline scan at day 0. Data were expressed as mean±SEM, n=5. Double asterisk () P<0.05. B: representative PET images of $^{18}$F-FMISO uptake in PBS and anti-CEP treated animals at day 2 after treatment. Arrows denote where tumors are normalized to baseline scan at day 0. Data were expressed as mean±SEM, n=5. Double asterisk () P<0.05.

DETAILED DESCRIPTION

Figure 4:
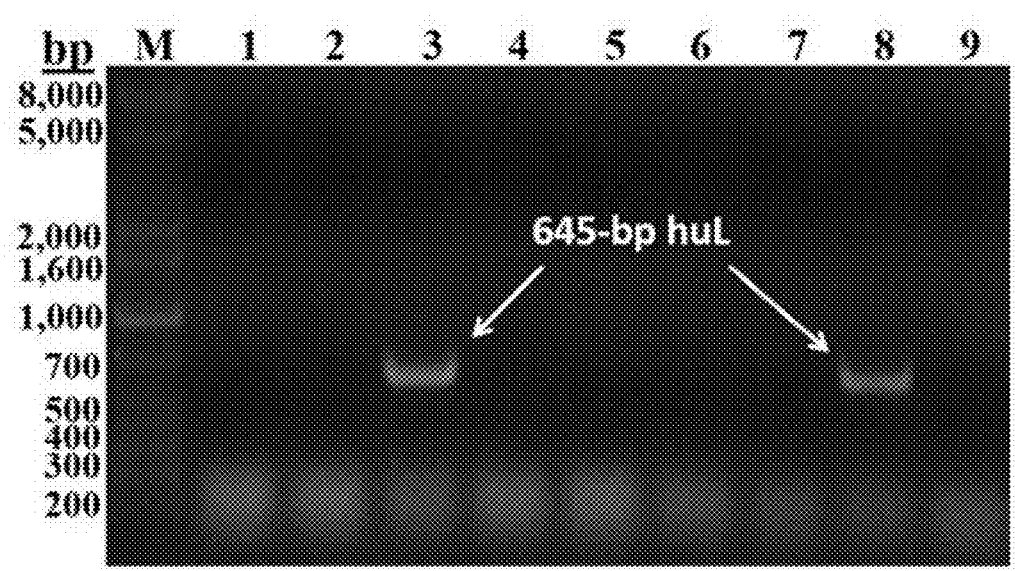
FIG. 4 illustrates the results of an assay showing PCR product analyzed in a 0.8% agarose gel for targeting positive clones with pFUSE2-huL by PCR. Lane 1. DNA size marker; Lanes 2-10. Randomly selected clones.

The term "acceptor human framework" refers to a framework comprising the amino acid sequence of a VL or VH framework derived from a human immunoglobulin framework, or from a human consensus framework.

The term "antibody" covers full length monoclonal antibodies, polyclonal antibodies, nanobodies and multi-specific antibodies. Biological antibodies are usually hetero-tetrameric glycoproteins of about 150,000 Daltons, composed of two identical light (L) chains and two identical heavy (H) chains. The two heavy chains are linked together by disulfide bonds, and each heavy chain is linked to a light chain by a disulfide bond. Each full-length IgG molecule contains at least two binding sites for a specific target or antigen. Light chains are either kappa or the lambda. Both light chains contain a domain of variable amino acid sequences, called the variable region (variously referred to as a "$V_L$," "$V_{kappa}$," or "$V_{lambda}$-region") and a domain of relatively conserved amino acid sequences, called the constant region ("CL-region"). Similarly, each heavy chain contains a variable region ("$V_H$-region") and three constant domains ("$C_{H1}$-," "$C_{H2}$-," and "$C_{H3}$-regions" and a hinge region.

The term "antibody fragment" refers to a segment of a full-length antibody, generally called as the target binding or variable region. Examples include Fab, Fab', F(ab')2 and Fv fragments. An "Fv" fragment is the minimum antibody fragment which contains a complete target recognition and binding site.

The term "antigen binding fragment" refers to a fragment or fragments of an antibody molecule that contain the antibody variable regions responsible for antigen binding. Fab, Fab', and F(ab)$_2$ lack the $F_C$ regions. Antigen-binding fragments can be prepared from full-length antibody by protease digestion. Antigen-binding fragments may be produced using standard recombinant DNA methodology by those skilled in the art.

The term complementarity-determining region ("CDR") refers to a specific region within variable regions of the heavy and the light chain. Generally, the variable region consists of four framework regions (FR1, FR2, FR3, FR4) and three CDRs arranged in the following manner: NH$_2$-FR1-CDR1-FR2-CDR2-FR3-CDR3-FR4-COOH. The term "framework regions" refers to those variable domain residues other than the CDR residues herein defined.

The term "competitively inhibits" refers to competitive inhibition of binding of an isolated antibody or antigen binding portion thereof to CEP by any other molecule.

The term "epitope" refers to a site on CEP to which antibody and fragments thereof bind and perform the functional activity. The term epitope is the same as "antigenic site", and "antibody binding site,". Both murine monoclonal anti-CEP antibody and the chimeric and humanized antibodies and the binding fragments thereof of the present invention share the same binding site.

The term "Fab fragment" refers to the constant domain of the light chain and the first constant domain of the heavy chain. Fab' fragments differ from Fab fragments by the few extra residues at the carboxyl terminus of the heavy chain CH1 domain including one or more cysteines from the antibody hinge region. F(ab') fragments are produced by cleavage of the disulfide bond at the hinge cysteines of the F(ab')$_2$pepsin digestion product.

The term "functional fragment" of an antibody refers to an antibody fragment having qualitative biological activity in common with a full-length antibody.

The term "human consensus framework" refers to a framework which represents the most commonly occurring amino acid residue in a selection of human immunoglobulin VL or VH framework sequences. Generally, the selection of human immunoglobulin VL or VH sequences is from a subgroup of variable domain sequences.

The term "humanized antibody" refers to an antibody consisting of mostly human sequences, except for CDR1, CDR2, and CDR3. All framework regions are also humanized. A chimeric antibody comprises murine CDRs, murine framework regions, and human constant regions. Collectively, chimeric antibodies contain murine both variable regions and human constant regions.

The term "identical" or "substantially identical" with respect to an antibody chain polypeptide sequence may be construed as an antibody chain exhibiting at least 65%, 70%, 80%, 90% or 95% sequence identity to the reference polypeptide sequence present in the variable region of the antigen binding fragment. The term with respect to a nucleic acid sequence may be construed as a sequence of nucleotides exhibiting at least about 65%, 75%, 85%, 90%, 95% or 97% sequence identity to the reference nucleic acid sequence.

The term "individual" refers to a vertebrate, preferably a mammal and more preferably a human.

The term "mammal" refers to any animal classified as a mammal includes humans, higher primates, domestic and farm animals, horses, pigs, cattle, dogs, cats and ferrets, etc. In one embodiment, the mammal is a human.

The term "monoclonal antibody" refers to a homogeneous population of antibodies. Such antibodies are highly specific and are directed against a single target antigen. These monoclonal antibodies are homogeneously produced by the hybridoma culture, uncontaminated by other immunoglobulins. Monoclonal antibodies can also be produced by other procedures such as phase display by well known methods.

The terms "patient", "mammalian host", "subject", and the like are used interchangeably herein, and refer to mammals, including human and veterinary subjects.

The terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease or at risk of acquiring the disease but has not yet been diagnosed as having it; (b) inhibiting the disease, i.e., arresting its development; and (c) relieving the disease, i.e., causing regression of the disease.

The term "knockout" refers to the technique in which a specific gene(s) are removed from a target animal. This technique is usually applied to rodents in which the gene of interest is removed via homologous recombination of an empty vector with the native animal chromosome. The technique works by swapping the animal's chromosome containing the gene with the empty vector containing a marker or random DNA sequences. This method results in an animal that is deficient of the gene of interest. The present invention would utilize this technique to generate antibodies against an antigen that is removed from the animal's genome to enhance generation of antibodies.

It is to be understood that this invention is not limited to particular embodiments described, as such may, of course, vary. It is also to be understood that the terminology used herein is for describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are encompassed within the invention, subject to any specifically excluded limit in the stated range. Where the stated range includes one or both of the limits, ranges excluding either or both of those included limits are also included in the invention.

Embodiments described herein relate to anti-carboxyethylpyrrole (anti-CEP) antibodies and antigen binding portions thereof and to their use in inhibiting CEP induced angiogenesis. The anti-CEP antibodies or antigen binding portions thereof can be used alone or in combination with other therapeutic agent to inhibit angiogenesis and/or to treat diseases and/or disorders associated with aberrant angiogenesis.

In some embodiments, the aberrant angiogenesis can be associated with tumor or cancer proliferation and the anti-CEP antibodies or antigen binding portions thereof can be administered alone or in combination with other therapeutic agents, such as VEGF inhibitors, to treat a tumor or cancer in a subject in need thereof. It was found that CEP is endogenously expressed in human cancers, which also shows excessive vascularization and inflammation. Administration of a humanized anti-CEP mAb described herein, but not control IGg2a antibodies, to a cancer allograft, such as a melanoma, colorectal cancer, or glioblastoma allograft, was found to diminish progression and vascularization of the cancer. This effect was found to be additive to that of a VEGF receptor (VEGFR) inhibitor.

In some embodiments, the anti-CEP antibodies or antigen binding portions thereof can include a heavy chain variable region that includes three CDRs having at least 90%, 95%, 96%, 97%, 98% or 99% sequence identity to the three heavy chain CDRs of SEQ ID NO: 7, and a light chain variable region that includes three CDRs having at least 90%, 95%, 96%, 97%, 98% or 99% sequence identity to the three light chain CDRs of SEQ ID NO: 8. The anti-CEP antibody or antigen binding portion thereof can have a binding affinity ($K_D$) to CEP less than about 5 nM, less than about 4 nM, less than about 3 nM, or less than about 2 nM.

In some embodiments, the three heavy chain CDRs have the amino acid sequences of SEQ ID NO: 1, SEQ ID NO: 2, and SEQ ID NO: 3. In other embodiments, the three light chain CDRs have the amino acid sequences of SEQ ID NO: 4, SEQ ID NO: 5, and SEQ ID NO: 6.

The anti-CEP antibodies or antigen binding portions thereof can also include antibodies or antigen binding portions thereof that bind to the same epitope on CEP as an anti-CEP antibody or antigen binding portion thereof, which comprises a heavy chain variable region that includes three CDRs having at least 90%, 95%, 96%, 97%, 98% or 99% sequence identity to the three heavy chain CDRs of SEQ ID NO: 7, and a light chain variable region that includes three CDRs having at least 90%, 95%, 96%, 97%, 98% or 99% sequence identity to the three light chain CDRs of SEQ ID NO: 8. Such antibodies can be identified based on their ability to cross-compete with or competitively inhibit binding of an isolated anti-CEP antibody or antigen binding portion thereof, which comprises a heavy chain variable region that includes three CDRs having at least 90%, 95%, 96%, 97%, 98% or 99% sequence identity to the three heavy chain CDRs of SEQ ID NO: 7, and a light chain variable region that includes three CDRs having at least 90%, 95%, 96%, 97%, 98% or 99% sequence identity to the three light chain CDRs of SEQ ID NO: 8. The ability of a test antibody to inhibit the binding of an anti-CEP antibody or antigen binding portion thereof described herein demonstrates that the test antibody can compete with an anti-CEP antibody or antigen binding portion thereof described herein for binding to CEP and thus binds to the same epitope on CEP. In some embodiments, the antibody that binds to the same epitope on human CEP as an anti-CEP antibody or antigen binding portion thereof, described herein, is a human monoclonal antibody. Such human monoclonal antibodies can be prepared and isolated as described in the Examples.

In other embodiments, an antibody can include heavy and light chain variable domains or regions comprising amino acid sequences that are substantially identical or homologous to the amino acid sequences of the preferred antibodies described herein, and wherein the antibodies retain the desired functional properties of the anti-CEP antibodies described herein. For example, the isolated monoclonal antibody, or antigen binding portion thereof can include a heavy chain variable region, which comprises an amino acid sequence that is at least 90%, 95%, 96%, 97%, 98% or 99% identical to the amino acid sequence of SEQ ID NO: 9; and/or a light chain variable region, which comprises an amino acid sequence that is at least 90%, 95%, 96%, 97%, 98% or 99% identical to the amino acid sequence of SEQ ID NO: 10.

An antibody having $V_H$ and $V_L$ regions having high (i.e., 90% or greater) homology to the $V_H$ and $V_L$ regions of the sequences set forth above, can be obtained by mutagenesis (e.g., site-directed or PCR-mediated mutagenesis) of nucleic acid molecules encoding the $V_H$ and $V_L$ regions of the sequences described herein, followed by testing of the encoded altered antibody for retained function (i.e., the functions set forth in (c) and (d) above) using the functional assays described herein.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

In certain aspects, an antibody of the invention can include a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on an antibody having the $V_H$ of SEQ ID NO: 7 or SEQ ID NO: 9 and $V_L$ sequences of SEQ ID NO: 8 or SEQ ID NO: 10.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth in (c) through (j) above) using the functional assays described herein.

An antibody described herein further can be prepared using an antibody having one or more of the $V_H$ and/or $V_L$ sequences disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties. Accordingly, other embodiments pertain to an isolated monoclonal antibody, or antigen binding portion thereof, comprising a heavy chain variable region comprising CDR1, CDR2, and CDR3 having, respectively, SEQ ID NO: 1, SEQ ID NO: 2, and SEQ ID NO: 3 and a light chain variable region comprising CDR1, CDR2, and CDR3 having, respectively, SEQ ID NO: 4, SEQ ID NO: 5, and SEQ ID NO: 6.

Another type of variable region modification is to mutate amino acid residues within the $V_H$ and/or $V_K$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) are introduced. The mutations may be amino acid substitutions, additions or deletions, but are preferably substitutions. Moreover, typically no more than one, two, three, four or five residues within a CDR region are altered.

Humanization and Display Technologies

There are advantages to producing antibodies with reduced immunogenicity. To a degree, this can be accomplished in connection with techniques of humanization and display techniques using appropriate libraries. It will be appreciated that murine antibodies or antibodies from other species can be humanized or primatized using techniques well known in the art.

Antibody fragments, such as Fv, F(ab')$_2$ and Fab may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Further, human antibodies or antibodies from other species can be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art.

Design and Generation of Other Therapeutics

Other therapeutic modalities beyond antibody moieties can be facilitated. Such modalities include, without limitation, advanced antibody therapeutics, such as bispecific antibodies, immunotoxins, and radiolabeled therapeutics, generation of peptide therapeutics, gene therapies, particularly intrabodies, antisense therapeutics, and small molecules.

Bispecific antibodies can be generated that comprise (i) two antibodies one with a specificity to CEP and another to a second molecule that are conjugated together, (ii) a single antibody that has one chain specific to CEP and a second chain specific to a second molecule, or (iii) a single chain antibody that has specificity to CEP and the other molecule. Such bispecific antibodies can be generated using techniques that are well known for example, in connection with (i) and (ii) (Fanger, M. W., R. F. Graziano, and P. M. Guyre, *Production and use of anti-FcR bispecific antibodies*. Immunomethods, 1994. 4(1): p. 72-81) and in connection with (iii) (Traunecker, A., A. Lanzavecchia, and K. Karjalainen, *Janusin: new molecular design for bispecific reagents*. Int J Cancer Suppl, 1992. 7: p. 51-2). Bispecific antibodies prepared in accordance with the foregoing would be likely to kill cells expressing CEP and particularly those cells in which the anti-CEP antibodies of the invention are effective.

Therapeutic Administration and Formulations

It will be appreciated that the anti-CEP antibodies or antigen binding portions thereof can be administered with suitable carriers, excipients, and other agents that are incorporated into formulations to provide improved transfer, delivery, tolerance, and the like. These formulations include, for example, powders, pastes, ointments, jellies, waxes, oils, lipids, lipid (cationic or anionic) containing vesicles (such as LIPFECTIN), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present invention, if the active ingredient in the formulation is not inactivated by the formulation and the formulation is physiologically compatible and tolerable with the route of administration.

Preparation of Antibodies

Anti-CEP antibodies or antigen binding portions thereof can be prepared in mouse using standard methods well known in the art. The monoclonal antibody can be converted into a humanized version for therapeutic use. The antibody can be made by contract or in house into humanized, fully human, chimeric, recombinant for therapeutic use. The hybridoma cell lines can be readily generated by those of ordinary skill in the art, given the guidance provided herein. The antibodies produced by the subject cell lines do not generate an adverse response. Adverse response is defined as an unwanted response.

Antibodies described herein can be expressed in cell lines other than hybridoma cell lines. Mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines.

Antibodies described herein can also be generated using knockout mice, rodents to generate effective blocking antibodies. The benefit of using a knockout rodent allows for increased probability for the generation of an antibody that is anti-rat, anti-mouse and anti-any other species, depending on the rodent being used, the potential for generating antibodies that are chimeric or human are easier to generate. Several therapeutic antibodies have been generated using xenomouse models to generate antibodies in mice that are chimeric or fully human (Davis, C. G., M. L. Gallo, and J. R. Corvalan, *Transgenic mice as a source of fully human antibodies for the treatment of cancer*. Cancer Metastasis Rev, 1999. 18(4): p. 421-5; Green, L. L., *Antibody engineering via genetic engineering of the mouse: XenoMouse strains are a vehicle for the facile generation of therapeutic human monoclonal antibodies*. J Immunol Methods, 1999. 231(1-2): p. 11-23; Wells, W. A., *Eek, a XenoMouse: Abgenix, Inc*. Chem Biol, 2000. 7(8): p. R185-6).

The heavy and light chain variable regions of chimeric or humanized antibodies can be linked to at least a portion of a human constant region by various well-known methods (see, e.g., Queen et al., 1989, *Proc. Natl. Acad. Sci. U.S.A.* 86:10029-10033 and WO 90/07861; these references and references cited therein are herein incorporated by reference for all purposes). The choice of constant region depends, in part, whether antibody-dependent complement and/or cellular mediated toxicity is desired. For example, isotypes $IgG_1$ and $IgG_3$ usually have greater complement binding activity than isotypes $IgG_2$ or $IgG_4$. Choice of isotype can also affect passage of antibody into the brain. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

For some applications, non-IgG antibodies can be useful. For example, where multivalent antibody complexes are desired, IgM and IgA antibodies can be used.

Chimeric and humanized antibodies are typically produced by recombinant expression. Recombinant polynucleotide constructs typically include an expression control sequence operably linked to the coding sequences of antibody chains, including naturally-associated or heterologous promoter regions. The expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, FROM GENES TO CLONES, (VCH Publishers, N Y, 1987). A number of suitable host cell lines capable of secreting intact heterologous proteins have been developed in the art, and include CHO cell lines, various COS cell lines, HeLa cells, L cells and myeloma cell lines. Preferably, the cells are nonhuman. Expression vectors for these cells can include expression control sequences, such as an origin of replication, a promoter, an enhancer (Queen et al., 1986, *Immunol. Rev.* 89:49), and necessary processing information sites, such as ribosome binding sites, RNA splice sites, polyadenylation sites, and transcriptional terminator sequences.

Alternatively, antibody coding sequences can be incorporated in transgenes for introduction into the genome of a transgenic animal and subsequent expression in the milk of the transgenic animal (see, e.g., U.S. Pat. Nos. 5,741,957, 5,304,489, 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures of the art, including HPLC purification, column chromatography, gel electrophoresis and the like (see generally, Scopes, *Protein Purification* (Springer-Verlag, N Y, 1982)).

Single cell PCR may be used in an attempt to retain the native pairing of $V_L$ and $V_H$ in the single cell. In this case antibody-producing B-lymphocytes which have been isolated from animals or humans may be fixed with a fixative solution or a solution containing a chemical such as formaldehyde, glutaraldehyde or the like. The cells are then permeabilized with a permeabilization solution comprising for example a detergent such as Brij, Tween, polysorbate, Triton X-100, or the like. The fixing and permeabilization process should provide sufficient porosity to allow entrance of enzymes, nucleotides and other reagents into the cells without undue destruction of cellular compartments or nucleic acids therein. Addition of enzymes and nucleotides may then enter the cells to reverse transcribe cellular $V_H$ and $V_L$ mRNA into the corresponding cDNA sequences.

Upon reverse transcription, the resulting cDNA sequences may be amplified by PCR using primers specific for immunoglobulin genes and, in particular, for the terminal regions of the $V_H$ and $V_L$ nucleic acids. PCR procedures may be followed as disclosed in, e.g., U.S. Pat. No. 4,683,195. Preferably, the cDNAs are PCR amplified and linked in the same reaction, using, in addition to the cDNA primers, one primer for the 5' end of the $V_H$ region gene and another for the 5' end of the $V_L$ gene. These primers also contain complementary tails of extra sequence, to allow the self-assembly of the $V_H$ and $V_L$ genes. After PCR amplification and linking, the chance of getting mixed products, in other words, mixed variable regions, is minimal because the amplification and linking reactions were performed within each cell. The amplified sequences are linked by hybridization of complementary terminal sequences. After linking, sequences may be recovered from cells. For example, after linking, cells can be washed in a solution of sodium dodecyl sulfate (SDS). The SDS precipitates out of the cells after incubation on ice and the supernatant can be electrophoresed into an agarose or acrylamide gel. Alternatively, or in combination with the SDS process, using a reagent such as digoxigenin-linked nucleotides, DNA products synthesized will remain within the cell and be amplified. The linked product is recovered upon electrophoresis of the supernatant.

After electrophoresis of the supernatant, the gel slice corresponding to the appropriate molecular weight of the linked product is removed and the DNA isolated on, for example, silica beads. The recovered DNA can be PCR amplified using terminal primers, if necessary, and cloned into vectors which may be plasmids, phages, cosmids, phagamids, viral vectors or combinations thereof. Convenient restriction enzyme sites may be incorporated into the hybridized sequences to facilitate cloning. These vectors may also be saved as a library of linked variable regions for later use.

The linked $V_H$ and $V_L$ region genes may be PCR amplified a second time using terminal nested primers, yielding a population of DNA fragments, which encode the linked $V_H$ and $V_L$ genetic regions. The grouping of $V_H$ and $V_L$ combinations is an advantage of this process and allows for the in mass or batch transfer of all clones and all DNA fragments during this and all cloning procedures.

The recombinant antibody may be generated under such conditions that the immunoglobulin heavy chain variable region and light chain variable region gene segments are linked together in a head-to head orientation, in order to allow for the bulk transfer of variable region light chain and heavy chain pairs from one vector to another, including from phage to vector, and including from the cell of origin to phage or vector, resulting in a stable pairing of specific immunoglobulin variable region light chain and heavy chains gene segments as they are found in the original polyclonal immune response of the animal or human individual.

It may sometimes be desirable to treat the variable region gene sequences with a mutating agent. Mutating agents create point mutations, gaps, deletions or additions in the genetic sequence which may be general or specific, or random or site directed. Useful mutating agents include ultraviolet light, gamma irradiation, chemicals such as ethidium bromide, psoralen and nucleic acid analogs, or DNA modifying enzymes such as restriction enzymes, transferases, ligases and specific and nonspecific nucleases and polymerases. Moreover, it may be feasible to use mutator strains. In particular, random mutations may be introduced in the CDRs of the $V_H$ and $V_L$ region genes by oligonucleotide directed mutagenesis. Mutations introduced into the gene sequence will ultimately increase library complexity and diversity as well as affinity for antigen which may further increase the library's usefulness in treatment. Furthermore, such mutagenesis may be used on a single $V_H$ and $V_L$ pair or on a defined group of such pairs to generate a library de novo.

Vectors are transformed into suitable host cells and the cultures amplified to expand the different populations of vectors that comprise the library. Host cells for prokaryotic vectors may be a culture of bacteria such as *Escherichia coli*. Host cells for eukaryotic vectors may be a culture of eukaryotic cells such as any mammalian, insect or yeast cell lines adapted to tissue culture. Bacterial cells are transformed with vectors by calcium chloride-heat shock or electroporation, although many other transformation procedures would also be acceptable. Eukaryotic cells are transfected with calcium phosphate precipitation or electroporation, although many other transformation procedures would also be acceptable. The DNA fragments may be cloned into prokaryotic or eukaryotic expression vectors, chimeric vectors or dual vectors. The expression vector may be a plasmid, cosmid, phage, viral vector, phagemid and combinations thereof, but is preferably a phage display vector wherein the recombinant product is expressed on the phage surface to facilitate screening and selection. Useful transcriptional and translational sites may be placed on the expression vector including RNA polymerase recognition regions such as a TATA box site, a CAT site, an enhancer, appropriate splicing sites, if necessary, a AT rich terminal region and a transcription initiation site. Useful sites to facilitate translation include translational start and stop sites and ribosome binding sites. Typically, some of the more useful sites for efficient eukaryotic expression, such as the SV40, CMV, HSV or baculovirus promoter/enhancer region, are derived from viruses. The resulting recombinant antibody may be of the murine class $IgG_1$, $IgG_{2a}$, $IgG_{2b}$, IgM, IgA, IgD or IgE, the human classes $IgG_1$, $IgG_2$, $IgG_3$, $IgG_4$, IgM, $IgA_1$, $IgA_2$, IgD or IgE, or combinations or fragments thereof. The chimeric antibody or humanized antibody library is composed of primarily IgG antibodies or Fab antibody fragments.

Pharmaceutical Compositions

The anti-CEP antibody or antigen binding portions thereof can be administered to an individual in a formulation with a pharmaceutically acceptable excipient(s). A wide variety of pharmaceutically acceptable excipients are known in the art and need not be discussed in detail herein.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The anti-CEP antibodies or antigen binding portions thereof may be administered to the subject using any convenient means capable of resulting in the desired therapeutic effect. The antibody can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of a subject antibody can be achieved in various ways, including oral, buccal, rectal, parenteral, intraperitoneal, intradermal, subcutaneous, intramuscular, transdermal, intranasal, pulmonary, intratracheal, etc., administration.

In pharmaceutical dosage forms, the antibodies may be administered in the form of their pharmaceutically acceptable salts, or they may also be used alone or in appropriate association, as well as in combination, with other pharmaceutically active compounds. The following methods and excipients are merely exemplary and are in no way limiting.

The anti-CEP antibody or antigen binding portion thereof can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of a subject antibody calculated in an amount sufficient to produce the desired effect in association with a pharmaceutically acceptable diluent, carrier or vehicle.

Treatment Methods

The anti-CEP antibody or antigen binding portion thereof can be used to treat CEP induced angiogenesis including pathological angiogenesis in a subject in need thereof. Depending upon the type and severity of the pathological angiogenesis, the anti-CEP antibody or antigen binding portion thereof can be prepared as a pharmaceutical or therapeutic composition and then administered to the subject via an appropriate route. Upon administration to the subject, the anti-CEP antibody or antigen binding portion thereof can substantially inhibit complexing of TLR2 with CEP adducts in endothelial cells. In the absence of TLR2 and CEP adduct complexing, the TLR2 signaling pathway will not be activated and, in turn, will not lead to integrin expression by endothelial cells. Without an activated TLR2 signaling pathway, endothelial cells will not proliferate into the surrounding matrix to form solid sprouts connecting neighboring vessels. Consequently, pathological angiogenesis will be substantially prevented or inhibited in the subject.

In accordance with another embodiment, the anti-CEP antibody or antigen binding portion thereof may be used to treat animals and patients with aberrant angiogenesis, such as angiogenesis contributing to a variety of diseases and disorders. The most prevalent and/or clinically important of these, outside the field of cancer treatment, includes arthritis, rheumatoid arthritis, psoriasis, atherosclerosis, diabetic retinopathy, age-related macular degeneration, Grave's disease, vascular restenosis, including restenosis following angioplasty, arteriovenous malformations (AVM), meningioma, hemangioma and neovascular glaucoma. Other potential targets for intervention include angiofibroma, atherosclerotic plaques, corneal graft neovascularization, hemophilic joints, hypertrophic scars, osler-weber syndrome, pyogenic granuloma retrolental fibroplasia, scleroderma, trachoma, vascular adhesions, synovitis, dermatitis, various other inflammatory diseases and disorders, and even endometriosis. Further diseases and disorders that are treatable by the composition described, and the unifying basis of such angiogenic disorders, are set forth below.

One disease in which angiogenesis is involved is rheumatoid arthritis, wherein the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Factors associated with angiogenesis also have a role in osteoarthritis, contributing to the destruction of the joint.

Another example of a disease mediated by angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of choroidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia.

Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

Other diseases include, but are not limited to, diseases associated with rubeosis and diseases caused by the abnormal proliferation of fibrovascular or fibrous tissue including all forms of proliferative vitreoretinopathy.

Chronic inflammation also involves pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells.

Another pathological role associated with angiogenesis is found in atherosclerosis. The plaques formed within the lumen of blood vessels have been shown to have angiogenic stipulatory activity. This application provides an effective treatment for such conditions.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Diseases and disorders characterized by undesirable vascular permeability can also be treated by the compositions described herein. These include edema associated with brain tumors, ascites associated with malignancies, Meigs' syndrome, lung inflammation, nephrotic syndrome, pericardial effusion and pleural effusion, as disclosed in WO 98/16551, specifically incorporated herein by reference.

Each of the foregoing diseases and disorders, along with all types of tumors, as described in the following sections, can be effectively treated by the antibodies described herein in accordance with the knowledge in the art, as disclosed in, e.g., U.S. Pat. No. 5,712,291 (specifically incorporated herein by reference), that unified benefits result from the application of anti-angiogenic strategies to the treatment of angiogenic diseases.

The anti-CEP antibody or antigen binding portion thereof can also be utilized in the treatment of neoplastic disorders, such as tumors or cancers. Tumors in which angiogenesis is important include malignant tumors, and benign tumors, such as acoustic neuroma, neurofibroma, trachoma and pyogenic granulomas. Angiogenesis is particularly prominent in solid tumor formation and metastasis. However, angiogenesis is also associated with blood-born tumors, such as leukemias, and various acute or chronic neoplastic diseases of the bone marrow in which unrestrained proliferation of white blood cells occurs, usually accompanied by anemia, impaired blood clotting, and enlargement of the lymph nodes, liver, and spleen. Angiogenesis also plays a role in the abnormalities in the bone marrow that give rise to leukemia-like tumors.

Angiogenesis is important in two stages of tumor metastasis. In the vascularization of the primary tumor, angiogenesis allows cells to enter the blood stream and to circulate throughout the body. After tumor cells have left the primary site, and have settled into the secondary, metastasis site, angiogenesis must occur before the new tumor can grow and expand. Therefore, prevention of angiogenesis can prevent metastasis of tumors and contain the neoplastic growth at the primary site, allowing treatment by other therapeutics, particularly, therapeutic agent-targeting agent constructs.

The anti-CEP antibody or antigen binding portion thereof described herein are thus broadly applicable to the treatment of any malignant tumor having a vascular component. In using the antibodies described herein in the treatment of tumors, particularly vascularized, malignant tumors, the antibodies may be used alone or in combination with, e.g., chemotherapeutic, radiotherapeutic, apoptopic, anti-angiogenic agents and/or immunotoxins or coaguligands.

Typical vascularized tumors for treatment are the solid tumors, particularly carcinomas, which require a vascular component for the provision of oxygen and nutrients. Exemplary solid tumors that may be treated include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, and the like. WO 98/45331 is also incorporated herein by reference to further exemplify the variety of tumor types that may be effectively treated using the anti-CEP antibody or antigen binding portion thereof.

Knowledge of the role of angiogenesis in the maintenance and metastasis of tumors has led to a prognostic indicator for cancers, such as breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by the therapies described herein will reduce or negate the recurrence of such tumors.

The antibodies described herein can also be used in the treatment of any patient that presents with a solid tumor. In light of the specific properties of the anti-CEP antibody or antigen binding portion thereof, the therapeutics described herein will have reduced side effects. Particular advantages will result in the maintenance or enhancement of host immune responses against the tumor, as mediated by macrophages, and in the lack of adverse effects on bone tissue. The compositions will thus be the anti-angiogenic therapy of choice for the treatment of pediatric cancers and patients having, or at risk for developing, osteoporosis and other bone deficiencies.

Although all malignancies and solid tumors may be treated by the antibodies described herein, the anti-CEP antibody or antigen binding portion thereof is particularly contemplated for use in treating patients with more angiogenic tumors, or patients at risk for metastasis.

The antibodies and methods described herein also intended as a preventative or prophylactic treatment. These aspects include the ability of the invention to treat patients presenting with a primary tumor who may have metastatic tumors, or tumor cells in the earlier stages of metastatic tumor seeding. As an anti-angiogenic strategy, the compositions and methods may also be used to prevent tumor development in subjects at moderate or high risk for developing a tumor, as based upon prognostic tests and/or close relatives suffering from a hereditary cancer.

Therapeutically effective doses of the anti-CEP antibody or antigen binding portion thereof can be readily determinable using data from an animal model. Experimental animals bearing solid tumors are frequently used to optimize appropriate therapeutic doses prior to translating to a clinical environment. Such models are known to be very reliable in predicting effective anti-cancer strategies. For example, mice bearing solid tumors are widely used in pre-clinical testing.

In using the anti-CEP antibody or antigen binding portion thereof in anti-angiogenic therapies, one can also draw on other published data in order to assist in the formulation of doses for clinical treatment. For instance, although the agents and methods described herein have distinct advantages over those in the art, the information in the literature concerning treatment with other polypeptides can still be used in combination with the data and teaching in the present application to design and/or optimize treatment protocols and doses.

Any dose, or combined medicament of the anti-CEP antibody or antigen binding portion thereof, that results in any consistently detectable anti-angiogenic effect, inhibition of metastasis, tumor vasculature destruction, tumor thrombosis, necrosis and/or general anti-tumor effect. The application may also be effective against vessels downstream of the tumor, i.e., target at least a sub-set of the draining vessels, particularly as cytokines released from the tumor will be acting on these vessels, changing their antigenic profile.

Combination Therapy

It will also be appreciated that the anti-CEP antibody or antigen binding portion thereof can be used in combination and adjunctive therapies for treating aberrant angiogenesis (e.g., neoplastic disorders). The phrase "combination therapy" can embrace the administration of the anti-CEP antibody or antigen binding portion thereof, and a therapeutic agent as part of a specific treatment regimen intended to provide a beneficial effect from the co-action of these therapeutic agents. Administration of these therapeutic agents in combination typically is carried out over a defined time period (usually minutes, hours, days or weeks depending upon the combination selected). "Combination therapy" can embrace administration of these therapeutic agents in a sequential manner; that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage having a fixed ratio of each therapeutic agent or in multiple, single dosages for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues.

The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" can also embrace the administration of the therapeutic agents as described above in further combination with other biologically active ingredients (such as, but not limited to, a second and different therapeutic agent) and non-drug therapies (such as, but not limited to, surgery or radiation treatment). Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

The phrase "adjunctive therapy" can encompass treatment of a subject with agents that reduce or avoid side effects associated with the combination therapy, including, but not limited to, those agents, for example, that reduce the toxic effect of anticancer drugs, e.g., bone resorption inhibitors, cardioprotective agents; prevent or reduce the incidence of nausea and vomiting associated with chemotherapy, radiotherapy or operation; or reduce the incidence of infection associated with the administration of myelosuppressive anticancer drugs.

In one example, the therapeutic agent administered in combination therapy with the antibodies described herein can comprise anti-proliferative agents. The phrase "anti-proliferative agent" can include agents that exert antineoplastic, chemotherapeutic, antiviral, antimitotic, antitumorgenic, and/or immunotherapeutic effects, e.g., prevent the development, maturation, or spread of neoplastic cells, directly on the tumor cell, e.g., by cytostatic or cytocidal effects, and not indirectly through mechanisms, such as biological response modification. There are large numbers of anti-proliferative agents available in commercial use, in clinical evaluation and in pre-clinical development, which could be used by combination drug chemotherapy. For convenience of discussion, anti-proliferative agents are classified into the following classes, subtypes and species: ACE inhibitors; alkylating agents; angiogenesis inhibitors; angiostatin; anthracyclines/DNA intercalators; anti-cancer antibiotics or antibiotic-type agents; antimetabolites; antimetastatic compounds; asparaginases; bisphosphonates; cGMP phosphodiesterase inhibitors; calcium carbonate; cyclooxygenase-2 inhibitors; DHA derivatives; DNA topoisomerase; endostatin; epipodophylotoxins; genistein; hormonal anticancer agents; hydrophilic bile acids (URSO); immunomodulators or immunological agents; integrin antagonists; interferon antagonists or agents; MMP inhibitors; miscellaneous antineoplastic agents; nitrosoureas; NSAIDs; ornithine decarboxylase inhibitors; pBATTs; radio/chemo sensitizers/protectors; retinoids; selective inhibitors of proliferation and migration of endothelial cells; selenium; stromelysin inhibitors; taxanes; vaccines; and vinca alkaloids.

The major categories that some anti-proliferative agents fall into include antimetabolite agents, alkylating agents, antibiotic-type agents, hormonal anticancer agents, immunological agents, interferon-type agents, and a category of miscellaneous antineoplastic agents. Some anti-proliferative agents operate through multiple or unknown mechanisms and can thus be classified into more than one category. For example, the anti-CEP antibody or antigen binding portion thereof can be administered in combination with a VEGF inhibitor, such as Avastin.

In some embodiments, the anti-CEP antibody is administered concurrently with a second therapeutic agent. As used herein, the term "concurrently" indicates that the subject antibody and the second therapeutic agent are administered separately and are administered within about 5 seconds to about 15 seconds, within about 15 seconds to about 30 seconds, within about 30 seconds to about 60 seconds, within about 1 minute to about 5 minutes, within about 5 minutes to about 15 minutes, within about 15 minutes to about 30 minutes, within about 30 minutes to about 60 minutes, within about 1 hour to about 2 hours, within about 2 hours to about 6 hours, within about 6 hours to about 12 hours, within about 12 hours to about 24 hours, or within about 24 hours to about 48 hours of one another.

In some embodiments, the anti-CEP antibody is administered during the entire course of treatment with the second therapeutic agent. In other embodiments, a subject antibody is administered for a period of time that is overlapping with that of the treatment with the second therapeutic agent, e.g., the antibody treatment can begin before the treatment with the second therapeutic agent begins and end before the treatment with the second therapeutic agent ends; the antibody treatment can begin after the treatment with the second therapeutic agent begins and end after the antibody treatment ends; the antibody treatment can begin after the treatment with the second therapeutic agent begins and end before the treatment with the second therapeutic agent ends; or antibody treatment can begin before the treatment with the second therapeutic agent begins and end after the treatment with the second therapeutic agent ends.

The following example is for the purpose of illustration only and is not intended to limit the scope of the claims, which are appended hereto.

Example 1

Humanization, also known as complementary determining region (CDR) grafting, has been well established for reducing the immunogenicity of xenogeneic monoclonal antibodies and improving their activation in the human immune system. The principles of constructing a humanized mAb by replacing human CDRs with murine CDRs are relatively straightforward. However, simply grafting murine CDRs into human frameworks does not always maintain the binding affinity and specificity of the original murine mAb (mumAb). Nevertheless, identification of murine CDRs and selection of human frameworks are the essential steps in reproducing the function of the original one.

Identification CDRs of a Mouse Monoclonal Antibody Against CEPs

An anti-CEP murine monoclonal antibody (anti-CEP mumAb) was developed. The isotype of anti-CEP mumAb was determined to be IgG2a. The light chain belongs to κ subgroup. The six CDRs for the mouse variable light (muVL) and variable heavy (muVH) chains were identified using the Kabat sequence definition based on the amino acid sequences deduced from cDNA sequences (FIG. 1).

Selection of Human Frameworks as Mouse CDR Acceptors

By searching human consensus sequences of variable regions from the Kabat Database, three heavy subgroups (huVHI, huVHII, and huVHIII) and four light κ subgroups (huVKI, huVKII, huVKIII, and huVKIV) were selected and aligned with sequences of muVL and muVH. The pairwise scores, the number of identities between the two sequences divided by the length of the alignment and represented as a percentage for comparison of mouse variable sequences with each human consensus sequences. The alignment results indicated that the human consensus sequences huVHI and huVKIV had highest similarity compared with the mouse variable regions. Although the identity between two sequences might not reflect the similarity of overall functional structures, huVHI and huVKIV were eventually chosen as pilot human frameworks for humanized constructs.

The amino acid sequences of the mouse and humanized variable regions were aligned, and the secondary structure of each variable fragment was subsequently predicted by computer modeling. The predicted structure in the "ribbon mode" of huVL and huVH were superimposed with muVL and muVH, respectively. It was found that the entire model of huVL perfectly overlapped that of muVL. The patterns of CDR loops of huVL and muVL were nearly the same. Unlike the perfect superimposition of huVL with muVL, the conformation of the CDR3 loop of huVH was found to be different from that of muVH. No superimposition was observed in that area. However, it has been reported that the third CDR of the heavy chain (CDRH3) which lies in the center of the antigen-binding site shows significant variability in its length, sequence, and structure, and is one of the most difficult structures to model. The results of computer modeling suggested that anti-CEP humanized antibody (anti-CEP huAb) might inherit the binding specificity of its mouse counterpart with only a slight change of binding affinity.

Construction of Humanized Variable cDNA Fragments

Unlike template-required gene conversion mutagenesis that was used for the construction of bevacizumab, the assembly polymerase chain reaction allows integration of any two or more desired oligonucleotides without using a DNA template. Therefore, two sets of oligonucleotides with a short overlapping segment (eight for huVL; nine for huVH) were designed for assembly of an intact humanized variable cDNA fragment according to the nucleotide sequences of huVL and huVH (FIG. 3). The product of assembly PCR was analyzed by electrophoresis on a 1% agarose gel.

Figure 5:
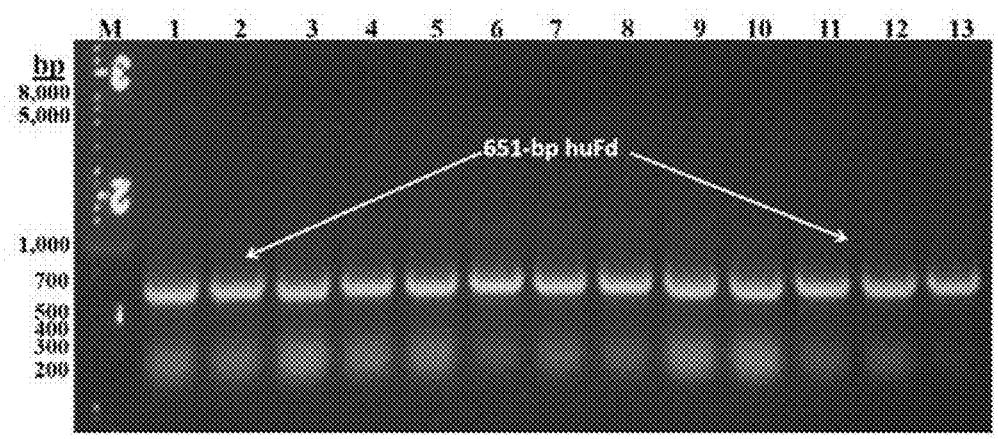
FIG. 5 illustrates the results of an assay showing PCR product analyzed in a 0.8% agarose gel for targeting positive clones with pFUSE-huH by PCR. Lane 1. DNA size marker; Lanes 2-14. Randomly selected clones.

Construction of pFUSE2-huL and pFUSE-huH for Expression of the Full Length Anti-CEP huAb In order to express the full length anti-CEP huAb in mammalian cells, the recombinant plasmids pFUSE2-huL and pFUSE-huH were prepared for expressing the light chain and the heavy chain, respectively. Because the DNA inserts, prepared as described above, and the plasmid vectors pFUSE2-CLIg-hk and pFUSE-CHIg-hG1 were co-digested to generate two different sticky ends at both the 5'- and 3'-ends, the cDNA fragment was expected to be inserted into the vector in one direction. Therefore, it was not necessary to recheck the orientation of the DNA inserts. To seek the positive clone with pFUSE2-huL, clones were randomly screened by PCR. Only the clones containing the recombinant plasmid delivered the product of the DNA insert upon PCR amplification. As seen in FIG. 4, the electrophoretic analysis indicated that clones 3 and 8 contained the requisite plasmid by amplifying humanized light chain (huL, 645 bp). DNA sequencing showed that clones 3 and 8 were identical. As done with pFUSE2-huL, 13 clones were randomly selected to target positive clones with pFUSE-huH. As seen in FIG. 5, all of these clones were shown to be positive by amplifying humanized Fd fragment (huFd, 651 bp). Clones 1, 5, 7, and 10 were selected for DNA sequencing which showed them to be identical. No reading frame shifts or mutations were found in the incorporated DNA fragments according to the sequencing results.

Construction of pFabCEP for Expression of Anti-CEP $F_{ab}$

Based on the original plasmid vector pFUSE-CHIg-hG1, the recombinant plasmid pFabCEP was reconstructed to express the anti-CEP Fab fragment in mammalian cells. The plasmid pFUSE-CHIg-hG1 and DNA insert huFd+SV40 pAn were digested with EcoRI and XmnI for generating the plasmid pFdCEP. Evidence for the incorporation of the insert was then sought by PCR testing of 9 clones. Only clones 5 and 7 did not produce the insert. The remaining clones were sequenced and determined to be identical.

The plasmid pFabCEP was subsequently created by integration of the XmnI-digested pFdCEP with the undigested DNA insert prom+huL+SV40 pAn. After bacterial transformation with the ligation product, 22 clones were randomly tested by PCR. Only clones 10 and 19 were determined to carry the plasmid pFabCEP by showing amplified cDNA of huL. The low efficiency of formation of pFabCEP reflected the difficulty of incorporation of a large DNA insert like prom+huL+SV40pAn (1562 bp).

As a result of the blunt-end DNA ligation, 50% of the DNA inserts theoretically might get connected in the wrong orientation, and more than one insert might be incorporated into one plasmid vector by chance. Therefore, the orientation and number of copies of the DNA insert were verified by PCR. In theory, only the recombinant plasmid with a correctly oriented DNA insert can be amplified by PCR using the forward external primer and reverse internal primer. The recombinant plasmid containing multiple inserts should generate fragments of different size.

Because pFabCEP included one restriction site for EcoRI and three for XmnI, these cutting sites were used to confirm the copy number of the insert (FIG. 6). The amplified DNA fragment with the correct size (~1600 bp) in the PCR products of clones 10 and 19 provided presumptive evidence for the correct orientation and the presence of a single copy of the insert. The one single band of single-digested products of clones 10 and 19 also supported the above conclusion. The results of XmnI digestion of clones 10 and 19 showed no reading frame shifts occurring during the DNA ligation reaction. The positive clones 10 and 19 were sequenced and determined to be identical. No mutations were observed.

Inhibition of CEP-induced angiogenesis by anti-CEP mumAb was demonstrated. Inspired by the strategy of preparing and using bevacizumab and ranibizumab for suppressing VEGF-induced angiogenesis, humanization of anti-CEP mumAb was postulated to generate anti-CEP huAb and its $F_{ab}$ fragment. In order to achieve this goal, recombinant plasmids pFUSE2-huL/pFUSE-huH and pFabCEP were successfully constructed using modern techniques of molecular cloning for expression of full length anti-CEP huAb and $F_{ab}$.

Experimental Procedures
Methods
Agarose Gel Electrophoresis

A 1% agarose gel was prepared by heating and dissolving 0.72 g of agarose in 60 mL of 1×TAE buffer in a microwave oven. The solution was then cooled to about 60° C. and 2 µL of ethidium bromide (10 mg/mL) was added, mixed and poured into a gel tray sealed with masking tape. A 10- or 14-well comb was inserted to form wells. The gel was ready for use when solidified. About 800 mL of 1×TAE was also used as a running buffer. The electrophoresis for DNA samples was carried out at 9V/cm for 45 min. PerfectSize DNA molecular weight ladder with a range of 100 to 10,000 bp was employed for comparisons of DNA samples.

DNA Gel Extraction

DNA fragments were extracted and purified using Agarose GelExtract Mini Kit. Briefly, the DNA-containing gel was excised and completely dissolved in 3 volumes of Buffer PS at 50° C. The solution was cooled and loaded onto the silica-membrane of the microcentrifuge column that was pre-equilibrated with Buffer BL in the presence of salt with high concentration. The solution was discarded while the DNA remained bound after centrifugation at 13,000 rpm for 1 min. Following washing the column with 700 µL of 80% ethanol-containing Buffer PW, the DNA was recovered by adding 50 µL of sterile double deionized water (ddH$_2$O).

Preparation of E. coli JM109 Competent Cells

E. coli JM109 competent cells were prepared using Transformation and Storage Solution (TSS). JM109 was inoculated aseptically in 10 mL of LB and incubated overnight on a shaker at 37° C. The next day 1 mL of the culture, after incubation overnight, was placed in 100 mL of fresh LB and incubated until OD600 reached between 0.3-0.4. The cells were then harvested by centrifuging at 6000×g for 10 min at 4° C. Then the cells were resuspended in 1 mL of TSS and, in 100-µL aliquots, immediately placed at −80° C.

Transformation of E. coli JM 109 with pFUSE2-CLIg-Hk and pFUSE-CHIghG1

Plasmids pFUSE2-CLIg-hk (20 µg; blasticidin-resistant) and pFUSE-CHIg-hG1 (20 µg; zeocin-resistant) delivered in TE buffer were purchased from InvivoGen. For lifetime conservation, transformation was carried out by adding 1 µg of each plasmid into a 1.5 mL tube containing 100 µL of E. coli JM109 competent cells. The tube was gently mixed and kept on ice for 30 min. Four hundred µL of TSS was then added to the tube, mixed by inverting the tube a few times, and incubated at 37° C. for 1 hour. The cell suspension was evenly spread onto a 100-mm LB-agar plate containing 100 µg/mL of blasticidin for pFUSE2-CLIg-hk or 20 µg/mL of zeocin for pFUSE-CHIg-hG1. The LB agar plates were incubated at 37° C. overnight. The next day, the transformant was selected by randomly picking one single colony that then was inoculated into 10 mL of LB for growth. When OD600 reached 0.5, the cells were spun down at 6000×g for 10 min at room temperature. The cell pellet was resuspended with 5 mL of 85% fresh LB and 15% glycerol. The cell suspension was stored in 1-mL aliquots at −80° C. until use.

Isolation of pFUSE2-CLIg-Hk and pFUSE-CHIg-hG1

Plasmids were isolated using a StrataPrep Plasmid Miniprep Kit. The plasmid-containing E. coli JM109 cells were incubated overnight at 37° C. with shaking at 200 rpm. The next day, 1.5 mL of the cell culture was spun down at 6000×g for 5 min and then resuspended in 100 µL of solution 1 (50 mM Tris, pH 7.5; 10 mM EDTA; 50 µg/mL RNase A) followed by addition of 100 µL of solution 2 (0.2 M NaOH; 1% SDS) and subsequently 125 µL of solution 3 (proprietary neutralizing contents). After gentle mixing, the contents were centrifuged at 13,000 rpm for 5 min., and then the plasmid-containing supernatant was loaded onto the fiber matrix of a microspin cup that was seated in a 2-mL receptacle tube. The plasmid remained in the fiber matrix after centrifugation. The plasmid-bound fiber matrix was washed twice with 750 µL of wash buffer (100 mM NaCl; 2.5 mM EDTA; 10 mM Tris, pH 7.5; 50% ethanol). The plasmid was extracted from the matrix by adding 50 µL of ddH$_2$O and stored at −20° C. until use.

Computer Modeling of Mouse and Humanized Variable Fragments

Sequences of the mouse and selected human variable fragments were used to construct computer graphics models using Automated Mode in SWISS-MODEL Workspace. All the models were inspected using DeepView. Superposition of the selected human variable region with its mouse counterpart was performed using the "Magic fit" option of DeepView to determine which framework residues should be incorporated into the humanized antibody.

Construction of cDNA of Humanized Variable Regions Using Assembly PCR

Based on the DNA sequences of humanized variable regions, eight oligonucleotides L2F1, L2R2, L2F3, L2R4, L2F5, L2R6, L2F7, and L2R8 were designed to build the humanized variable light fragment (huVL), while nine oligonucleotides H2F1, H2R2, H2F3, H2R4, H2F5, H2R6, H2F7, H2R8, and H2F9 were used to build the humanized variable heavy fragment (huVH). These oligonucleotides appeared to alternate between sense and antisense directions, and the short overlapping segments determined the order of the PCR fragments (FIG. 3). To construct each variable fragment, the corresponding oligonucleotides were joined together by assembly PCR using Verbatim High fidelity PCR Kit. Each reaction tube included 5 μL of 5× High Fidelity buffer, 1.5 μL of 20 mM dNTP Mix, 3 μL of 10 μM oligonucleotide 1, 3 μL of 10 μM oligonucleotide 2 with an overlapping segment, and 0.5 μL of Verbatim High Fidelity DNA polymerase (1 unit/μL). The final volume totaled 25 μL. In assembly PCR there was no DNA template added. For building huVL, four reaction tubes were set up and labeled continuously with number 1-4 in the first cycling process.

Two reaction tubes labeled A and B were set up in the second cycling process, e.g., 3 μL of the product from tube 1 and 3 μL of the product from tube 2 were added into tube A without changing other components. In the final cycling process, one reaction tube was set up by adding 3 μL of product from tube A and 3 μL of product from tube B.

The intact cDNAs of huVL and huVH were then amplified by basic PCR using PCR Master Mix. Each reaction tube included 1 μL of the final assembled product, 1 μL of 10 μM forward primer (VLfNcoI for huVL; VHfEcoRI for huVH), 1 μL of 10 μM reverse primer (VLrBsiWI for huVL; VHrNheI for huVH), 25 μL of 2×PCR Master Mix solution (50 units/mL Taq DNA polymerase; 400 μM dNTP; 3 mM MgCl2), and 22 μL of ddH$_2$O. Two unique restriction sites were integrated into each final PCR product for the subsequent cloning (NcoI and BsiWI for huVL; EcoRI and NheI for huVH). All of the cycling processes were accomplished using an Eppendorf Mastercycler.

The PCR products were analyzed by 1% agarose gel electrophoresis at 100V for 45 min (2 μL per well, ~100 ng), and subsequently gel-extracted. A total of about 10 μg DNA fragment of each variable region was dissolved in 50 μL of ddH$_2$O.

Construction of Recombinant Plasmids pFUSE2-huL and pFUSE-huH

The cDNA fragment for the humanized VL and pFUSE2-CLIg-hk were co-digested by restriction enzymes NcoI and BsiWI, while the humanized VH cDNA fragment and pFUSE-CHIg-hG1 were co-digested by EcoRI and NheI. For each reaction, the DNA insert (0.5 μg) or plasmid vector (1 μg) and 2 μL of two restriction enzyme (1 μL from each enzyme) were added into a fresh 1.5-mL tube followed by adding 2 μL of 10× FastDigest® buffer. The final volume of each reaction was adjusted to 20 μL by addition of ddH$_2$O. After mixing gently, each reaction tube was incubated at 37° C. for 10 min. The digested DNA insert and its corresponding plasmid were gel-extracted. The DNA insert was then ligated with the plasmid using DNA ligation kit Ver. 2.1. The total volume of the ligation reaction mixture was 10 μL containing 5 μL of Solution 1 and 5 μL of the DNA mixture of the insert and plasmid vector. The molar ratio of DNA insert (1.5 pmol) to plasmid vector (0.3 pmol) was set to five. The concentrations of the insert and plasmid vector were determined by the following equation:

$$\text{Concentration of } DNA \left(\frac{ng}{\mu L}\right) = (O.D. \text{ at } 260 \text{ nm}) \times (\text{dilution factor}) \times 50$$

The mixture was incubated at 16° C. for 2 hours. The ligation product was then introduced into *E. coli* HB 2151 by adding 5 μL of the ligation mixture directly into 100 μL of HB2151 competent cells and transformation was performed. The bacterial cells were spread on a LB agar plate containing an appropriate antibiotic and incubated overnight at 37° C.

Selection of Recombinant Plasmid-Containing *E. coli* HB2151 Clones

To quickly screen for the presence of clones with a recombinant plasmid, a 10-μL pipette tip was used to transfer a tiny portion of one single colony directly into a 0.5-mL PCR thin tube and suspended in PCR reaction mixture. The PCR product was analyzed in a 1% agarose gel. Only clones with a recombinant plasmid allowed success of PCR using certain primers.

The positive clones were harvested from the original plate and stored. The recombinant plasmids were isolated, and both strands were sequenced using primers VLfNcoI and CLrev for pFUSE2-huL; primers VHfEcoRI and CH1rev for pFUSE-huH. The original sequencing results generated from Biotic Solutions were verified using FinchTV 1.4 software and aligned with the desired sequences using an online sequence alignment tool, the ClustalW2 program. The DNA sequence was translated using the translate tool at the Expert Protein Analysis System (ExPASy) proteomics server. The identities of the clones with recombinant plasmid were verified by comparing the DNA sequence and the deduced amino acid sequence using AlignX alignment software. The clones containing the correct recombinant plasmid, i.e., pFUSE2-huL for humanized light chain expression and pFUSE-huH for humanized heavy chain expression, were finally harvested and frozen at −80° C. for archival storage.

Construction of the huFd+SV40 pAn DNA Insert

The cDNA fragment of human heavy Fd fragment (huFd) and a Simian Virus 40 late polyadenylation signal (SV40 pAn) were extracted from the original plasmid pFUSE-hH using PCR Master Mix. The huFd fragment was then integrated with the SV40 pAn by assembly PCR followed by basic PCR using the forward primer VHfEcoRI and reverse primer SV40R3. Two unique restriction sites (EcoRI and XmnI) involved in the primers VHfEcoRI and SV40R3 were added at 5'- and 3'-ends of the insert, respectively. The DNA insert was analyzed on 1% agarose gel and gelextracted. The insert (~5 μg) was stored in ddH2O at −20° C.

Construction of the pFdCEP Plasmid

The original plasmid pFUSE-CHIg-hG1 and the DNA insert huFd+SV40 pAn were codigested with restriction enzymes EcoI and XmnI. Recombination of digested pFUSE-CHIg-hG1 (0.5 pmol) with the digested insert (1.5 pmol) was performed using DNA ligation kit Ver. 2.1. The recombinant plasmid was subsequently introduced into *E. coli* HB2151. The positive clones were selected and verified. Using a StrataPrep Plasmid Miniprep Kit, 20 μg of pFdCEP was prepared.

Preparation of the DNA Insert Prom+hL+SV40 pAn

The DNA insert containing the hEF1-HTLV promoter, the cDNA of humanized light chain (huL), and SV40 pAn was extracted and amplified in one step by PCR using the recombinant plasmid pFUSE2-huL as a template. The amplified insert was analyzed on a 0.8% agarose gel and subsequently gel-extracted. About 3 μg of the DNA insert was obtained and stored at −20° C.

Example 2

A CHO suspension cell host system was chosen to express anti-CEP humanized mouse antibody (anti-CEP huAb) and its Fab fragment (huFab).

Affinity Measurement

The affinity constant is usually determined by titration experiments where the concentration of analytes at equilibrium is measured. With the application of surface plasmon resonance, biomolecule interaction analysis core (BIAcore) was developed to analyze interactions between analytes in solution and a ligand attached to a sensor chip surface, such as protein-protein, protein-peptide, protein-DNA, and protein-small molecule interactions. As shown in FIG. 7, both the association-rate (kon) and dissociation-rate (koff) constants can be determined by gathering a series of binding curves. The affinity (KD) can be calculated as follows.

$$\text{Affinity } (KD) = \frac{koff}{kon}$$

Expression of Anti-CEP mumAb

According to the yield of anti-CEP mumAb isolated using a protein A column, the hybridoma cells (clone 2D3.3G9-1) were able to produce approximately 3 mg per 100 mL during a 7-day expression at a seeding density of 106 cells/mL. Due to the strong binding specificity of protein A to mouse IgG2a, no non-specific binding was observed in the eluted fractions analyzed by sodium dodecyl sulfate polyacrylamide gel electrophoresis (SDS-PAGE).

Expression of Anti-CEP huAb and huFab

Chinese hamster ovary suspension (CHO-S) cells were transfected with pFUSE2-huL and pFUSE-huH for expression of full length anti-CEP huAb and with pFabCEP for expression of anti-CEP huFab. To detect the presence of anti-CEP huAb and huFab in the supernatant of CHO-S cell culture medium, indirect enzyme-linked immunosorbent assays (ELISAs) were carried out. The result indicated that the expression of anti-CEP huAb and huFab was accomplished by co-transfecting CHO-S cells with pFUSE2-huL and pFUSE-huH and single-transfecting with pFabCEP, respectively. To screen out a stable cell line for expression of anti-CEP huAb/huFab, 192 individual clones for each antibody were added to two 96-well plates and tested by ELISA (FIG. 8). The result indicated that clones A1 and K3 were able to generate the highest level of anti-CEP huAb and anti-CEP huFab, respectively.

The expression level of anti-CEP huAb in Clone A1 was monitored for 5 passages using ELISA. No significant decrease in protein expression level was observed among passages 1 to 5. The result suggested that the expression level of anti-CEP huAb was stabilized in Clone A1. In contrast, the expression level of anti-CEP huFab in Clone K3 was very unstable and decreased to zero by the third passage. Other candidates K2 and P1 also showed similar results in the expression level of anti-CEP huFab. It was speculated that it might be much more difficult to get the recombinant plasmid pFabCEP incorporated into the genome of CHO-S cells to stabilize the expression level because of its larger size (5643 bp) compared to pFUSE2-huL (4137 bp) and pFUSE-huH (4780 bp). However, the recombinant plasmid pFabCEP could be used for transient expression of anti-CEP huFab in mammalian cells.

The yield of 7-day expression of anti-CEP huAb in 100 mL of Clone A1 cell culture with a seeding density of 105 was approximately 200 μg based on the amount of the purified product. No non-specific binding was found during the protein A purification.

To increase the concentration of anti-CEP huAb in the supernatant, a CELLine CL 1000 bioreactor that allows cells to grow at an extremely high cell density (up to 108 cell/mL) was employed. Compared to the supernatant from the cell culture in a shaker flask, the concentration of anti-CEP huAb in the bioreactor appeared to be 50 times higher.

Affinity Measurement of Anti-CEP mumAb and huAB

The binding affinity of each antibody was measured using BIAcore technology. CEP-modified human serum albumin (CEP-HSA) immobilized on a CM5 sensor chip was used as a ligand. Based on results analyzed using curve fitting in the bivalent mode of BIAevaluation Software, the affinities of anti-CEP mumAb and huAb were determined to be 0.16 nM and 1.58 nM (KD), respectively (FIG. 9).

Cross-Reactivity of Anti-CEP mumAb and huAb

To investigate the binding specificity of anti-CEP mumAb and huAb, competitive inhibition of each antibody binding to CEP modified proteins by diverse epitopes was tested by competitive ELISA (FIG. 10). CEP-BSA and CEP-HSA were used as a coating material and standard, respectively.

The cross-reactivity of the antibody binding to each inhibitor was calculated by the following equation (Table 1).

$$\text{Cross-reactivity} = \frac{\text{Concentration at 50\% inhibition } (ic50) \text{ of standard}}{IC50 \text{ of cross-reactant}} \times 100\%$$

TABLE 1

Cross-reactivity of CPP-, CHP-, EP-, and OHdiA-modified proteins

| | Standard | Cross-reactant | | | |
|---|---|---|---|---|---|
| Anti-CEP antibody | CEP-HSA | CPP-HSA | CHP-BSA | EP-BSA | OHdiA-BSA |
| Murine   IC$_{50}$ (nM) | 1.98 | 6265 | 57990 | Not detected | Not detected |
| (0.1 μg/mL)   Cross-reactivity (%) | 100 | 0.03 | 0.003 | | |
| Humanized   IC$_{50}$ (nM) | 5.6 | 10530 | 4688490 | | |
| (0.1 μg/mL)   Cross-reactivity (%) | 100 | 0.05 | 0.0001 | | |

As shown above, the results indicate that the cross-reactivities of the murine and humanized antibodies with CPP-HSA are similar, and neither of the antibodies cross-reacts with EP-BSA and OHdiA-BSA. Surprisingly, the cross-reactivity of anti-CEP huAb with CHP-BSA is more than ten times lower than that of its mouse counterpart. Anti-CEP huAb has a higher selectivity than the mouse counterpart for CEP epitopes versus CHP epitopes.

To develop therapeutic agents for inhibiting CEP-induced angiogenesis, a Fab fragment and the corresponding full-length humanized mouse monoclonal antibody against CEPs were successfully expressed in CHO-S cells by transfecting with pFabCEP or pFUSE2-huL/pFUSE-huH, respectively. The expression level of anti-CEP huAb in a stable cell line, Clone A1, was increased by a factor of 50 by using a CELLine bioreactor. The purification of anti-CEP huAb was performed using a protein A column without interference by non-specific binding. Although our efforts to generate a stable cell line for Fab expression were not successful, the recombinant plasmid pFabCEP can be used for transient expression.

The recognition of the humanized antibody heavy chain by goat anti-human Fc antibody and of the humanized light chain by goat anti-human κ light chain antibody verified the success of humanization of anti-CEP mumAb. The affinity of anti-CEP huAb ($K_D$=1.58 nM) was determined to be about ten times weaker than its mouse counterpart ($K_D$=0.16 nM). According to the comparison of cross-reactivities among various haptens, anti-CEP huAb appeared to be more specific for binding CEPs versus CHPs than anti-CEP mumAb. However, the cross reactivity was vanishingly small in both cases.

Cultivation of CHO-S Cells

For expression of anti-CEP huAb and Fab fragment, the FreeStyle™ MAX CHO Expression System was purchased from Invitrogen. According to the user manual provided by Invitrogen, about 107 CHO-S cells were initially cultivated in a vented shaker flask containing 30 mL of pre-warmed FreeStyle™ CHO-S serum free medium supplemented with 8 mM L-glutamine. Cells were then incubated in 8% $CO_2$ at 37° C. with shaking at 100 rpm on a VWR orbital shaker, and subcultured at 105 viable cells/mL every 2-3 days under the same conditions. For long-term conservation, about 108 CHO-S (90% viable or higher) of each passage were harvested by centrifugation at 1000 rpm for 5 min and then resuspended in 10 mL of freezing medium containing fresh CHO-S serum free medium with 10% DMSO. The cell suspension was transferred in 1-mL aliquots to 1.7-mL cryogenic vials that were then placed into a foam box and frozen at −80° C. for the first 24-48 hours, then placed into liquid nitrogen in a cryogenic tank.

Transfection of CHO-S Cells with pFUSE2-huL and pFUSE-huH/pFabCEP

The recombinant plasmids pFUSE2-huL, pFUSE-huH, and pFabCEP were prepared. In order to optimize the result of transfection, CHO-S cells were freshly cultivated at $5 \times 10^5$ cells/mL with over 95% viable in 30 mL of CHO-S serum free medium one day before the operation. On the day of transfection, the cells were diluted to $1 \times 10^6$ cells/mL with fresh CHO-S serum free medium. The extra cells were frozen and stored. The recombinant plasmids were added into OptiPro™ serum free medium followed immediately by mixing with FreeStyle™ MAX Transfection Reagent.

Affinity Measurement of Anti-CEP mumAb/huAb Using BIAcore

The affinity of anti-CEP mumAb/huAb was determined using a BIAcore 3000 in the Molecular Biotechnology core at the Lerner Research Institute. The procedure for affinity measurement is also described in BIAcore 3000 Instrument Handbook. After docking a CM5 sensor chip and priming the flow system with HBS-EP buffer, CEP-HSA (337 mM in pyrrole) was immobilized on the chip (Table 13) with the Amine Coupling Kit.

Competitive ELISA for Evaluating Specificity of Anti-CEP mumAb/huAb

In order to test the binding specificity of anti-CEP mumAb and huAb, CEP-BSA was used as coating agent and CEP-HSA was used as a standard for purified anti-CEP mumAb/huAb immunoassays. CPP-HSA, CHP-BSA, EP-BSA, and OHdiA-BSA served as potential inhibitors for comparison. All the protein samples were prepared in 1×PBS. CEP-BSA, CEP-HSA, CPP-HSA, CHP-BSA, and OHdiA-BSA were synthesized by Li Hong. EP-BSA was synthesized by Liang Xin. For each inhibitor, ten serial dilutions of a standard, a blank, and a positive control, were run. Each well of a 96 well ELISA plate was coated with 100 μL of CEP-BSA solution (221 nM). The plate was incubated at 37° C. for 1 h, then washed with 300 μL of 1×PBS three times and then blocked by incubating 1 h at 37° C. with 200 μL of 5% BSA (in 1×PBS). Then the plate was rinsed three times with 300 μL of 0.1% BSA with 0.1% Tween 20 (in 1×PBS). Ten serial dilutions of inhibitor or standard (120 μL each with a dilution factor of 5) were preincubated at 37° C. for 1 h with 120 μL of anti-CEP mumAb (0.2 μg/mL)/huAb (2 μg/mL). The initial inhibitor and standard concentrations were CPP-HSA (44.3 μM), CHP-HSA (44.3 μM), EP-BSA (44.3 μM), OHdiA-HSA (44.3 μM), and CEP-HSA (44.3 μM), respectively. These samples were prepared by diluting stock solutions of CPP-HAS (203 mM), CHP-BSA (357 mM), EP-BSA (467 mM), OHdiA-HSA (720 mM), and CEPHSA (337 mM) with 1×PBS, respectively. Blank wells were filled with 0.1% BSA (100 μL). The wells for positive control were filled with the diluted antibody solution (50 μL) and PBS (50 μL). The antibody antigen complex solutions (100 μL per each well) were then added in duplicate to their respective halves of the plate, which was then incubated at room temperature with gentle agitation on a shaker for 1 h. After the supernatant was discarded, the wells were washed three times with 300 μL of 0.1% BSA with 0.1% Tween 20, and then 100 μL of 1:2000 diluted secondary antibody (goat anti-mouse IgG/HRP conjugate for anti-CEP mumAb; goat anti-human Fc gamma IgG/HRP conjugate for anti-CEP huAb) with 1×PBS/0.1% BSA was added. The plates were then incubated at room temperature with gentle agitation for 1 h and then washed three times with 300 μL of 0.1% BSA with 0.1% Tween 20 followed by adding 100 μL of ABTS Ready-to-Use substrate solution in each well. The absorbance in each well was measured with a Bio-Rad 450 microplate reader at 405 nm. Absorbance values for duplicate assays were averaged and scaled to make the maximum curve fit value close to 100 percent. The averaged and scaled percent absorbance values were plotted against the log of concentration. Theoretical curves for each plot were fit to the absorbance data with a four parameter logistic function, $$f(x) = (a - d)\left[1 + \left(\frac{x}{c}\right)^b\right]$$

using GraphPad Prism 6.0. Parameter a=the asymptotic maximum absorbance, b=slope at the inflection point, c=$IC_{50}$, and d=the asymptotic minimum absorbance.

Example 3

In this Example, we employed a modified phagemid vector pCGMT9 that was derived from pComb3 to construct a library of phage-displayed anti-CEP huFab mutants (Scheme 4.1, next page). 21 Briefly, cDNA fragments encoding the light chain and Fd fragment were introduced into pCGMT9 in which the Fd fragment was designed to fuse to a coat protein pIX on the phage. After transformation of *E. coli* XL1-Blue with the recombinant phagemid, anti-CEP huFab-fused phage was formed by helper phage VCSM13 that assembled the mature phage with relevant protein fragments including anti-CEP huFabfused pIX coat protein.

Generation of Variants of huVL and VH by Random Mutagenesis

Error-prone PCR was performed using a GeneMorph® II Random Mutagenesis Kit. In order to maximize the diversity of the mutants, the mutation rate was controlled to be 9-16 per kbp (the highest range of mutation rate) using a tiny amount of DNA template (20 ng) according to the official procedure. The PCR products were analyzed on a 1% agarose gel.

Construction of a Recombinant Phagemid pCGMT9-Anti-CEP huFab cDNA fragments of human constant light (huCL), the first segment of constant heavy (huCH1), and a linker containing a lac promoter, a ribosome binding site and a pelB leader were amplified by PCR and then analyzed on a 1% agarose gel.

The DNA inserts (1472 bp) were then prepared by assembly PCR and ligated with the digested plasmid vector pCGMT9. The ligation product was directly introduced into $E.\ coli$ XL1-Blue. Over $5\times10^5$ transformants were gathered to establish a phage display library. The diversity of the library was up to 5×105 if each transformant contained a different phagemid.

Enrichment of Anti-CEP huFab Mutants with Higher Affinity

Three rounds of screening were carried out using a panning assay. Compared to the output phage numbers from the first two rounds, the final round gave rise to a 100-fold enrichment of phages specific to CEP-BSA. Through this process, the probability for seeking clones with significantly improved affinity is greatly increased.

Phase ELISA of Randomly Selected Individual Clones

Figure 11A:
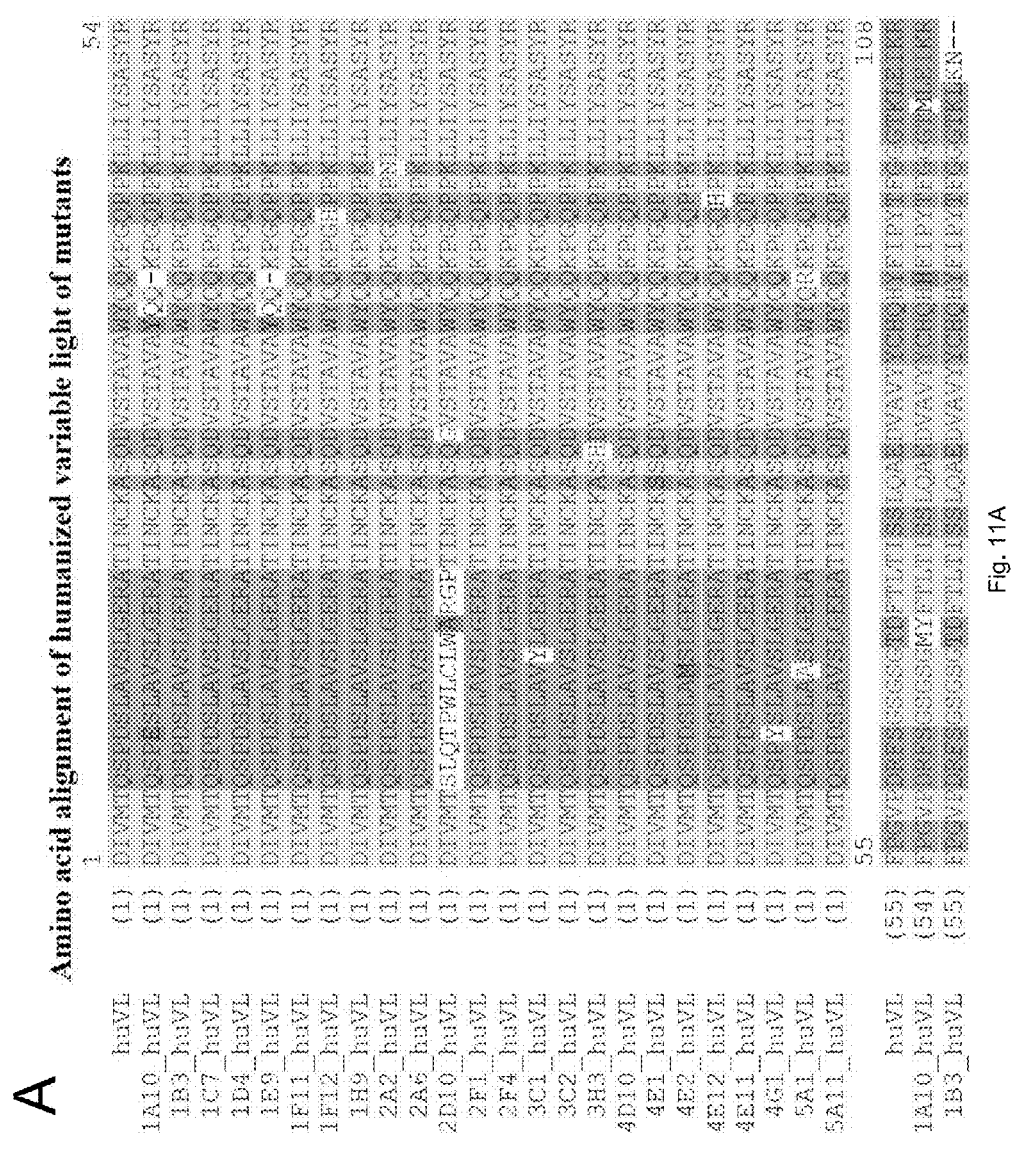
Figure 11A:
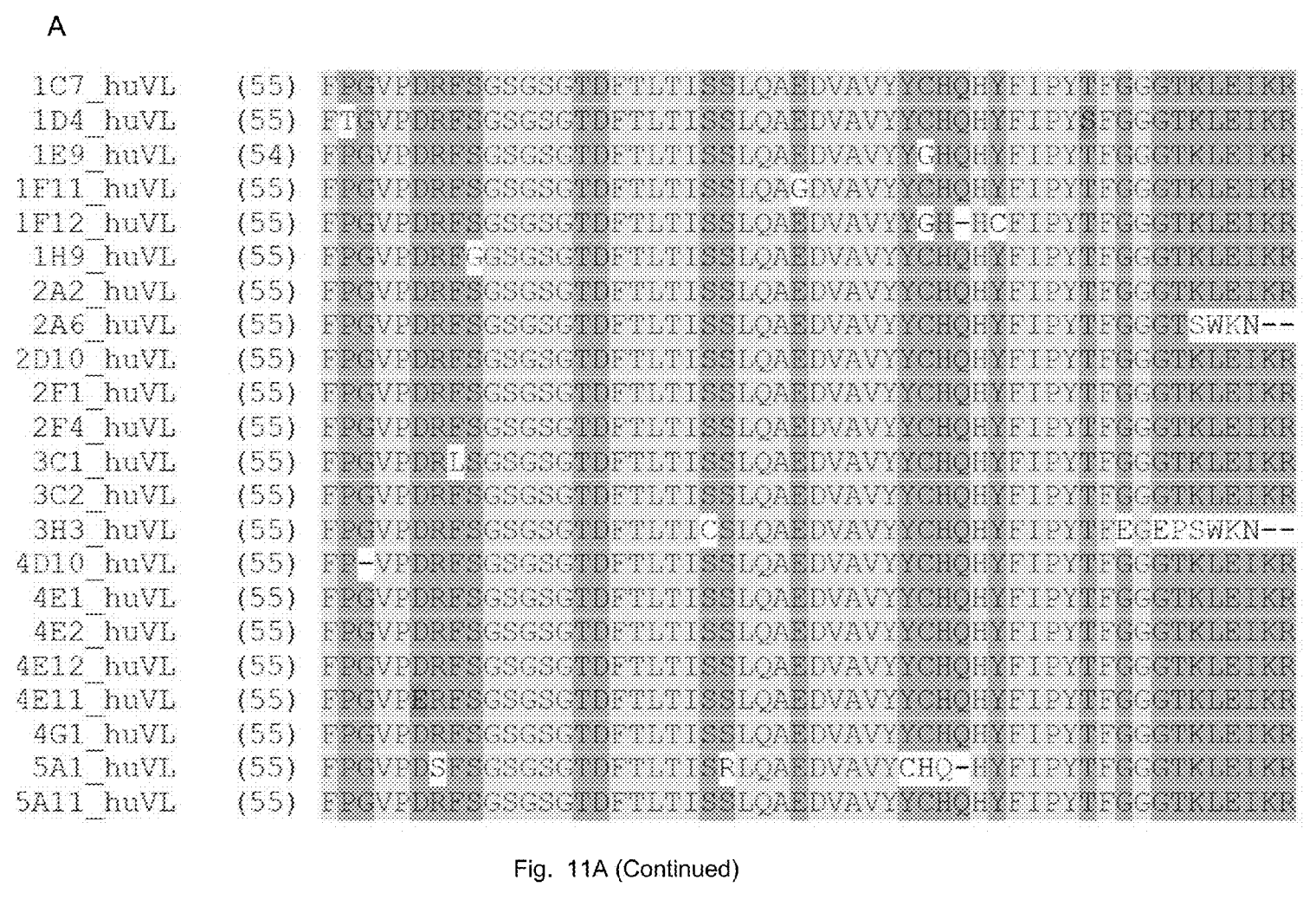
Figure 11B:
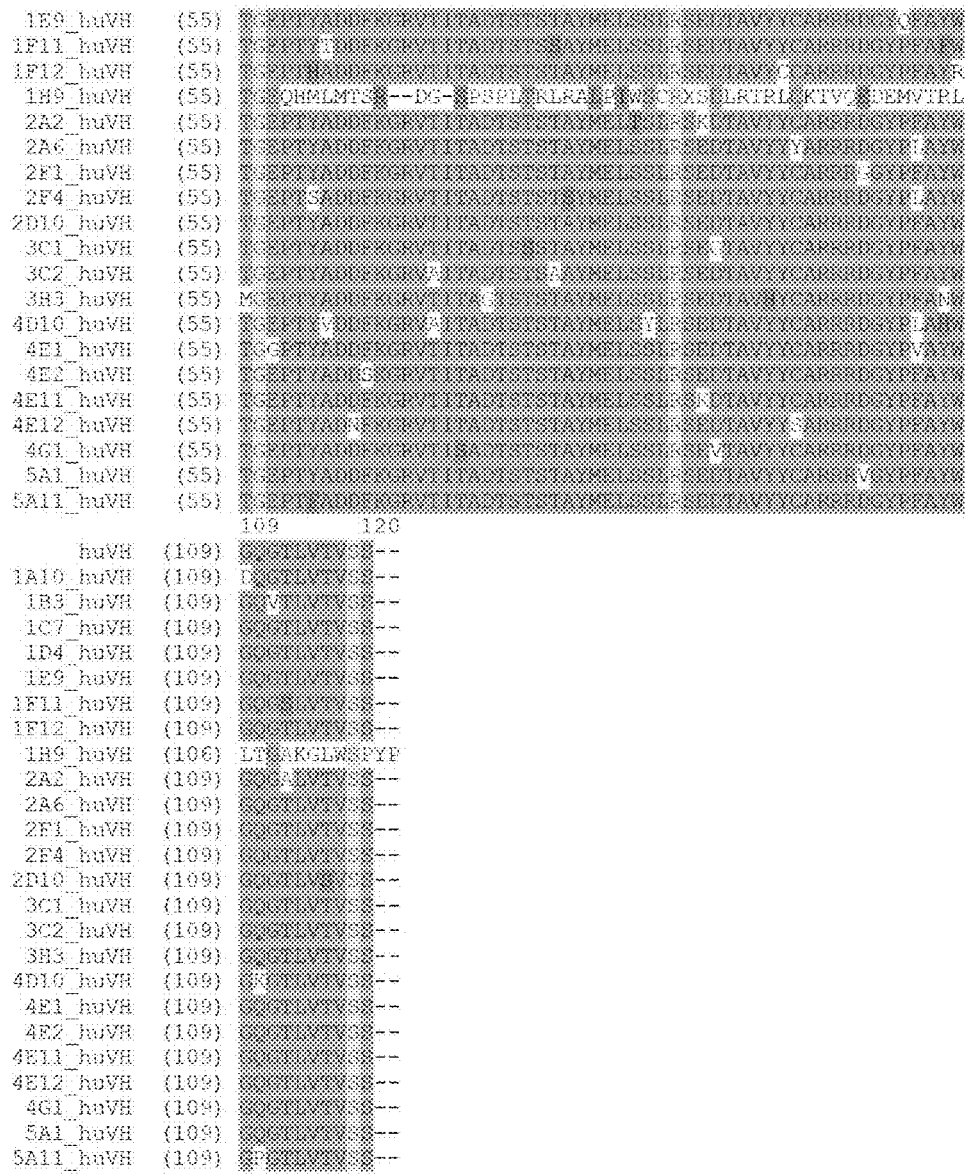
FIGS. 11 (A-B) illustrate the amino acid sequence alignment of humanized variable regions of mutants SEQ ID NOS: 9, 10, and 13-60.

After three rounds of screening, a total of 480 individual clones were randomly selected. The binding activity of anti-CEP huFab-fused phage from each variant was tested by phage ELISA. The clones with significant binding activity were chosen for DNA sequencing. The deduced amino acid sequence alignment of humanized variable mutants among the selected clones (FIG. 11(A-B).

Based on the absorbance values in five sets of phage ELISAs, a total of six clones showing relatively higher binding affinities were selected for expression of full length anti-CEP huAb mutants (Table 2).

TABLE 2

| Mutant | Amino acid mutations | |
|---|---|---|
| | huV$_L$ | huV$_H$ |
| 1B3 | Stop codon at 107 | T59A, E89V, G111V |
| 1D4 | P56T, T97S | S25F, E43Q, F64Y, Y80C |
| 1F12 | Q42H, C88G, Deletion at 90 Y91C | V2E, Y60H, Y95C, W108R |
| 2F1 | Not detected | F29L, D101G |
| 2F4 | Not detected | S25P, Y60S, A79S, F105L |
| 3C2 | Not detected | T69A, T78A |

Affinity Measurement of Anti-CEP huAb Mutants

Figure 12:
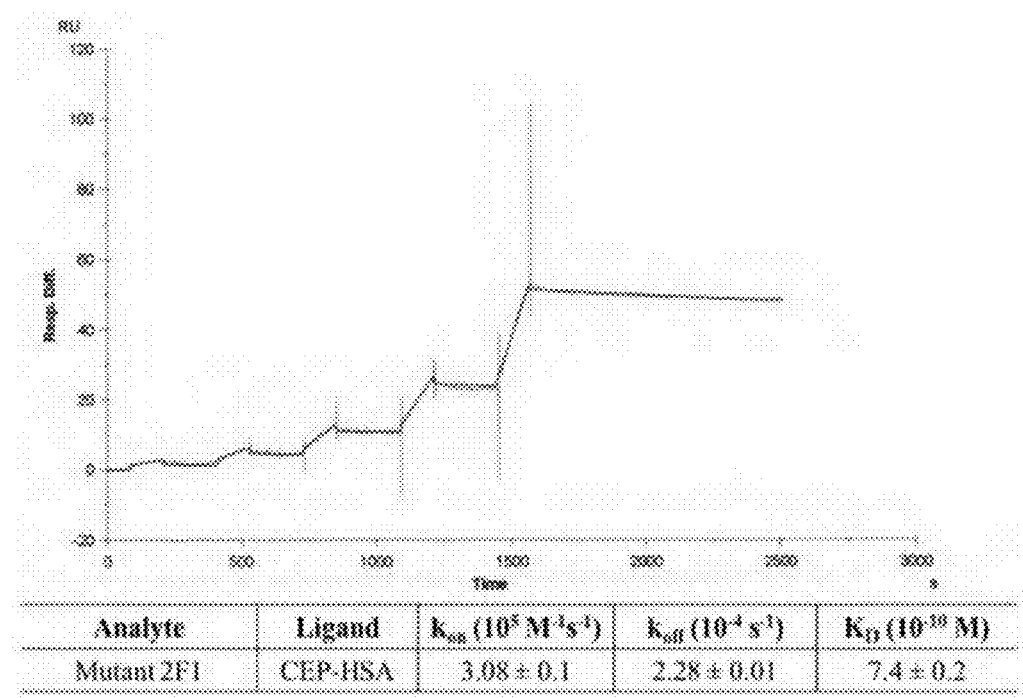
FIG. 12 illustrates a plot showing affinity measurement of Mutant 2F1 by BIAcore using a single-cycle kinetic approach.

Since the binding affinities determined by phage ELISA may not completely reflect the actual affinity of the mutants, the affinities of selected six variants were measured using BIAcore technology. An affinity quick comparison among the mutants was made by generating the sensorgram of each mutant with the same concentration of 10 nM in a single injection. Mutant 2F1 showed the highest binding affinity compared to the other candidates. The affinity (KD) was subsequently measured using single-cycle kinetic analysis (FIG. 12) and determined to be 0.74 nM, which is about two-fold stronger than the original anti-CEP huAb (KD=1.58 nM). Because the original anti-CEP huAb already possessed a significantly high binding affinity compared with bevacizumab (KD=1.1 nM), the affinity improvement of Mutant 2F1 by random mutagenesis is not expected to have practical significance.

A phage display library of anti-CEP huFab mutants was constructed successfully with a diversity of up to $5\times10^5$. The results of monoclonal phage ELISA suggested that the anti-CEP huFab variants were successfully expressed in $E.\ coli$ XL1-Blue and fused with the phage. By screening the anti-CEP huFab-fused phage variants, a clone, Mutant 2F1 with 2-fold higher binding affinity (KD=0.74 nM) compared to the original anti-CEP huAb (KD=1.58 nM) was obtained. Two mutated sites F29L and D101G were observed in the variable heavy region of Mutant 2F1 and located in CDRH1 and CDRH3, respectively. No mutations were observed in the variable light chain. Therefore, these mutations resulting in enhanced affinity indicated that the residues 29 in CDRH1 and 101 in CDRH3 are important for CEP binding. These mutations could be conserved for further affinity maturation using site-directed mutagenesis.

Example 4

Preparation of the Anti-CEP humAb

We prepared genes encoding $V_L$ and $V_H$ of our anti-CEP mouse mAb as described in Examples 1, 2, and 3. According to the deduced amino acid sequences of $V_L$ and $V_H$, we identified six CDRs from $V_L$ and $V_H$ by sequence-based CDR definitions and inserted them into human framework regions for construction of a humanized anti-CEP humAb. We built the DNA fragments encoding humanized variable regions using assembly PCR. The assembled DNA fragments were amplified and cloned into the pCGMT9 phagemid. After transformation of $E.\ coli$ HB2151 cells with the recombinant phagemid, the humanized anti-CEP mouse humAb was expressed and purified by protein G affinity chromatography as well as detected with goat anti-human IgG-horseradish peroxidase. The CEP binding affinity of our anti-CEP humAb was shown to be $K_d$=1.58 nM using BIAcore technology. This affinity is similar to the value ($K_d$=1.8 nM) reported for that of Avastin for VEGF. We established a stable cell line for expression of our humAb in suspension culture, and have accumulated more than 50 mg, a sufficient quantity for the proposed studies.

Anti-VEGF/Anti-CEP Combination Therapy can Dramatically Reduce Tumor Growth

We discovered that CEP is endogenously expressed in human melanoma, which also shows excessive vascularization and inflammation (assessed by CD31 and CD68 staining, respectively), at levels elevated six-fold over normal human skin (FIG. 13A left) as quantified normalized to normal skin (n=8) (FIG. 13A right). Administration of murine anti-CEP mAb, but not control IGg2a antibodies, to a murine melanoma allograft diminished progression and vascularization, and this effect was additive to that of the VEGF receptor (VEGFR) inhibitor AAL-993 (FIG. 13B left; tumour size on day 10 and right: quantification of vascular area n=4). The proangiogenic effect of CEP on human umbilical vein endothelial cells (HUVEC) is comparable to that of VEGF. However, CEP does not act through the VEGFR, but rather acts as a ligand for TLR2, apparently as a hetero-dimer with TLR1. CEP triggers MyD88-dependent GTP loading of Rac1 leading to stimulation of NFkB, but does not result in phosphorylation (activation) of VEGFR2 (FIG. 13C). Inhibition of HUVEC migration by the RGD peptide, an integrin receptor binding ligand, demonstrated that both the VEGF/VEGFR- and CEP/TLR2-induced angiogenic activities are mediated by integrins. On the other hand, aortic rings from TLR2 knockout mice exhibit angiogenesis in response to VEGF but not CEP. These discoveries led us to postulate that (1) CEP-induced angiogenesis can compromise anti-VEGF therapeutic measures by compensating for inhibition of the VEGF pathway, and that (2) tumor progression that occurs in patients after initial growth inhibition by Avastin can be reduced by concomitant blockade of CEP-induced angiogenesis with our anti-CEP humAb.

Example 5

This Example shows the application of PET imaging to determine tumor response to anti-CEP antibody therapy alone and to the combination therapy in xenograft models derived from glioblastoma and colorectal cancer cell lines.

We conducted longitudinal studies in two human tumor xenograft models of colorectal cancer and glioblastoma comparing the efficacy of Avastin and CEP antibody in terms of tumor growth. Each tumor xenograft model was treated either with Avastin or CEP antibody and the tumor size was monitored over 24 days. We then examined the synergistic effects of Avastin and CEP antibody in tumor xenograft model of glioblastoma through sequential treatment of Avastin followed by CEP antibody. In this longitudinal study, we first treated the xenografts with Avastin for 4 weeks followed by subsequent anti-CEP treatment for another 3 weeks. In addition, we also conducted [$^{18}$F]FDG- and [$^{18}$F]FMISO-PET imaging to determine which would be more responsive to CEP antibody therapy. Information of these studies would be needed for future translational studies.

Materials and Methods

Solvents and chemicals were purchased from Sigma-Aldrich unless stated otherwise. All chemicals obtained commercially were of analytic grade and used without further purification. Reference compound of [$^{18}$F]FMISO was purchased from ABX (Radeberg, Germany), [$^{18}$F]FDG was purchased from PETNET solution.

Radiosynthesis of [$^{18}$F]FMISO

The radiosynthesis of [$^{18}$F]FMISO was achieved in two steps in a TracerLab FXN automated synthesis module (GE Healthcare). Briefly, no-carrier-added $^{18}$F-fluoride was produced by the $^{18}$O (p,n)$^{18}$F nuclear reaction. Following nucleophilic fluorination with the tosylated precursor in the presence of $K_{222}$ and $K_2CO_3$, the unreacted tosylate was removed by hydrolysis with hydrochloric acid. The reaction mixture was then neutralized with sodium hydroxide and sodium bicarbonate. The final product was purified by C-18 semi-preparative high performance liquid chromatography (HPLC, Phenomenex C-18 column, 10μ, 250 mm×10 mm). Analytic HPLC was performed with a Raytest/Angilent series 1100 HPLC (Phenomenex C-18 column, 5μ, 250 mm×4.6 mm) system equipped with a UV detector and a Gabi radiodetector. [$^{18}$F] FMISO was produced with a high radiochemical purity (99%) and a specific activity of 1~2 Ci/mmol and was formulated in isotonic saline solution (pH 6.5-7.5), with a radioactivity concentration of 1.0~2.0 GBq/mL at the end of synthesis. The retention time of the radiolabeled [$^{18}$F]FMISO was identical to the retention time of the non-labeled FMISO as determined by ultraviolet detector under the same condition.

Preparation of Colorectal and Glioblastoma Xenografts

All animal experiments were performed in accordance with a protocol conforming to Case Western Reserve University Institutional Animal Care and Use Committee (IACUC) guidelines. U87-MG (glioblastoma) and CRC 174 (LS174T, colorectal cancer) cell lines were purchased from American Type Culture Collection (ATCC). Briefly, a cell suspension was mixed with an equal volume of matrigel (BD Biosciences) to provide a cell concentration of 6 million cells/200 uL, which was implanted subcutaneously into a 6-8 week-old female athymic nude mouse. Tumors were measured with a caliper or by CT imaging when the tumor volume reached approximately 200 mm$^3$. Mice were randomized into different groups for evaluation of therapeutic efficacy.

Dosing Regimen

For tumor size measurement, Avastin (2.5 mg/kg in 350 uL sterile phosphate buffer solution, PBS) and murine monoclonal anti-CEP IgG$^{32}$ (100 μg in 350 μL sterile PBS) were administered twice a week by intraperitoneal (i.p.) injection. Vehicle control was sterile PBS (350 μl). For monotherapy treatment, mice were divided into three groups (5 per group): control PBS group (350 μL), Avastin group and anti-CEP antibody group. For combination therapy treatment, mice were divided into two groups. Both groups of mice were treated with Avastin until eventual therapeutic failure (the inception of exponential growth) at which point one group of mice was switched to anti-CEP therapy and for the other group of the mice Avastin was continued.

To monitor changes in the tumor environment during monotherapy in xenograft models, longitudinal [$^{18}$F]FMISO and [$^{18}$F] FDG microPET/CT imaging were performed before and after treatments. These mice were treated with Avastin and CEP antibody daily after the tumor size reached approximately 200 mm$^3$ (12 days after the xenografts were prepared) and imaged with [$^{18}$F]FMISO at day 0, 2, 4, 8, 10 and [$^{18}$F]FDG at day 0, 7 and 14, respectively.

Tumor Volume Measurement

Throughout the study, the sizes of the tumors were either measured twice a week with a caliper or every other day with CT. When measured with calipers, the volume of a tumor was calculated with the equation [(A×B×C)]×0.523$^{33}$, where A is the longest measurement, B is the shortest measurement, and C is the highest measurement. Once the tumor volume reached approximately 200 mm$^3$, mice were randomized into different groups for evaluation of therapeutic efficacy.

In Vivo microPET/CT Imaging

PET imaging of [$^{18}$F]FMISO and [$^{18}$F]FDG were performed using a Siemens (Erlangen, Germany) Inveon microPET/CT scanner. For anatomic localization, both a PET image and a CT image were subsequently acquired for co-registration. Prior to PET imaging, CT scout views were taken to ensure that tumors were placed in the co-scan field of view (FOV) where the highest image resolution and sensitivity were achieved. Each group of mice was administered through lateral tail vein injection with a solution of [$^{18}$F]FDG or [$^{18}$F]FMISO (150~200 μCi in 0.2 ml saline). The animals were imaged under isoflurane anesthesia (2% in oxygen), and biologic monitoring for respiration and temperature was performed with a BioVet system (m2m imaging). For [$^{18}$F]FDG PET imaging, animals were fasted overnight prior to imaging with access only to water. Their diet was then replenished after imaging. The mice were statically imaged with either [$^{18}$F]FMISO at 90~110 min after injection or with [$^{18}$F]FDG at 40~60 min after injection. After PET data acquisition, a low-dose CT scan was performed for anatomic registration and attenuation correction. The microPET images obtained were reconstructed using a two-dimensional ordered-subset expectation maximum (OSEM) algorithm. PET and CT data were analyzed with Carimas software provided by the Turku PET Centre. For quantitative analysis, the co-registered microPET/CT images were used to accurately define the region of interest (ROI) and quantify the radioactivity concentrations in the tumor region in terms of standardized uptake values (SUV). For comparison, SUV of each mouse was normalized to its baseline scan. Tumor volumes were calculated in terms of mm$^3$ using the Carimas software.

In Vitro Immunohistochemistry Staining

At the end of the experiments, tumors were removed and postfixed by immersion in 4% paraformaldehyde (PFA) overnight, dehydrated in 30% sucrose solution, embedded in freezing optimal cutting temperature (OCT) compound, Fisher Scientific, Suwanee, Ga.), cryostat sectioned at 10 µm on a microtome and mounted on superfrost slides (Fisher Scientific). These tumor slices were subjected to CD31 immunohistochemistry staining. Generally, after being blocked with blocking buffer for 30 min, the frozen sections were incubated with primary antibody (rat anti-mouse CD31, 1:100, BD bioscience) for 2 hours at room temperature followed by storing at 4° C. overnight. The secondary antibody (anti-mouse Alexa Fluro 568, 1:800, Invitrogen) was then added and incubated for another 1 hour at 37° C. After washing with PBST (3×5 min), the slides were covered with VECTASHIEID mount media with 4',6-diamidino-2-phenylindole (DAPI). Images were collected using a Nikon fluorescence microscope.

Statistical Analysis

Quantitative data were expressed as mean±SEM, and statistical significance of observed differences among different experimental groups was calculated using a two-tailed student t test. p values<0.05 were considered to be statistically significant.

CEP Antibody Treatment Inhibited Tumor Growth in Colorectal and Glioblastoma Tumor Xenograft Models We evaluated the antitumor activity of CEP antibody in comparison with Avastin in both human colorectal and human glioblastoma tumor xenografts that were prepared by subcutaneous injection of LS174T and U87-MG tumor cell lines, respectively, into the flanks of athymic nude mice. For each tumor xenograft model, the animals were randomly assigned to 3 groups for anti-CEP, Avastin and PBS treatment. After the tumor size reached 200 mm$^3$ (day 12 after xenografts), each group was treated with CEP antibody, Avastin, and PBS twice a week.

As shown in FIG. 14, both CEP antibody and Avastin showed similar antitumor effects in both xenograft models. The tumor sizes were monitored over 25 days and compared with vehicle treated controls. For the LS174T human colorectal tumor-bearing xenografts, CEP antibody treatment showed an average tumor growth rate of 18% while Avastin treatment showed 15% (FIG. 14A). This was a significant reduction of 16.3% when compared with the vehicle-treated control littermates, which showed 31.2%. For U87-MG glioblastoma tumor-bearing mice, anti-CEP antibody and Avastin were administered intraperitoneally every other day. As shown in FIG. 14B, an even more profound inhibition of tumor growth was found in the glioblastoma tumor-bearing xenografts. The tumor size did not increase and remained practically the same over the 25 days when treated with either CEP antibody or Avastin. Compared to the PBS treated control littermates, the average tumor growth rate was reduced by 33.2%.

Following the imaging studies, we then examined the extent of angiogenesis in the tumor tissues through histochemistry using anti-CD31, which is a specific marker of newly formed blood vessels. At the end of the experiments, mice bearing LS174T tumor were euthanized and the tumor tissues were dissected and sectioned for CD31 staining. The extent of newly formed vasculature was then compared among the three treatment groups. As shown in FIG. 15A-C, the LS174T tumors treated only with PBS showed abundant vasculature, as indicated by strong CD31 staining. In comparison, the LS174T tumors treated with Avastin showed much less CD31 staining, suggesting angiogenesis was significantly reduced (FIG. 15D-F). More importantly, CEP antibody could even further reduce the extent angiogenesis as CEP-antibody-treated tumor tissue sections showed the least CD31 staining among the three treatment groups (FIG. 15G-I). Significant reduction of CD31 staining suggests that CEP antibody effectively inhibit formation of new blood vessels and halt or delay the tumor growth as previously monitored (FIG. 14).

Sequential Treatment with Avastin and then CEP Antibody Further Inhibited Glioblastoma Tumor Growth Because Avastin and anti-CEP inhibit tumor growth through two independent pathways with different mechanisms, we hypothesized that growth of a tumor resistant to Avastin could still be by anti-CEP, which inhibits tumor growth in a TLR-2-dependent manner without activation of VEGFR-1 and VEGFR-2. To test this hypothesis, we evaluated the synergistic effect of Avastin and CEP antibody. Thus mice bearing U87-MG glioblastoma cells were first prepared. At day 9 when solid tumor tissues are palpable, the xenografts were treated with Avastin (2.5 mg/kg) alone twice a week for 18 days until drug resistance was developed and the tumors resumed growing. At this point, the xenografts were divided into two groups, one group was subjected to continued treatment with Avastin (2.5 mg/kg) alone and the other group was subjected to treatment with Avastin combined with anti-CEP (5 mg/kg) twice a week. During the first phase of treatment, the tumors in all the xenografts grew very slowly until day 27, when drug resistance to Avastin treatment was developed. During the second phase of treatment after Avastin started failing, we observed significantly enhanced growth inhibition by CEP antibody when administered in combination with Avastin. Compared to Avastin therapy alone, the average tumor size was reduced by 28.9% by the end of the experiment. These studies suggested that CEP antibody did independently block the tumor growth promoted through a pathway that compensates for inhibition of the VEGF-mediated pathway by Avastin.

Non-Invasive Imaging for Efficacy Evaluation of Anti-CEP Treatment

The above studies demonstrated the potential of CEP-antibody as a therapeutic drug that can be used either by itself or in combination with Avastin to inhibit tumor growth. For future translational studies, an imaging marker must be identified that allows for quantitative assessment of anti-CEP treatment with high sensitivity and specificity. Thus, we evaluated [$^{18}$F]FDG- and [$^{18}$F]FMISO-PET to determine which technique would be more responsive to anti-CEP treatment.

[$^{18}$F]FDG PET imaging is commonly used for assessing the effects of chemotherapy on glucose metabolism in the tumor. To determine if [$^{18}$F]FDG-PET correlates with tumor growth, we conducted longitudinal imaging in LS174T tumor xenografts that were treated with CEP antibody twice a week starting from day 12 after xenografts. [$^{18}$F] FDG PET scans were acquired at day 0, 7 and 14 following anti-CEP treatment. As shown in FIG. 17, [$^{18}$F]FDG uptake in the tumor tissues showed a weak correlation (PBS: $r^2$=0.001941, anti-CEP: $r^2$=0.2767) with the tumor growth rate observed previously. After normalizing to day 0 and comparing with the control PBS group, we only observed reduction of [$^{18}$F]FDG uptake at day 7 after treatments. However, [$^{18}$F]FDG uptake was increased at later time points (i.e., at day 14). Overall, no significant differences were observed between the treated and control groups. Interestingly, PET images of the control tumors showed reduced [$^{18}$F]FDG uptake in the center of the tumor tissue due to the exponential tumor growth and subsequent necrosis.

On the other hand, solid tumors often develop hypoxia during their evolution. This is primarily caused by unregulated cellular growth, resulting in a greater demand on oxygen for energy metabolism. As a consequence, most solid tumors evolve their own tissue physiological microenvironment, which is largely dictated by abnormal vasculature and metabolism. Recently [$^{18}$F]FMISO was developed for PET imaging of hypoxia, which was designed to detect the changes in the tumor microenvironment after angiogenic therapy. We thus conducted [$^{18}$F]FMISO PET imaging of the LS174T human colorectal tumor xenografts to determine if [$^{18}$F]FMISO PET correlated with the efficacy of anti-CEP treatment. After the xenografts were treated with CEP antibody, [$^{18}$F]FMISO PET scans were acquired every other day. As shown in FIG. 18, uptake of [$^{18}$F]FMISO in tumor tissue increased over time and correlated well with tumor growth ($r^2$=0.9016). When normalized to day 0 and compared with the control PBS group (poor correlation, $r^2$=0.109), we observed significant differences over a period of 10 days after anti-CEP treatment. [$^{18}$F]FMISO uptake in CEP-antibody treated tumor xenografts was 42.8% higher than that in the control littermates, suggesting that CEP antibody induced hypoxia in the tumor tissue.

Figure 19:
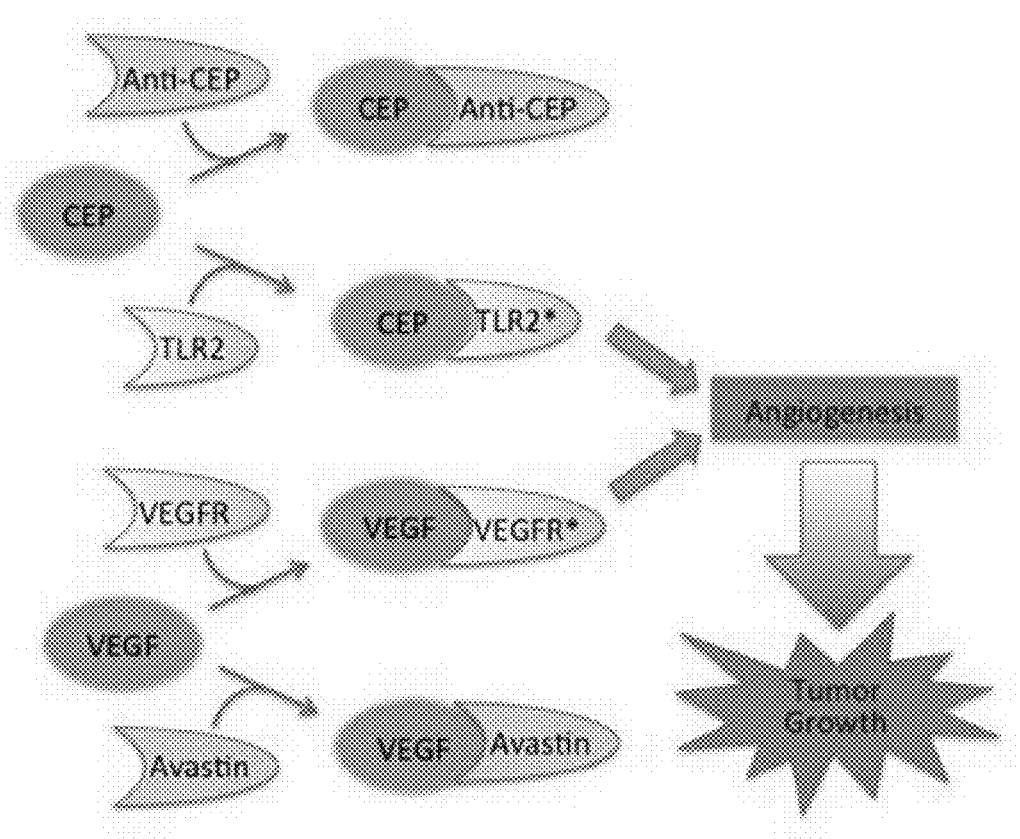
FIG. 19 illustrates a schematic showing TLR2 and VEGFR dependent pathways independently promote angiogenesis and tumor growth that can be inhibited by a monoclonal anti-CEP antibody and the anti-VEGF monoclonal antibody Avastin respectively.

Inhibition of angiogenesis is a major therapeutic strategy for halting tumor growth in cancer. FDA-approved drugs that inhibit VEGF-promoted angiogenesis such as Avastin and Lucentis have been thoroughly investigated and widely used in the clinic with moderate success. Most anti-VEGF therapies exhibit limited efficacy just for a few months before drug resistance is developed. This led us to hypothesize that multiple pathways exist that compensate each other in promoting vascularization during tumor growth. Our basic research on lipid oxidation led to discovery that some types of oxidatively truncated phospholipids convert primary amino groups of biomolecules into 2-(ω-carboxyethyl)pyrrole (CEP) derivatives, which are accumulated under inflammatory conditions inherent in cancer as well as age-related macular degeneration (AMD). Further studies showed that CEPs promote angiogenesis through a novel VEGF-independent TLR2-dependent pathway. As shown in FIG. 19, activation of TLR2 and VEGF apparently mediate two independent pathways that promote angiogenesis leading to tumor growth, which may compensate for each other and contribute to the development of drug resistance to single therapy alone. Synergistic inhibition of both angiogenesis pathways thus has the potential to improve patient response and clinical outcomes.

For this reason, we evaluated an anti-CEP antibody as a potential monoclonal antibody therapy. We first evaluated the efficacy of the anti-CEP antibody for inhibition of tumor growth in two different human tumor xenografts prepared from the LS174T colorectal cancer cell line and a glioblastoma cancer cell line. Each group of xenografts (n=5) was treated separately with anti-CEP antibody, Avastin, and PBS alone for three weeks. The tumor size was monitored longitudinally (FIG. 14). Compared to PBS control, both treatment groups exhibited much slower tumor growth rates. Both anti-CEP and Avastin significantly inhibited tumor growth. Unlike the PBS-treated controls, the anti-CEP and Avastin-treated tumor xenografts exhibited no exponential phase of tumor growth at later time points. Immunohistological analysis of tumor tissues indicated that much less new vasculature was formed after anti-CEP or Avastin treatments (FIG. 15), which confirms that the slower tumor growth is associated with inhibition of angiogenesis. These studies showed that anti-CEP is similarly effective as Avastin in both types of xenografts, further suggesting that TLR2- and VEGF-mediated pathways are indeed independent from each other in angiogenesis and can be modulated separately.

In the clinic, patients undergoing Avastin therapy alone often develop drug resistance that limits its efficacy to a few months. In glioblastoma, for example, essentially all patients develop recurrent or progressive disease after initial therapy. Various clinical trials indicated that Avastin has proven effective for recurrent glioblastoma for a short period of time. Continuous Avastin treatment, however, often fails to halt the tumor growth, leading to generally poor clinical outcomes with a median overall survival of only 3.8 months. It is thus critical to develop a combination therapy that can prevent the exponential tumor regrowth immediately after Avastin fails. For this reason, we explored the synergistic effects of Avastin and anti-CEP antibody. A cohort of glioblastoma tumor xenografts was treated first with Avastin for 3 weeks. Then, the xenografts were randomly divided into two groups, one was further treated with Avastin and the other was treated with anti-CEP antibody. As shown in FIG. 16, the xenografts undergoing continuous treatment of Avastin readily entered the second phase of steady exponential tumor growth, suggesting these xenografts had developed drug resistance against Avastin. However, when the previous Avastin-treated xenografts were sequentially treated with anti-CEP antibody, the exponential growth phase was significantly hampered. These studies demonstrated the synergistic effects of Avastin and anti-CEP antibody in inhibiting angiogenesis.

To facilitate future clinical trials of such combination therapy in patients, it is important to identify an effective imaging modality that allows for longitudinal monitoring not only tumor size but also the extent of angiogenesis with high sensitivity and specificity. Because anti-angiogenic therapies often lead to consolidation of tumor mass instead of regression, the standard volumetric measurement is not a sensitive approach and the tumor response is often underestimated. For this reason, we focused on positron emission tomography (PET), which is a functional imaging technique widely used in the clinic that allows for directly monitoring of targets affected by chemotherapies. Because anti-angiogenesis treatment would eventually affect the energy consumption and oxygen supply conditions in the tumor, we conducted PET imaging using either [$^{18}$F]FDG to monitor glucose metabolism rate or [$^{18}$F]FMISO) to assess tumor hypoxia. These imaging studies were expected to enhance our understanding of the biological consequences of CEP monoclonal therapy and of the value of each radiotracer as an imaging marker for non-invasive assessment of its efficacy.

As shown in FIG. 17, the energy consumption in terms of FDG uptake in the colorectal tumor following CEP antibody treatment was quantified following anti-CEP treatment. Compared to PBS-treated controls, anti-CEP treated tumor xenografts exhibited little and insignificant reduction of FDG uptake. This can be explained by the fact that energy consumption is a global indicator of tumor growth and may not directly correlate to vascularization. Because vascularization would directly affect oxygen supply conditions in the tumor, a hypoxia imaging marker such as FMISO may be more sensitive than FDG. Indeed, our longitudinal imaging studies using FMISO-PET showed a significant difference between anti-CEP treated tumors and PBS-treated controls. Quantitative analysis suggested that anti-CEP treatment led to increased uptake of FMISO over time while little or no change was observed in PBS-treated controls. Now that FMISO-PET has been used in patients similar like FDG-PET, use of such PET imaging would greatly facilitate future clinical trials to evaluate the efficacy of anti-CEP therapy.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. An isolated humanized or chimeric anti-carboxyethylpyrrole (anti-CEP) antibody or antigen binding portion thereof, comprising:
    a heavy chain variable domain that includes three CDRs, H-CDR1, H-CDR2, and H-CDR3, of SEQ ID NO: 7, and a light chain variable domain that includes three CDRs, L-CDR1, L-CDR2, and L-CDR3, of SEQ ID NO: 8;
    a heavy chain variable domain that includes three CDRs, H-CDR1, H-CDR2, and H-CDR3, of SEQ ID NO: 38, and a light chain variable domain that includes three CDRs, L-CDR1, L-CDR2, and L-CDR3, of SEQ ID NO: 14;
    a heavy chain variable domain that includes three CDRs, H-CDR1, H-CDR2, and H-CDR3, of SEQ ID NO: 40, and a light chain variable domain that includes three CDRs, L-CDR1, L-CDR2, and L-CDR3, of SEQ ID NO: 16;
    a heavy chain variable domain that includes three CDRs, H-CDR1, H-CDR2, and H-CDR3, of SEQ ID NO: 43, and a light chain variable domain that includes three CDRs, L-CDR1, L-CDR2, and L-CDR3, of SEQ ID NO: 19;
    a heavy chain variable domain that includes three CDRs, H-CDR1, H-CDR2, and H-CDR3, of SEQ ID NO: 47, and a light chain variable domain that includes three CDRs, L-CDR1, L-CDR2, and L-CDR3, of SEQ ID NO: 24;
    a heavy chain variable domain that includes three CDRs, H-CDR1, H-CDR2, and H-CDR3, of SEQ ID NO: 48, and a light chain variable domain that includes three CDRs, L-CDR1, L-CDR2, and L-CDR3, of SEQ ID NO: 25; or
    a heavy chain variable domain that includes three CDRs, H-CDR1, H-CDR2, and H-CDR3, of SEQ ID NO: 51, and a light chain variable domain that includes three CDRs, L-CDR1, L-CDR2, and L-CDR3, of SEQ ID NO: 27.

2. The anti-CEP antibody or antigen binding portion thereof of claim 1, wherein the three heavy chain CDRs, H-CDR1, H-CDR2, and H-CDR3, have the amino acid sequences of, respectively, SEQ ID NO: 1, SEQ ID NO: 2, and SEQ ID NO: 3 and the three light chain CDRs, L-CDR1, L-CDR2, and L-CDR3, have the amino acid sequences of, respectively, SEQ ID NO: 4, SEQ ID NO: 5, and SEQ ID NO: 6.

3. The anti-CEP antibody or antigen binding portion thereof of claim 1, having binding affinity $K_D$ to CEP less than about 5 nM.

4. The anti-CEP antibody or antigen binding portion thereof of claim 1, being a IgG, F(ab)2, F(ab')2, F(ab), or F(ab') fragment.

5. The anti-CEP antibody or antigen binding portion thereof of claim 1, comprising a heavy chain variable domain having at least 90% sequence identity to the amino acid sequence of SEQ ID NO: 9.

6. The anti-CEP antibody or antigen binding portion thereof of claim 1, comprising a light chain variable domain having at least 90% sequence identity to the amino acid sequence of SEQ ID NO: 10.

7. The anti-CEP antibody or antigen binding portion thereof of claim 1, comprising a heavy chain variable domain having at least 90% sequence identity to the amino acid sequence of SEQ ID NO: 9 and a light chain variable domain having at least 90% sequence identity to the amino acid sequence of SEQ ID NO: 10.

8. A method of inhibiting carboxyethylpyrrole (CEP)-induced angiogenesis in a subject in need thereof, the method comprising: administering to the subject an isolated humanized or chimeric anti-CEP antibody or antigen binding portion thereof that specifically binds to CEP and inhibits CEP-induced angiogenesis in the subject, wherein the isolated anti-CEP antibody or antigen binding portion thereof comprises a heavy chain variable domain that includes three CDRs, H-CDR1, H-CDR2, and H-CDR3, of SEQ ID NO: 7, and a light chain variable domain that includes three CDRs, L-CDR1, L-CDR2, and L-CDR3, of SEQ ID NO: 8;
    a heavy chain variable domain that includes three CDRs, H-CDR1, H-CDR2, and H-CDR3, of SEQ ID NO: 38, and a light chain variable domain that includes three CDRs, L-CDR1, L-CDR2, and L-CDR3, of SEQ ID NO: 14;
    a heavy chain variable domain that includes three CDRs, H-CDR1, H-CDR2, and H-CDR3, of SEQ ID NO: 40, and a light chain variable domain that includes three CDRs, L-CDR1, L-CDR2, and L-CDR3, of SEQ ID NO: 16;
    a heavy chain variable domain that includes three CDRs, H-CDR1, H-CDR2, and H-CDR3, of SEQ ID NO: 43, and a light chain variable domain that includes three CDRs, L-CDR1, L-CDR2, and L-CDR3, of SEQ ID NO: 19;
    a heavy chain variable domain that includes three CDRs, H-CDR1, H-CDR2, and H-CDR3, of SEQ ID NO: 47, and a light chain variable domain that includes three CDRs, L-CDR1, L-CDR2, and L-CDR3, of SEQ ID NO: 24;
    a heavy chain variable domain that includes three CDRs, H-CDR1, H-CDR2, and H-CDR3, of SEQ ID NO: 48, and a light chain variable domain that includes three CDRs, L-CDR1, L-CDR2, and L-CDR3, of SEQ ID NO: 25; or
    a heavy chain variable domain that includes three CDRs, H-CDR1, H-CDR2, and H-CDR3, of SEQ ID NO: 51, and a light chain variable domain that includes three CDRs, L-CDR1, L-CDR2, and L-CDR3, of SEQ ID NO: 27.

9. The method of claim 8, wherein the three heavy chain CDRs, H-CDR1, H-CDR2, and H-CDR3, have the amino acid sequences of, respectively, SEQ ID NO: 1, SEQ ID NO: 2, and SEQ ID NO: 3 and the three light chain CDRs, L-CDR1, L-CDR2, and L-CDR3, have the amino acid sequences of, respectively, SEQ ID NO: 4, SEQ ID NO: 5, and SEQ ID NO: 6.

10. The method of claim 8, wherein the anti-CEP antibody or antigen binding portion thereof comprises a heavy chain variable domain having at least 90% sequence identity to the amino acid sequence of SEQ ID NO: 9 and a light chain variable domain having at least 90% sequence identity to the amino acid sequence of SEQ ID NO: 10.

11. The method of claim 8, the anti-CEP antibody or antigen binding portion thereof is administered to tissue to inhibit aberrant angiogenesis.

12. The method of claim 8, the anti-CEP antibody or antigen binding portion thereof is administered to a tumor or cancer and inhibits angiogenesis of the tumor or cancer.

13. A method of treating cancer in a subject in need thereof, the method comprising: administering to the subject an isolated humanized or chimeric anti-carboxyethylpyrrole (anti-CEP) antibody or antigen binding portion thereof that specifically binds to CEP and inhibits CEP-induced angiogenesis in the subject, wherein the isolated anti-CEP antibody or antigen binding portion thereof comprises a heavy chain variable domain that includes three CDRs, H-CDR1, H-CDR2, and H-CDR3, of SEQ ID NO: 7, and a light chain variable domain that includes three CDRs, L-CDR1, L-CDR2, and L-CDR3, of SEQ ID NO: 8;
- a heavy chain variable domain that includes three CDRs, H-CDR1, H-CDR2, and H-CDR3, of SEQ ID NO: 38, and a light chain variable domain that includes three CDRs, L-CDR1, L-CDR2, and L-CDR3, of SEQ ID NO: 14;
- a heavy chain variable domain that includes three CDRs, H-CDR1, H-CDR2, and H-CDR3, of SEQ ID NO: 40, and a light chain variable domain that includes three CDRs, L-CDR1, L-CDR2, and L-CDR3, of SEQ ID NO: 16;
- a heavy chain variable domain that includes three CDRs, H-CDR1, H-CDR2, and H-CDR3, of SEQ ID NO: 43, and a light chain variable domain that includes three CDRs, L-CDR1, L-CDR2, and L-CDR3, of SEQ ID NO: 19;
- a heavy chain variable domain that includes three CDRs, H-CDR1, H-CDR2, and H-CDR3, of SEQ ID NO: 47, and a light chain variable domain that includes three CDRs, L-CDR1, L-CDR2, and L-CDR3, of SEQ ID NO: 24;
- a heavy chain variable domain that includes three CDRs, H-CDR1, H-CDR2, and H-CDR3, of SEQ ID NO: 48, and a light chain variable domain that includes three CDRs, L-CDR1, L-CDR2, and L-CDR3, of SEQ ID NO: 25; or
- a heavy chain variable domain that includes three CDRs, H-CDR1, H-CDR2, and H-CDR3, of SEQ ID NO: 51, and a light chain variable domain that includes three CDRs, L-CDR1, L-CDR2, and L-CDR3, of SEQ ID NO: 27.

14. The method of claim 13, wherein the three heavy chain CDRs, H-CDR1, H-CDR2, and H-CDR3, have the amino acid sequences of, respectively, SEQ ID NO: 1, SEQ ID NO: 2, and SEQ ID NO: 3 and the three light chain CDRs, L-CDR1, L-CDR2, and L-CDR3, have the amino acid sequences of, respectively, SEQ ID NO: 4, SEQ ID NO: 5, and SEQ ID NO: 6.

15. The method of claim 13, wherein the anti-CEP antibody or antigen binding portion thereof comprises a heavy chain variable domain having at least 90% sequence identity to the amino acid sequence of SEQ ID NO: 9 and a light chain variable domain having at least 90% sequence identity to the amino acid sequence of SEQ ID NO: 10.

* * * * *

UNITED STATES PATENT AND TRADEMARK OFFICE
CERTIFICATE OF CORRECTION

PATENT NO.         : 9,957,333 B2
APPLICATION NO.    : 14/689948
DATED              : May 1, 2018
INVENTOR(S)        : Robert G. Salomon et al.

Page 1 of 1

It is certified that error appears in the above-identified patent and that said Letters Patent is hereby corrected as shown below:

In the Specification

Column 1, Lines 13-16 read "Grant No. GM-21249, RES503219, awarded by The National Institutes of General Medicine Studies of the National Institutes of Health." should read --Grant No. GM021249 awarded by The National Institutes of Health.--

Signed and Sealed this
Fifteenth Day of January, 2019

Andrei Iancu
*Director of the United States Patent and Trademark Office*